(12) United States Patent
Adams et al.

(10) Patent No.: US 7,943,659 B2
(45) Date of Patent: May 17, 2011

(54) MAPK/ERK KINASE INHIBITORS

(75) Inventors: Mark E. Adams, San Diego, CA (US); Qing Dong, San Diego, CA (US); Michael B. Wallace, San Diego, CA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 205 days.

(21) Appl. No.: 11/932,615

(22) Filed: Oct. 31, 2007

(65) Prior Publication Data
US 2008/0188453 A1 Aug. 7, 2008

Related U.S. Application Data

(60) Provisional application No. 60/863,748, filed on Oct. 31, 2006.

(51) Int. Cl.
*A61K 31/40* (2006.01)
*C07D 207/34* (2006.01)

(52) U.S. Cl. ........................................ 514/423; 548/537

(58) Field of Classification Search .................. 548/537; 514/423
See application file for complete search history.

(56) References Cited

U.S. PATENT DOCUMENTS
2006/0194802 A1    8/2006    Abdellaoui et al.

FOREIGN PATENT DOCUMENTS
WO    WO2006/058752 A1    6/2006

OTHER PUBLICATIONS

Vippagunta, et al. Advanced Drug Delivery Reviews 48 (2001) 3-26.*
Rouhi. Chemical and Engineering News. (2003) 32-35.*
Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.org/wiki/Cancer.*
Danswan, et al. Document No. 111:134075 retrieved from CAPLUS. Entered in STN on Oct. 14, 1989.*
Cocco, Maria T. et al. "Synthesis and In Vitro Antitumoral Activity of New N-Phenyl-3-pyrrolecarbothioamides" Biorganic & Medicianl Chemistry, (2003), vol. 11, pp. 495-503. XP-002475069.
Price, S: "Putative allosteric MEK1 and MEK2 inhibitors" Expert Opinion on Therapeutic Patents 200806 GB, vol. 18, No. 6, Jun. 2008, pp. 603-627, XP002494157, ISSN: 1354-3776.
Varaprasad, Chamakura V. N. S. et al. "Discovery of 3-hydroxy-4-carboxyalkylamidino-5-arylamino-isothiazoles as potent MEK1 inhibitors" Bioorganic & Medicinal Chemistry Letters, (2006), vol. 16, pp. 3975-3980.

* cited by examiner

*Primary Examiner* — Shawquia Young
(74) *Attorney, Agent, or Firm* — David M. Stemerick; Mitchell R. Brustein

(57) ABSTRACT

Compounds, pharmaceutical compositions, kits and methods are provided for use with MEK that comprise a compound selected from the group consisting of:

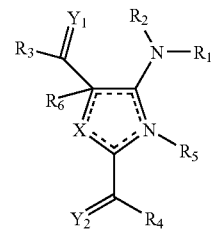

wherein the variables are as defined herein.

30 Claims, 11 Drawing Sheets

FIGURE 1A

Protein sequence encoding residues 2-393 of human MEK1 with deletion from residues 32-51, mutations S218E and S222D, and an N-terminal 6-histidine tag [SEQ ID NO: 1]

```
Met Ser Tyr Tyr His His His His His His Asp Tyr Asp Ile Pro Thr
1               5                   10              15

Thr Glu Asn Leu Tyr Phe Gln Gly Ala Met Gly Ser Pro Lys Lys Lys
            20                  25                  30

Pro Thr Pro Ile Gln Leu Asn Pro Ala Pro Asp Gly Ser Ala Val Asn
        35                  40                  45

Gly Thr Ser Ser Ala Glu Thr Asn Leu Glu Ala Phe Leu Thr Gln Lys
    50                  55                  60

Gln Lys Val Gly Glu Leu Lys Asp Asp Asp Phe Glu Lys Ile Ser Glu
65                  70                  75                  80

Leu Gly Ala Gly Asn Gly Gly Val Val Phe Lys Val Ser His Lys Pro
                85                  90                  95

Ser Gly Leu Val Met Ala Arg Lys Leu Ile His Leu Glu Ile Lys Pro
            100                 105                 110

Ala Ile Arg Asn Gln Ile Ile Arg Glu Leu Gln Val Leu His Glu Cys
        115                 120                 125

Asn Ser Pro Tyr Ile Val Gly Phe Tyr Gly Ala Phe Tyr Ser Asp Gly
        130                 135                 140

Glu Ile Ser Ile Cys Met Glu His Met Asp Gly Gly Ser Leu Asp Gln
145                 150                 155                 160

Val Leu Lys Lys Ala Gly Arg Ile Pro Glu Gln Ile Leu Gly Lys Val
                165                 170                 175

Ser Ile Ala Val Ile Lys Gly Leu Thr Tyr Leu Arg Glu Lys His Lys
                180                 185                 190
```

FIGURE 1B

```
Ile Met His Arg Asp Val Lys Pro Ser Asn Ile Leu Val Asn Ser Arg
        195                 200                 205

Gly Glu Ile Lys Leu Cys Asp Phe Gly Val Ser Gly Gln Leu Ile Asp
        210                 215                 220

Glu Met Ala Asn Asp Phe Val Gly Thr Arg Ser Tyr Met Ser Pro Glu
225                 230                 235                 240

Arg Leu Gln Gly Thr His Tyr Ser Val Gln Ser Asp Ile Trp Ser Met
                245                 250                 255

Gly Leu Ser Leu Val Glu Met Ala Val Gly Arg Tyr Pro Ile Pro Pro
                260                 265                 270

Pro Asp Ala Lys Glu Leu Glu Leu Met Phe Gly Cys Gln Val Glu Gly
        275                 280                 285

Asp Ala Ala Glu Thr Pro Pro Arg Pro Arg Thr Pro Gly Arg Pro Leu
        290                 295                 300

Ser Ser Tyr Gly Met Asp Ser Arg Pro Pro Met Ala Ile Phe Glu Leu
305                 310                 315                 320

Leu Asp Tyr Ile Val Asn Glu Pro Pro Pro Lys Leu Pro Ser Gly Val
                325                 330                 335

Phe Ser Leu Glu Phe Gln Asp Phe Val Asn Lys Cys Leu Ile Lys Asn
                340                 345                 350

Pro Ala Glu Arg Ala Asp Leu Lys Gln Leu Met Val His Ala Phe Ile
        355                 360                 365

Lys Arg Ser Asp Ala Glu Val Asp Phe Ala Gly Trp Leu Cys Ser
        370                 375                 380

Thr Ile Gly Leu Asn Gln Pro Ser Thr Pro Thr His Ala Ala Gly Val
385                 390                 395                 400
```

FIGURE 1C

DNA sequence encoding SEQ ID NO: 1 [SEQ ID NO: 2]

```
atgtcgtact accatcacca tcaccatcac gattacgata tcccaacgac cgaaaacctg      60
tattttcagg gcgccatggg atcccccaag aagaagccga cgcccatcca gctgaacccg     120
gcccccgacg gctctgcagt taacgggacc agctctgcgg agaccaactt ggaggccttt     180
cttacccaga agcagaaggt gggagaactg aaggatgacg actttgagaa gatcagtgag     240
ctggggctg gcaatggcgg tgtggtgttc aaggtctccc acaagccttc tggcctggtc     300
atggccagaa agctaattca tctggagatc aaaccgcaa tccggaacca gatcataagg     360
gagctgcagg ttctgcatga gtgcaactct ccgtacatcg tgggcttcta tggtgcgttc     420
tacagcgatg gcgagatcag tatctgcatg gagcacatgg atgaggttc tctggatcaa     480
gtcctgaaga agctggaag aattcctgaa caatttttag gaaaagttag cattgctgta     540
ataaaaggcc tgacatatct gagggagaag cacaagatca tgcacagaga tgtcaagccc     600
tccaacatcc tagtcaactc ccgtggggag atcaagctct gtgactttgg ggtcagcggg     660
cagctcatcg acgaaatggc caacgacttc gtgggcacaa ggtcctacat gtcgccagaa     720
agactccagg ggactcatta ctctgtgcag tcagacatct ggagcatggg actgtctctg     780
gtagagatgg cggttgggag gtatcccatc cctcctccag atgccaagga gctggagctg     840
atgtttgggt gccaggtgga aggagatgcg gctgagaccc cacccaggcc aaggacccc     900
ggaggcccc ttagctcata cggaatggac agccgacctc ccatggcaat ttttgagttg     960
ttggattaca tagtcaacga gcctcctcca aaactgccca gtggagtgtt cagtctggaa    1020
tttcaagatt ttgtgaataa atgcttaata aaaaacccg cagagagagc agatttgaag    1080
caactcatgg ttcatgcttt tatcaagaga tctgatgctg aggaagtgga ttttgcaggt    1140
tggctctgct ccaccatcgg ccttaaccag cccagcacac caacccatgc tgctggcgtc    1200
taa                                                                 1203
```

FIGURE 1D

Protein sequence encoding residues 1-400 of human MEK2 with mutations S222E and S226D, and an N-terminal 6-histidine tag [SEQ ID NO: 3]

```
Met Ser Tyr Tyr His His His His His His Asp Tyr Asp Ile Pro Thr
1               5                   10                  15

Thr Glu Asn Leu Tyr Phe Gln Gly Ala Met Glu Pro Met Leu Ala Arg
            20                  25                  30

Arg Lys Pro Val Leu Pro Ala Leu Thr Ile Asn Pro Thr Ile Ala Glu
            35              40                  45

Gly Pro Ser Pro Thr Ser Glu Gly Ala Ser Glu Ala Asn Leu Val Asp
        50              55                  60

Leu Gln Lys Lys Leu Glu Glu Leu Glu Leu Asp Glu Gln Gln Lys Lys
65              70                  75                      80

Arg Leu Glu Ala Phe Leu Thr Gln Lys Ala Lys Val Gly Glu Leu Lys
                85                  90                  95

Asp Asp Asp Phe Glu Arg Ile Ser Glu Leu Gly Ala Gly Asn Gly Gly
                100                 105                 110

Val Val Thr Lys Val Gln His Arg Pro Ser Gly Leu Ile Met Ala Arg
            115                 120             125

Lys Leu Ile His Leu Glu Ile Lys Pro Ala Ile Arg Asn Gln Ile Ile
        130             135                 140

Arg Glu Leu Gln Val Leu His Glu Cys Asn Ser Pro Tyr Ile Val Gly
145                 150             155                     160

Phe Tyr Gly Ala Phe Tyr Ser Asp Gly Glu Ile Ser Ile Cys Met Glu
                165                 170             175

His Met Asp Gly Gly Ser Leu Asp Gln Val Leu Lys Glu Ala Lys Arg
            180             185                 190
```

FIGURE 1E

```
Ile Pro Glu Glu Ile Leu Gly Lys Val Ser Ile Ala Val Leu Arg Gly
        195                 200                 205

Leu Ala Tyr Leu Arg Glu Lys His Gln Ile Met His Arg Asp Val Lys
        210                 215                 220

Pro Ser Asn Ile Leu Val Asn Ser Arg Gly Glu Ile Lys Leu Cys Asp
225                 230                 235                 240

Phe Gly Val Ser Gly Gln Leu Ile Asp Glu Met Ala Asn Asp Phe Val
                245                 250                 255

Gly Thr Arg Ser Tyr Met Ala Pro Glu Arg Leu Gln Gly Thr His Tyr
            260                 265                 270

Ser Val Gln Ser Asp Ile Trp Ser Met Gly Leu Ser Leu Val Glu Leu
        275                 280                 285

Ala Val Gly Arg Tyr Pro Ile Pro Pro Asp Ala Lys Glu Leu Glu
        290                 295                 300

Ala Ile Phe Gly Arg Pro Val Val Asp Gly Glu Glu Gly Glu Pro His
305                 310                 315                 320

Ser Ile Ser Pro Arg Pro Arg Pro Pro Gly Arg Pro Val Ser Gly His
                325                 330                 335

Gly Met Asp Ser Arg Pro Ala Met Ala Ile Phe Glu Leu Leu Asp Tyr
            340                 345                 350

Ile Val Asn Glu Pro Pro Pro Lys Leu Pro Asn Gly Val Phe Thr Pro
        355                 360                 365

Asp Phe Gln Glu Phe Val Asn Lys Cys Leu Ile Lys Asn Pro Ala Glu
        370                 375                 380

Arg Ala Asp Leu Lys Met Leu Thr Asn His Thr Phe Ile Lys Arg Ser
385                 390                 395                 400
```

FIGURE 1F

```
Glu Val Glu Glu Val Asp Phe Ala Gly Trp Leu Cys Lys Thr Leu Arg
            405                 410                 415

Leu Asn Gln Pro Gly Thr Pro Thr Arg Thr Ala Val
            420                 425
```

DNA sequence encoding SEQ ID NO: 3 [SEQ ID NO: 4]

```
atgtcgtact accatcacca tcaccatcac gattacgata tcccaacgac cgaaaacctg      60
tattttcagg gcgccatgga acccatgctg gcccggagga agccggtgct gccggcgctc     120
accatcaacc ctaccatcgc cgagggccca tcccctacca gcgagggcgc ctccgaggca     180
aacctggtgg acctgcagaa gaagctggag gagctggaac ttgacgagca gcagaagaag     240
cggctggaag cctttctcac ccagaaagcc aaggtcggcg aactcaaaga cgatgacttc     300
gaaaggatct cagagctggg cgcgggcaac ggcggggtgg tcaccaaagt ccagcacaga     360
ccctcgggcc tcatcatggc caggaagctg atccaccttg atcaagcc ggccatccgg      420
aaccagatca tccgcgagct gcaggtcctg cacgaatgca actcgccgta catcgtgggc     480
ttctacgggg ccttctacag tgacggggag atcagcattt gcatggaaca catggacggc     540
ggctccctgg accaggtgct gaaagaggcc aagaggattc ccgaggagat cctggggaaa     600
gtcagcatcg cggttctccg gggcttggcg tacctccgag agaagcacca gatcatgcac     660
cgagatgtga agccctccaa catcctcgtg aactctagag gggagatcaa gctgtgtgac     720
ttcggggtga gcggccagct catagacgaa atggccaacg acttcgtggg cacgcgctcc     780
tacatggctc cggagcggtt gcagggcaca cattactcgg tgcagtcgga catctggagc     840
atgggcctgt ccctggtgga gctggccgtc ggaaggtacc ccatccccc gcccgacgcc     900
aaagagctgg aggccatctt tggccggccc gtggtcgacg gggaagaagg agagcctcac     960
agcatctcgc ctcggccgag gcccccgggg cgccccgtca gcggtcacgg gatggatagc    1020
cggcctgcca tggccatctt tgaactcctg gactatattg tgaacgagcc acctcctaag   1080
```

FIGURE 1G

```
ctgcccaacg gtgtgttcac ccccgacttc caggagtttg tcaataaatg cctcatcaag    1140
aacccagcgg agcgggcgga cctgaagatg ctcacaaacc acaccttcat caagcggtcc    1200
gaggtggaag aagtggattt tgccggctgg ttgtgtaaaa ccctgcggct gaaccagccc    1260
ggcacaccca cgcgcaccgc cgtgtaa                                        1287
```

Protein sequence encoding residues 1-379 of human ERK1 with an N-terminal GST tag [SEQ ID NO: 5]

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
            35                  40                  45

Gly Leu Glu Phe Pro Asn Leu Pro Tyr Tyr Ile Asp Gly Asp Val Lys
        50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
            130                 135                 140

Gly Asp His Val Thr His Pro Asp Phe Met Leu Tyr Asp Ala Leu Asp
145                 150                 155                 160
```

FIGURE 1H

Val Val Leu Tyr Met Asp Pro Met Cys Leu Asp Ala Phe Pro Lys Leu
            165             170             175

Val Cys Phe Lys Lys Arg Ile Glu Ala Ile Pro Gln Ile Asp Lys Tyr
            180             185             190

Leu Lys Ser Ser Lys Tyr Ile Ala Trp Pro Leu Gln Gly Trp Gln Ala
            195             200             205

Thr Phe Gly Gly Gly Asp His Pro Pro Lys Ser Asp Leu Glu Val Leu
    210             215             220

Phe Gln Gly Pro Leu Gly Ser Pro Asn Ser Gly Met Ala Ala Ala Ala
225             230             235             240

Ala Gln Gly Gly Gly Gly Gly Glu Pro Arg Arg Thr Glu Gly Val Gly
            245             250             255

Pro Gly Val Pro Gly Glu Val Glu Met Val Lys Gly Gln Pro Phe Asp
            260             265             270

Val Gly Pro Arg Tyr Thr Gln Leu Gln Tyr Ile Gly Glu Gly Ala Tyr
            275             280             285

Gly Met Val Ser Ser Ala Tyr Asp His Val Arg Lys Thr Arg Val Ala
    290             295             300

Ile Lys Lys Ile Ser Pro Phe Glu His Gln Thr Tyr Cys Gln Arg Thr
305             310             315             320

Leu Arg Glu Ile Gln Ile Leu Leu Arg Phe Arg His Glu Asn Val Ile
            325             330             335

Gly Ile Arg Asp Ile Leu Arg Ala Ser Thr Leu Glu Ala Met Arg Asp
            340             345             350

Val Tyr Ile Val Gln Asp Leu Met Glu Thr Asp Leu Tyr Lys Leu Leu
            355             360             365

FIGURE 1I

```
Lys Ser Gln Gln Leu Ser Asn Asp His Ile Cys Tyr Phe Leu Tyr Gln
    370             375             380

Ile Leu Arg Gly Leu Lys Tyr Ile His Ser Ala Asn Val Leu His Arg
385             390             395                         400

Asp Leu Lys Pro Ser Asn Leu Leu Ile Asn Thr Thr Cys Asp Leu Lys
                405             410                 415

Ile Cys Asp Phe Gly Leu Ala Arg Ile Ala Asp Pro Glu His Asp His
            420             425             430

Thr Gly Phe Leu Thr Glu Tyr Val Ala Thr Arg Trp Tyr Arg Ala Pro
        435             440             445

Glu Ile Met Leu Asn Ser Lys Gly Tyr Thr Lys Ser Ile Asp Ile Trp
    450             455             460

Ser Val Gly Cys Ile Leu Ala Glu Met Leu Ser Asn Arg Pro Ile Phe
465             470             475                         480

Pro Gly Lys His Tyr Leu Asp Gln Leu Asn His Ile Leu Gly Ile Leu
                485             490                 495

Gly Ser Pro Ser Gln Glu Asp Leu Asn Cys Ile Ile Asn Met Lys Ala
                500             505             510

Arg Asn Tyr Leu Gln Ser Leu Pro Ser Lys Thr Lys Val Ala Trp Ala
        515             520             525

Lys Leu Phe Pro Lys Ser Asp Ser Lys Ala Leu Asp Leu Leu Asp Arg
    530             535             540

Met Leu Thr Phe Asn Pro Asn Lys Arg Ile Thr Val Glu Glu Ala Leu
545             550             555                         560

Ala His Pro Tyr Leu Glu Gln Tyr Tyr Asp Pro Thr Asp Glu Pro Val
                565             570                 575
```

FIGURE 1J

```
Ala Glu Glu Pro Phe Thr Phe Ala Met Glu Leu Asp Asp Leu Pro Lys
            580                 585                 590

Glu Arg Leu Lys Glu Leu Ile Phe Gln Glu Thr Ala Arg Phe Gln Pro
        595                 600                 605

Gly Val Leu Glu Ala Pro
        610
```

DNA sequence encoding SEQ ID NO: 5 [SEQ ID NO: 6]

```
atgtccccta tactaggtta ttggaaaatt aagggccttg tgcaacccac tcgacttctt    60
ttggaatatc ttgaagaaaa atatgaagag catttgtatg agcgcgatga aggtgataaa   120
tggcgaaaca aaaagtttga attgggtttg gagtttccca atcttcctta ttatattgat   180
ggtgatgtta aattaacaca gtctatggcc atcatacgtt atatagctga caagcacaac   240
atgttgggtg gttgtccaaa agagcgtgca gagatttcaa tgcttgaagg agcggttttg   300
gatattagat acggtgtttc gagaattgca tatagtaaag actttgaaac tctcaaagtt   360
gattttctta gcaagctacc tgaaatgctg aaaatgttcg aagatcgttt atgtcataaa   420
acatatttaa atggtgatca tgtaacccat cctgacttca tgttgtatga cgctcttgat   480
gttgttttat acatggaccc aatgtgcctg gatgcgttcc caaaattagt ttgttttaaa   540
aaacgtattg aagctatccc acaaattgat aagtacttga atccagcaa gtatatagca   600
tggcctttgc agggctggca agccacgttt ggtggtggcg accatcctcc aaaatcggat   660
ctggaagttc tgttccaggg gcccctggga tccccgaatt ccgggatggc ggcggcggcg   720
gctcaggggg gcggggggcgg ggagcccgt agaaccgagg gggtcggccc ggggtcccg   780
ggggaggtgg agatggtgaa ggggcagccg ttcgacgtgg gccgcgcta cacgcagttg   840
cagtacatcg gcgagggcgc gtacggcatg gtcagctcgg cctatgacca cgtgcgcaag   900
actcgcgtgg ccatcaagaa gatcagcccc ttcgaacatc agacctactg ccagcgcacg   960
ctccgggaga tccagatcct gctgcgcttc cgccatgaga atgtcatcgg catccgagac  1020
attctgcggg cgtccaccct ggaagccatg agagatgtct acattgtgca ggacctgatg  1080
```

FIGURE 1K

```
gagactgacc tgtacaagtt gctgaaaagc cagcagctga gcaatgacca tatctgctac    1140
ttcctctacc agatcctgcg gggcctcaag tacatccact ccgccaacgt gctccaccga    1200
gatctaaagc cctccaacct gctcatcaac accacctgcg accttaagat ttgtgatttc    1260
ggcctggccc ggattgccga tcctgagcat gaccacaccg gcttcctgac ggagtatgtg    1320
gctacgcgct ggtaccgggc cccagagatc atgctgaact ccaagggcta taccaagtcc    1380
atcgacatct ggtctgtggg ctgcattctg gctgagatgc tctctaaccg gcccatcttc    1440
cctggcaagc actacctgga tcagctcaac cacattctgg gcatcctggg ctccccatcc    1500
caggaggacc tgaattgtat catcaacatg aaggcccgaa actacctaca gtctctgccc    1560
tccaagacca aggtggcttg ggccaagctt ttccccaagt cagactccaa agcccttgac    1620
ctgctggacc ggatgttaac ctttaacccc aataaacgga tcacagtgga ggaagcgctg    1680
gctcacccct acctggagca gtactatgac ccgacggatg agccagtggc cgaggagccc    1740
ttcaccttcg ccatggagct ggatgaccta cctaaggagc ggctgaagga gctcatcttc    1800
caggagacag cacgcttcca gcccggagtg ctggaggccc cctag                    1845
```

MAPK/ERK KINASE INHIBITORS

RELATED APPLICATION

This application claims the benefit of U.S. Provisional Application No. 60/863,748, filed Oct. 31, 2006, which is incorporated herein by reference.

FIELD OF THE INVENTION

The present invention relates to compounds that may be used to inhibit Mitogen-Activated Protein kinases (also known as MEK and MAPK/ERK kinases), such as Mitogen-Activated Protein Kinase Kinase 1 (also known as MAPKK1, MAPK/ERK Kinase 1, and MEK1) and Mitogen-Activated Protein Kinase Kinase 2 (also known as MAPKK2, MAPK/ERK Kinase 2, and MEK2), as well as compositions of matter, kits and articles of manufacture comprising these compounds. The invention also relates to methods for inhibiting MEK and/or ERK activity, and treatment methods using compounds according to the present invention. In addition, the invention relates to methods of making the compounds of the present invention, as well as intermediates useful in such methods.

BACKGROUND OF THE INVENTION

The mitogen activated protein kinase (MAPK) signaling pathways are involved in cellular events such as growth, differentiation and stress responses (J. Biol. Chem. (1993) 268, 14553-14556). Four parallel MAPK pathways have been identified to date: ERK1/ERK2, JNK, p38 and ERK5. These pathways are linear kinase cascades in that MAPKKK phosphorylates and activates MAPKK, and MAPKK phosphorylates and activates MAPK. To date, seven MAPKK homologs (MEK1, MEK2, MKK3, MKK4/SEK, MEK5, MKK6, and MKK7) and four MAPK families (ERK1/2, JNK, p38, and ERK5) have been identified. Activation of these pathways regulates the activity of a number of substrates through phosphorylation. These substrates include: transcription factors such as TCF, c-myc, ATF2 and the AP-1 components, fos and Jun; cell surface components EGF-R; cytosolic components including PHAS-I, p90$^{rsk}$, cPLA$_2$ and c-Raf-1; and cytoskeleton components such as tau and MAP2. MAPK signaling cascades are involved in controlling cellular processes including proliferation, differentiation, apoptosis, and stress responses.

Of the known MAPK signaling pathways, the RAF-MEK-ERK pathway mediates proliferative and anti-apoptotic signaling from growth factors and oncogenic factors such as Ras and Raf mutant phenotypes that promote tumor growth, progression, and metastasis. By virtue of its central role in mediating the transmission of growth-promoting signals from multiple growth factor receptors, the RAF-MEK-ERK pathway provides molecular targets with potentially broad therapeutic applications in, for example, cancerous and nooncancerous hyperproliferative disorders, immunomodulation and inflammation.

MEK occupies a strategic downstream position in the RAF-MEK-ERK pathway catalyzing the phosphorylation of its MAPK substrates, ERK1 and ERK2. Anderson et al "Requirement for integration of signals from two distinct phosphorylation pathways for activation of MAP kinase." Nature 1990, v.343, pp. 651-653. In the ERK pathway, MAPKK corresponds with MEK (MAP kinase ERK Kinase) and the MAPK corresponds with ERK (Extracellular Regulated Kinase). No substrates for MEK have been identified other than ERK1 and ERK2. Seger et al. "Purification and characterization of mitogen-activated protein kinase activator(s) from epidermal growth factor-stimulated A431 cells." J. Biol. Chem., 1992, v. 267, pp. 14373-14381. This tight selectivity, in addition to the unique ability to act as a dual-specificity kinase, is consistent with MEK's central role in integration of signals into the MAPK pathway. MEK also appears to associate strongly with MAP kinase prior to phosphorylating it, suggesting that phosphorylation of MAP kinase by MEK may require a prior strong interaction between the two proteins. Both this requirement and the unusual specificity of MEK are suggestive that it may have enough difference in its mechanism of action to other protein kinases that selective inhibitors of MEK, possibly operating through allosteric mechanisms rather than through the usual blockade of the ATP binding site, may be found.

Constitutive action of MAPKs has been reported in >30% of primary tumor cell lines including cell lines derived from colon, lung, breast, pancreas, ovary, and kidney. Hoshino et al. "Constitutive activation of the 41-/43-kDa mitogen-activated protein kinase signaling pathway in human tumors." Oncogene, 1999, v. 18, pp. 813-822. Higher concentrations of active MAPK/ERK (pMAPK/pERK) have been detected in tumor tissue as compared to normal adjacent tissue. Sivaraman et al "Hyperexpression of mitogen-activated protein kinase in human breast cancer." J. Clin. Invest., 1997, v. 99, pp. 1478-1483.

There is a continued need to find new therapeutic agents to treat human diseases. The MAPK/ERK kinases, specifically but not limited to MEK1 and MEK2, are especially attractive targets for the discovery of new therapeutics due to their important role in cancerous hyperproliferative disorders (e.g., brain, lung, squamous cell, bladder, gastric, pancreatic, breast, head, neck, renal, kidney, ovarian, prostate, colorectal, prostate, colon, epidermoid, esophageal, testicular, gynecological or thyroid cancer; non-cancerous hyperproliferative disorders (e.g., benign hyperplasia of the skin (e.g., psoriasis), restenosis, and benign prostatic hypertrophy (BPH)); pancreatitis; kidney disease; pain; preventing blastocyte implantation; treating diseases related to vasculogenesis or angiogenesis (e.g., tumor angiogenesis, acute and chronic inflammatory disease such as rheumatoid arthritis, atherosclerosis, inflammatory bowel disease, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer); asthma; neutrophil chemotaxis; septic shock; T-cell mediated diseases where immune suppression would be of value (e.g., the prevention of organ transplant rejection, graft versus host disease, lupus erythematosus, multiple sclerosis, and rheumatoid arthritis); conditions where neutrophil influx drives tissue destruction (e.g., reperfusion injury in myocardial infarction and stroke and inflammatory arthritis); atherosclerosis; inhibition of keratinocyte responses to growth factor cocktails; and other diseases.

SUMMARY OF THE INVENTION

The present invention relates to compounds that have activity for inhibiting MAPK/ERK kinases. The present invention also provides compositions, articles of manufacture and kits comprising these compounds, as well as methods for inhibiting MEK and treatment methods using compounds according to the present invention. In addition, the invention relates to methods of making the compounds of the present invention, as well as intermediates useful in such methods.

In one embodiment, a pharmaceutical composition is provided that comprises a MEK inhibitor according to the present invention as an active ingredient. Pharmaceutical compositions according to the invention may optionally comprise 0.001%-100% of one or more inhibitors of this invention. These pharmaceutical compositions may be administered or coadministered by a wide variety of routes, including for example, orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compositions may also be administered or coadministered in slow release dosage forms.

The invention is also directed to kits and other articles of manufacture for treating disease states associated with MEK.

In one embodiment, a kit is provided that comprises a composition comprising at least one MEK inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one MEK inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

Also provided are methods for preparing compounds, compositions and kits according to the present invention. For example, several synthetic schemes are provided herein for synthesizing compounds according to the present invention.

Also provided are methods for using compounds, compositions, kits and articles of manufacture according to the present invention.

In one embodiment, the compounds, compositions, kits and articles of manufacture are used to inhibit the activity of MEK and/or ERK. In particular, the compounds, compositions, kits and articles of manufacture can be used to inhibit the activity of MEK1. In addition, the compounds, compositions, kits and articles of manufacture can be used to inhibit the activity of MEK2. Further, the compounds, compositions, kits and articles of manufacture can be used to inhibit the activity of ERK1. Also, the compounds, compositions, kits and articles of manufacture can be used to inhibit the activity of ERK2.

In another embodiment, the compounds, compositions, kits and articles of manufacture are used to treat a disease state for which MEK and/or ERK possess activity that contributes to the pathology and/or symptomology of the disease state.

In another embodiment, a compound according to the present invention is administered to a subject wherein MEK and/or ERK activity within the subject is altered, preferably reduced.

In another embodiment, a prodrug of a compound according to the present invention is administered to a subject that is converted to the compound in vivo where it inhibits MEK and/or ERK.

In another embodiment, a method of inhibiting MEK and/or ERK is provided that comprises contacting a MEK and/or ERK with a compound according to the present invention.

In another embodiment, a method of inhibiting MEK and/or ERK is provided that comprises causing a compound according to the present invention to be present in a subject in order to inhibit MEK and/or ERK in vivo.

In another embodiment, a method of inhibiting a MEK and/or ERK is provided that comprises administering a first compound to a subject that is converted in vivo to a second compound wherein the second compound inhibits MEK and/or ERK in vivo. It is noted that the compounds of the present invention may be the first or second compounds.

In another embodiment, a therapeutic method is provided that comprises administering a compound according to the present invention.

In another embodiment, a method is provided for treating a condition in a patient that is known to be mediated by MEK and/or ERK, or which is known to be treated by MEK inhibitors, the method comprising administering to the patient a therapeutically effective amount of a compound according to the present invention.

In another embodiment, a method is provided for treating a disease state for which MEK and/or ERK possess activity that contributes to the pathology and/or symptomology of the disease state, the method comprising: causing a compound according to the present invention to be present in a subject in a therapeutically effective amount for the disease state.

In another embodiment, a method is provided for treating a disease state for which MEK and/or ERK possess activity that contributes to the pathology and/or symptomology of the disease state, the method comprising: administering a first compound to a subject that is converted in vivo to a second compound such that the second compound is present in the subject in a therapeutically effective amount for the disease state. It is noted that the compounds of the present invention may be the first or second compounds.

In another embodiment, a method is provided for treating a disease state for which MEK and/or ERK possess activity that contributes to the pathology and/or symptomology of the disease state, the method comprising: administering a compound according to the present invention to a subject such that the compound is present in the subject in a therapeutically effective amount for the disease state.

In another embodiment, a method is provided for using a compound according to the present invention in order to manufacture a medicament for use in the treatment of a disease state which is known to be mediated by MEK and/or ERK, or that is known to be treated by MEK inhibitors.

It is noted in regard to all of the above embodiments that the present invention is intended to encompass all pharmaceutically acceptable ionized forms (e.g., salts) and solvates (e.g., hydrates) of the compounds, regardless of whether such ionized forms and solvates are specified since it is well know in the art to administer pharmaceutical agents in an ionized or solvated form. It is also noted that unless a particular stereochemistry is specified, recitation of a compound is intended to encompass all possible stereoisomers (e.g., enantiomers or diastereomers depending on the number of chiral centers), independent of whether the compound is present as an individual isomer or a mixture of isomers. Further, unless otherwise specified, recitation of a compound is intended to encompass all possible resonance forms and tautomers. With regard to the claims, the language "compound comprising the formula," "compound having the formula" and "compound of the formula" is intended to encompass the compound and all pharmaceutically acceptable ionized forms and solvates, all possible stereoisomers, and all possible resonance forms and tautomers unless otherwise specifically specified in the particular claim.

It is further noted that prodrugs may also be administered which are altered in vivo and become a compound according to the present invention. The various methods of using the compounds of the present invention are intended, regardless of whether prodrug delivery is specified, to encompass the administration of a prodrug that is converted in vivo to a compound according to the present invention. It is also noted that certain compounds of the present invention may be altered in vivo prior to inhibit MEK and thus may themselves be prodrugs for another compound. Such prodrugs of another compound may or may not themselves independently have MEK and/or ERK inhibitory activity.

BRIEF DESCRIPTION OF THE FIGURES

FIG. 1 illustrates SEQ ID NOS: 1-6 referred to in this application.

DEFINITIONS

Unless otherwise stated, the following terms used in the specification and claims shall have the following meanings for the purposes of this Application.

It is noted that, as used in the specification and the appended claims, the singular forms "a," "an" and "the" include plural referents unless the context clearly dictates otherwise. Further, definitions of standard chemistry terms may be found in reference works, including Carey and Sundberg "ADVANCED ORGANIC CHEMISTRY $4^{TH}$ ED." Vols. A (2000) and B (2001), Plenum Press, New York. Also, unless otherwise indicated, conventional methods of mass spectroscopy, NMR, HPLC, protein chemistry, biochemistry, recombinant DNA techniques and pharmacology, within the skill of the art are employed.

"Alicyclic" means a moiety comprising a non-aromatic ring structure. Alicyclic moieties may be saturated or partially unsaturated with one, two or more double or triple bonds. Alicyclic moieties may also optionally comprise heteroatoms such as nitrogen, oxygen and sulfur. The nitrogen atoms can be optionally quaternerized or oxidized and the sulfur atoms can be optionally oxidized. Examples of alicyclic moieties include, but are not limited to moieties with ($C_{3-8}$) rings such as cyclopropyl, cyclohexane, cyclopentane, cyclopentene, cyclopentadiene, cyclohexane, cyclohexene, cyclohexadiene, cycloheptane, cycloheptene, cycloheptadiene, cyclooctane, cyclooctene, and cyclooctadiene.

"Aliphatic" means a moiety characterized by a straight or branched chain arrangement of constituent carbon atoms and may be saturated or partially unsaturated with one, two or more double or triple bonds.

"Alkenyl" means a straight or branched, carbon chain that contains at least one carbon-carbon double bond (—CR=CR'— or —CR=CR'R", wherein R, R' and R" are each independently hydrogen or further substituents). Examples of alkenyl include vinyl, allyl, isopropenyl, pentenyl, hexenyl, heptenyl, 1-propenyl, 2-butenyl, 2-methyl-2-butenyl, and the like. In particular embodiments, "alkenyl," either alone or represented along with another radical, can be a ($C_{2-20}$)alkenyl, a ($C_{2-15}$)alkenyl, a ($C_{2-10}$)alkenyl, a ($C_{2-5}$)alkenyl or a ($C_{2-3}$)alkenyl. Alternatively, "alkenyl," either alone or represented along with another radical, can be a ($C_2$)alkenyl, a ($C_3$)alkenyl or a ($C_4$)alkenyl.

"Alkenylene" means a straight or branched, divalent carbon chain having one or more carbon-carbon double bonds (—CR=CR'—, wherein R and R' are each independently hydrogen or further substituents). Examples of alkenylene include ethene-1,2-diyl, propene-1,3-diyl, methylene-1,1-diyl, and the like. In particular embodiments, "alkenylene," either alone or represented along with another radical, can be a ($C_{2-20}$) alkenylene, a ($C_{2-15}$) alkenylene, a ($C_{2-10}$) alkenylene, a ($C_{2-5}$) alkenylene or a ($C_{2-3}$) alkenylene. Alternatively, "alkenylene," either alone or represented along with another radical, can be a ($C_2$) alkenylene, a ($C_3$) alkenylene or a ($C_4$) alkenylene.

"Alkoxy" means an oxygen moiety having a further alkyl substituent. The alkoxy groups of the present invention can be optionally substituted.

"Alkyl" represented by itself means a straight or branched, saturated or unsaturated, aliphatic radical having a chain of carbon atoms, optionally with one or more of the carbon atoms being replaced with oxygen (See "oxaalkyl"), a carbonyl group (See "oxoalkyl"), sulfur (See "thioalkyl"), and/or nitrogen (See "azaalkyl"). ($C_X$)alkyl and ($C_{X-Y}$)alkyl are typically used where X and Y indicate the number of carbon atoms in the chain. For example, ($C_{1-6}$)alkyl includes alkyls that have a chain of between 1 and 6 carbons (e.g., methyl, ethyl, propyl, isopropyl, butyl, sec-butyl, isobutyl, tert-butyl, vinyl, allyl, 1-propenyl, isopropenyl, 1-butenyl, 2-butenyl, 3-butenyl, 2-methylallyl, ethynyl, 1-propynyl, 2-propynyl, and the like). Alkyl represented along with another radical (e.g., as in arylalkyl, heteroarylalkyl and the like) means a straight or branched, saturated or unsaturated aliphatic divalent radical having the number of atoms indicated or when no atoms are indicated means a bond (e.g., ($C_{6-10}$)aryl($C_{1-3}$)alkyl includes, benzyl, phenethyl, 1-phenylethyl, 3-phenylpropyl, 2-thienylmethyl, 2-pyridinylmethyl and the like). In particular embodiments, "alkyl," either alone or represented along with another radical, can be a ($C_{1-20}$)alkyl, a ($C_{1-15}$)alkyl, a ($C_{1-10}$)alkyl, a ($C_{1-5}$)alkyl or a ($C_{1-3}$)alkyl. Alternatively, "alkyl," either alone or represented along with another radical, can be a ($C_1$)alkyl, a ($C_2$)alkyl or a ($C_3$)alkyl.

"Alkylene", unless indicated otherwise, means a straight or branched, saturated or unsaturated, aliphatic, divalent radical. ($C_X$)alkylene and ($C_{X-Y}$)alkylene are typically used where X and Y indicate the number of carbon atoms in the chain. For example, ($C_{1-6}$)alkylene includes methylene (—CH$_2$—), ethylene (—CH$_2$CH$_2$—), trimethylene (—CH$_2$CH$_2$CH$_2$—), tetramethylene (—CH$_2$CH$_2$CH$_2$CH$_2$—) 2-butenylene (—CH$_2$CH=CHCH$_2$—), 2-methyltetramethylene (—CH$_2$CH(CH$_3$)CH$_2$CH$_2$—), pentamethylene (—CH$_2$CH$_2$CH$_2$CH$_2$CH$_2$—) and the like. In particular embodiments, "alkylene," either alone or represented along with another radical, can be a ($C_{1-20}$)alkylene, a ($C_{1-15}$)alkylene, a ($C_{1-10}$)alkylene, a ($C_{1-5}$)alkylene or a ($C_{1-3}$)alkylene. Alternatively, "alkylene," either alone or represented along with another radical, can be a ($C_1$)alkylene, a ($C_2$)alkylene or a ($C_3$)alkylene.

"Alkylidene" means a straight or branched, saturated or unsaturated, aliphatic radical connected to the parent molecule by a double bond. ($C_X$)alkylidene and ($C_{X-Y}$)alkylidene are typically used where X and Y indicate the number of carbon atoms in the chain. For example, ($C_{1-6}$)alkylidene includes methylene (=CH$_2$), ethylidene (=CHCH$_3$), isopropylidene (=C(CH$_3$)$_2$), propylidene (=CHCH$_2$CH$_3$), allylidene (=CH—CH=CH$_2$), and the like. In particular embodiments, "alkylidene," either alone or represented along with another radical, can be a (C$_{1-20}$)alkylidene, a (C$_{1-15}$)alkylidene, a (C$_{1-10}$)alkylidene, a (C$_{1-5}$)alkylidene or a (C$_{1-3}$)alkylidene. Alternatively, "alkylidene," either alone or represented along with another radical, can be a (C$_1$)alkylidene, a (C$_2$)alkylidene or a (C$_3$)alkylidene.

"Alkynyl" means a straight or branched, carbon chain that contains at least one carbon-carbon triple bond (—C≡C— or —C≡CR, wherein R is hydrogen or a further substituent). Examples of alkynyl include ethynyl, propargyl, 3-methyl-1-pentynyl, 2-heptynyl and the like. In particular embodiments, "alkynyl," either alone or represented along with another radical, can be a (C$_{2-20}$)alkynyl, a (C$_{2-15}$)alkynyl, a (C$_{2-10}$) alkynyl, a (C$_{2-5}$)alkynyl or a (C$_{2-3}$)alkynyl. Alternatively, "alkynyl," either alone or represented along with another radical, can be a (C$_2$)alkynyl, a (C$_3$)alkynyl or a (C$_4$)alkynyl.

"Alkynylene" means a straight or branched, divalent carbon chain having one or more carbon-carbon triple bonds (—CR≡CR'—, wherein R and R' are each independently hydrogen or further substituents). Examples of alkynylene include ethyne-1,2-diyl, propyne-1,3-diyl, and the like. In particular embodiments, "alkynylene," either alone or represented along with another radical, can be a (C$_{2-20}$) alkynylene, a (C$_{2-15}$) alkynylene, a (C$_{2-10}$) alkynylene, a (C$_{2-5}$) alkynylene or a (C$_{2-3}$) alkynylene. Alternatively, "alkynylene," either alone or represented along with another radical, can be a (C$_2$) alkynylene, a (C$_3$) alkynylene or a (C$_4$) alkynylene.

"Amido" means the radical —C(=O)—NR—, —C(=O)—NRR', —NR—C(=O)— and/or —NR—C(=O)R', wherein each R and R' are independently hydrogen or a further substituent.

"Amino" means a nitrogen moiety having two further substituents where, for example, a hydrogen or carbon atom is attached to the nitrogen. For example, representative amino groups include —NH$_2$, —NHCH$_3$, —N(CH$_3$)$_2$, —NH((C$_{1-10}$)alkyl), —N((C$_{1-10}$)alkyl)$_2$, —NH(aryl), —NH(heteroaryl), —N(aryl)$_2$, —N(heteroaryl)$_2$, and the like. Optionally, the two substituents together with the nitrogen may also form a ring. Unless indicated otherwise, the compounds of the invention containing amino moieties may include protected derivatives thereof. Suitable protecting groups for amino moieties include acetyl, tert-butoxycarbonyl, benzyloxycarbonyl, and the like.

"Animal" includes humans, non-human mammals (e.g., dogs, cats, rabbits, cattle, horses, sheep, goats, swine, deer, and the like) and non-mammals (e.g., birds, and the like).

"Aromatic" means a moiety wherein the constituent atoms make up an unsaturated ring system, all atoms in the ring system are sp$^2$ hybridized and the total number of pi electrons is equal to 4n+2. An aromatic ring may be such that the ring atoms are only carbon atoms or may include carbon and non-carbon atoms (See "heteroaryl").

"Aryl" means a monocyclic or polycyclic ring assembly wherein each ring is aromatic or when fused with one or more rings forms an aromatic ring assembly. If one or more ring atoms is not carbon (e.g., N, S), the aryl is a heteroaryl. (C$_X$)aryl and (C$_{X-Y}$)aryl are typically used where X and Y indicate the number of carbon atoms in the ring. In particular embodiments, "aryl," either alone or represented along with another radical, can be a (C$_{3-14}$)aryl, a (C$_{3-10}$)aryl, a (C$_{3-7}$)aryl, a (C$_{8-10}$)aryl or a (C$_{5-7}$)aryl. Alternatively, "aryl," either alone or represented along with another radical, can be a (C$_5$)aryl, a (C$_6$)aryl, a (C$_7$)aryl, a (C$_8$)aryl, a (C$_9$)aryl or a (C$_{10}$)aryl.

"Azaalkyl" means an alkyl, as defined above, except where one or more of the carbon atoms forming the alkyl chain are replaced with substituted or unsubstituted nitrogen atoms (—NR— or —NRR', wherein R and R' are each independently hydrogen or further substituents). For example, a (C$_{1-10}$)azaalkyl refers to a chain comprising between 1 and 10 carbons and one or more nitrogen atoms.

"Bicycloalkyl" means a saturated or partially unsaturated fused, spiro or bridged bicyclic ring assembly. In particular embodiments, "bicycloalkyl," either alone or represented along with another radical, can be a (C$_{4-15}$)bicycloalkyl, a (C$_{4-10}$)bicycloalkyl, a (C$_{6-10}$)bicycloalkyl or a (C$_{8-10}$)bicycloalkyl. Alternatively, "bicycloalkyl," either alone or represented along with another radical, can be a (C$_8$)bicycloalkyl, a (C$_9$)bicycloalkyl or a (C$_{10}$)bicycloalkyl.

"Bicycloaryl" means a fused, spiro or bridged bicyclic ring assembly wherein at least one of the rings comprising the assembly is aromatic. (C$_X$)bicycloaryl and (C$_{X-Y}$)bicycloaryl are typically used where X and Y indicate the number of carbon atoms in the bicyclic ring assembly and directly attached to the ring. In particular embodiments, "bicycloaryl," either alone or represented along with another radical, can be a (a (C$_{4-15}$)bicycloaryl, a (C$_{4-10}$)bicycloaryl, a (C$_{6-10}$)bicycloaryl or a (C$_{8-10}$)bicycloaryl. Alternatively, "bicycloalkyl," either alone or represented along with another radical, can be a (C$_8$)bicycloaryl, a (C$_9$)bicycloaryl or a (C$_{10}$) bicycloaryl.

"Bridging ring" and "bridged ring" as used herein refer to a ring that is bonded to another ring to form a compound having a bicyclic or polycyclic structure where two ring atoms that are common to both rings are not directly bound to each other. Non-exclusive examples of common compounds having a bridging ring include borneol, norbornane, 7-oxabicyclo[2.2.1]heptane, and the like. One or both rings of the bicyclic system may also comprise heteroatoms.

"Carbamoyl" means the radical —OC(O)NRR', wherein R and R' are each independently hydrogen or further substituents.

"Carbocycle" means a ring consisting of carbon atoms.

"Carbonyl" means the radical —C(=O)— and/or —C(=O)R, wherein R is hydrogen or a further substituent. It is noted that the carbonyl radical may be further substituted with a variety of substituents to form different carbonyl groups including acids, acid halides, aldehydes, amides, esters, and ketones.

"Carboxy" means the radical —C(=O)—O— and/or —C(=O)—OR, wherein R is hydrogen or a further substituent. It is noted that compounds of the invention containing carboxy moieties may include protected derivatives thereof, i.e., where the oxygen is substituted with a protecting group. Suitable protecting groups for carboxy moieties include benzyl, tert-butyl, and the like.

"Cyano" means the radical —CN.

"Cycloalkyl" means a non-aromatic, saturated or partially unsaturated, monocyclic, bicyclic or polycyclic ring assembly. (C$_X$)cycloalkyl and (C$_{X-Y}$)cycloalkyl are typically used where X and Y indicate the number of carbon atoms in the ring assembly. For example, (C$_{3-10}$)cycloalkyl includes cyclopropyl, cyclobutyl, cyclopentyl, cyclohexyl, cyclohexenyl, 2,5-cyclohexadienyl, bicyclo[2.2.2]octyl, adamantan-1-yl, decahydronaphthyl, oxocyclohexyl, dioxocyclohexyl, thiocyclohexyl, 2-oxobicyclo[2.2.1]hept-1-yl, and the like. In particular embodiments, "cycloalkyl," either alone or represented along with another radical, can be a (C$_{3-14}$)cycloalkyl, a (C$_{3-10}$)cycloalkyl, a (C$_{3-7}$)cycloalkyl, a (C$_{8-10}$)cycloalkyl or a (C$_{5-7}$)cycloalkyl. Alternatively, "cycloalkyl," either alone or represented along with another radical, can be a (C$_5$)cycloalkyl, a ($C_6$)cycloalkyl, a ($C_7$)cycloalkyl, a ($C_8$)cycloalkyl, a ($C_9$)cycloalkyl or a ($C_{10}$)cycloalkyl.

"Cycloalkylene" means a divalent, saturated or partially unsaturated, monocyclic, bicyclic or polycyclic ring assembly. ($C_X$)cycloalkylene and ($C_{X-Y}$)cycloalkylene are typically used where X and Y indicate the number of carbon atoms in the ring assembly. In particular embodiments, "cycloalkylene," either alone or represented along with another radical, can be a ($C_{3-14}$)cycloalkylene, a ($C_{3-10}$)cycloalkylene, a ($C_{3-7}$)cycloalkylene, a ($C_{8-10}$)cycloalkylene or a ($C_{5-7}$)cycloalkylene. Alternatively, "cycloalkylene," either alone or represented along with another radical, can be a ($C_5$)cycloalkylene, a ($C_6$)cycloalkylene, a ($C_7$)cycloalkylene, a ($C_8$)cycloalkylene, a ($C_9$)cycloalkylene or a ($C_{10}$)cycloalkylene.

"Disease" specifically includes any unhealthy condition of an animal or part thereof and includes an unhealthy condition that may be caused by, or incident to, medical or veterinary therapy applied to that animal, i.e., the "side effects" of such therapy.

"Fused ring" as used herein refers to a ring that is bonded to another ring to form a compound having a bicyclic structure where the ring atoms that are common to both rings are directly bound to each other. Non-exclusive examples of common fused rings include decalin, naphthalene, anthracene, phenanthrene, indole, furan, benzofuran, quinoline, and the like. Compounds having fused ring systems may be saturated, partially saturated, carbocyclics, heterocyclics, aromatics, heteroaromatics, and the like.

"Halo" means fluoro, chloro, bromo or iodo.

"Heteroalkyl" means alkyl, as defined in this Application, provided that one or more of the atoms within the alkyl chain is a heteroatom. In particular embodiments, "heteroalkyl," either alone or represented along with another radical, can be a hetero($C_{1-20}$)alkyl, a hetero($C_{1-15}$)alkyl, a hetero($C_{1-10}$)alkyl, a hetero($C_{1-5}$)alkyl, a hetero($C_{1-3}$)alkyl or a hetero ($C_{1-2}$)alkyl. Alternatively, "heteroalkyl," either alone or represented along with another radical, can be a hetero($C_1$)alkyl, a hetero($C_2$)alkyl or a hetero($C_3$)alkyl.

"Heteroaryl" means a monocyclic, bicyclic or polycyclic aromatic group wherein at least one ring atom is a heteroatom and the remaining ring atoms are carbon. Monocyclic heteroaryl groups include, but are not limited to, cyclic aromatic groups having five or six ring atoms, wherein at least one ring atom is a heteroatom and the remaining ring atoms are carbon. The nitrogen atoms can be optionally quaternerized and the sulfur atoms can be optionally oxidized. Heteroaryl groups of this invention include, but are not limited to, those derived from furan, imidazole, isothiazole, isoxazole, oxadiazole, oxazole, 1,2,3-oxadiazole, pyrazine, pyrazole, pyridazine, pyridine, pyrimidine, pyrroline, thiazole, 1,3,4-thiadiazole, triazole and tetrazole. "Heteroaryl" also includes, but is not limited to, bicyclic or tricyclic rings, wherein the heteroaryl ring is fused to one or two rings independently selected from the group consisting of an aryl ring, a cycloalkyl ring, a cycloalkenyl ring, and another monocyclic heteroaryl or heterocycloalkyl ring. These bicyclic or tricyclic heteroaryls include, but are not limited to, those derived from benzo[b]furan, benzo[b]thiophene, benzimidazole, imidazo[4,5-c]pyridine, quinazoline, thieno[2,3-c]pyridine, thieno[3,2-b]pyridine, thieno[2,3-b]pyridine, indolizine, imidazo[1,2a]pyridine, quinoline, isoquinoline, phthalazine, quinoxaline, naphthyridine, quinolizine, indole, isoindole, indazole, indoline, benzoxazole, benzopyrazole, benzothiazole, imidazo[1,5-a]pyridine, pyrazolo[1,5-a]pyridine, imidazo[1,2-a]pyrimidine, imidazo[1,2-c]pyrimidine, imidazo[1,5-a]pyrimidine, imidazo[1,5-c]pyrimidine, pyrrolo[2,3-b]pyridine, pyrrolo[2,3-c]pyridine, pyrrolo[3,2-c]pyridine, pyrrolo[3,2-b]pyridine, pyrrolo[2,3-d]pyrimidine, pyrrolo[3,2-d]pyrimidine, pyrrolo[2,3-b]pyrazine, pyrazolo[1,5-a]pyridine, pyrrolo[1,2-b]pyridazine, pyrrolo[1,2-c]pyrimidine, pyrrolo[1,2-a]pyrimidine, pyrrolo[1,2-a]pyrazine, triazo[1,5-a]pyridine, pteridine, purine, carbazole, acridine, phenazine, phenothiazene, phenoxazine, 1,2-dihydropyrrolo[3,2,1-hi]indole, indolizine, pyrido[1,2-a]indole and 2(1H)-pyridinone. The bicyclic or tricyclic heteroaryl rings can be attached to the parent molecule through either the heteroaryl group itself or the aryl, cycloalkyl, cycloalkenyl or heterocycloalkyl group to which it is fused. The heteroaryl groups of this invention can be substituted or unsubstituted. In particular embodiments, "heteroaryl," either alone or represented along with another radical, can be a hetero($C_{1-13}$)aryl, a hetero($C_{2-13}$)aryl, a hetero($C_{2-6}$)aryl, a hetero($C_{3-9}$)aryl or a hetero($C_{5-9}$)aryl. Alternatively, "heteroaryl," either alone or represented along with another radical, can be a hetero($C_3$)aryl, a hetero($C_4$)aryl, a hetero($C_5$)aryl, a hetero($C_6$)aryl, a hetero($C_7$)aryl, a hetero($C_8$)aryl or a hetero($C_9$)aryl.

"Heteroatom" refers to an atom that is not a carbon atom. Particular examples of heteroatoms include, but are not limited to, nitrogen, oxygen, and sulfur.

"Heteroatom moiety" includes a moiety where the atom by which the moiety is attached is not a carbon. Examples of heteroatom moieties include —NR—, —N$^+$(O$^-$)=, —O—, —S— or —S(O)$_2$—, wherein R is hydrogen or a further substituent.

"Heterobicycloalkyl" means bicycloalkyl, as defined in this Application, provided that one or more of the atoms within the ring is a heteroatom. For example hetero($C_{9-12}$) bicycloalkyl as used in this application includes, but is not limited to, 3-aza-bicyclo[4.1.0]hept-3-yl, 2-aza-bicyclo[3.1.0]hex-2-yl, 3-aza-bicyclo[3.1.0]hex-3-yl, and the like. In particular embodiments, "heterobicycloalkyl," either alone or represented along with another radical, can be a hetero($C_{1-14}$)bicycloalkyl, a hetero($C_{4-14}$)bicycloalkyl, a hetero($C_{4-9}$)bicycloalkyl or a hetero($C_{5-9}$)bicycloalkyl. Alternatively, "heterobicycloalkyl," either alone or represented along with another radical, can be a hetero($C_5$)bicycloalkyl, hetero($C_6$)bicycloalkyl, hetero($C_7$)bicycloalkyl, hetero($C_8$)bicycloalkyl or a hetero($C_9$)bicycloalkyl.

"Heterobicycloaryl" means bicycloaryl, as defined in this Application, provided that one or more of the atoms within the ring is a heteroatom. For example, hetero($C_{4-12}$)bicycloaryl as used in this Application includes, but is not limited to, 2-amino-4-oxo-3,4-dihydropteridin-6-yl, tetrahydroisoquinolinyl, and the like. In particular embodiments, "heterobicycloaryl," either alone or represented along with another radical, can be a hetero($C_{1-4}$)bicycloaryl, a hetero($C_{4-14}$)bicycloaryl, a hetero($C_{4-9}$)bicycloaryl or a hetero($C_{5-9}$)bicycloaryl. Alternatively, "heterobicycloaryl," either alone or represented along with another radical, can be a hetero($C_5$)bicycloaryl, hetero($C_6$)bicycloaryl, hetero($C_7$)bicycloaryl, hetero($C_8$)bicycloaryl or a hetero($C_9$)bicycloaryl.

"Heterocycloalkyl" means cycloalkyl, as defined in this Application, provided that one or more of the atoms forming the ring is a heteroatom selected, independently from N, O, or S. Non-exclusive examples of heterocycloalkyl include piperidyl, 4-morpholyl, 4-piperazinyl, pyrrolidinyl, perhydropyrrolizinyl, 1,4-diazaperhydroepinyl, 1,3-dioxanyl, 1,4-dioxanyl and the like. In particular embodiments, "heterocycloalkyl," either alone or represented along with another radical, can be a hetero($C_{1-13}$)cycloalkyl, a hetero($C_{1-9}$)cycloalkyl, a hetero($C_{1-6}$)cycloalkyl, a hetero($C_{5-9}$)cycloalkyl or a hetero($C_{2-6}$)cycloalkyl. Alternatively, "heterocycloalkyl," either alone or represented along with another radical, can be a hetero($C_2$)cycloalkyl, a hetero($C_3$)cycloalkyl, a hetero($C_4$)cycloalkyl, a hetero($C_5$)cycloalkyl, a hetero($C_6$)cycloalkyl, hetero($C_7$)cycloalkyl, hetero($C_8$)cycloalkyl or a hetero($C_9$)cycloalkyl.

"Heterocycloalkylene" means cycloalkylene, as defined in this Application, provided that one or more of the ring member carbon atoms is replaced by a heteroatom. In particular embodiments, "heterocycloalkylene," either alone or represented along with another radical, can be a hetero($C_{1-13}$)cycloalkylene, a hetero($C_{1-9}$)cycloalkylene, a hetero($C_{1-6}$)cycloalkylene, a hetero($C_{5-9}$)cycloalkylene or a hetero($C_{2-6}$)cycloalkylene. Alternatively, "heterocycloalkylene," either alone or represented along with another radical, can be a hetero($C_2$)cycloalkylene, a hetero($C_3$)cycloalkylene, a hetero($C_4$)cycloalkylene, a hetero($C_5$)cycloalkylene, a hetero($C_6$)cycloalkylene, hetero($C_7$)cycloalkylene, hetero($C_8$)cycloalkylene or a hetero($C_9$)cycloalkylene.

"Hydroxy" means the radical —OH.

"$IC_{50}$" means the molar concentration of an inhibitor that produces 50% inhibition of the target enzyme.

"Imino" means the radical —CR(=NR') and/or —C(=NR')—, wherein R and R' are each independently hydrogen or a further substituent.

"Isomers" means compounds having identical molecular formulae but differing in the nature or sequence of bonding of their atoms or in the arrangement of their atoms in space. Isomers that differ in the arrangement of their atoms in space are termed "stereoisomers." Stereoisomers that are not mirror images of one another are termed "diastereomers" and stereoisomers that are nonsuperimposable mirror images are termed "enantiomers" or sometimes "optical isomers." A carbon atom bonded to four nonidentical substituents is termed a "chiral center." A compound with one chiral center has two enantiomeric forms of opposite chirality. A mixture of the two enantiomeric forms is termed a "racemic mixture." A compound that has more than one chiral center has $2^{n-1}$ enantiomeric pairs, where n is the number of chiral centers. Compounds with more than one chiral center may exist as ether an individual diastereomer or as a mixture of diastereomers, termed a "diastereomeric mixture." When one chiral center is present a stereoisomer may be characterized by the absolute configuration of that chiral center. Absolute configuration refers to the arrangement in space of the substituents attached to the chiral center. Enantiomers are characterized by the absolute configuration of their chiral centers and described by the R- and S-sequencing rules of Cahn, Ingold and Prelog. Conventions for stereochemical nomenclature, methods for the determination of stereochemistry and the separation of stereoisomers are well known in the art (e.g., see "Advanced Organic Chemistry", 4th edition, March, Jerry, John Wiley & Sons, New York, 1992).

"Leaving group" means the group with the meaning conventionally associated with it in synthetic organic chemistry, i.e., an atom or group displaceable under reaction (e.g., alkylating) conditions. Examples of leaving groups include, but are not limited to, halo (e.g., F, Cl, Br and I), alkyl (e.g., methyl and ethyl) and sulfonyloxy (e.g., mesyloxy, ethanesulfonyloxy, benzenesulfonyloxy and tosyloxy), thiomethyl, thienyloxy, dihalophosphinoyloxy, tetrahalophosphoxy, benzyloxy, isopropyloxy, acyloxy, and the like.

"Moiety providing X atom separation" and "linker providing X atom separation" between two other moieties mean that the chain of atoms directly linking the two other moieties is X atoms in length. When X is given as a range (e.g., $X_1$-$X_2$), then the chain of atoms is at least $X_1$ and not more than $X_2$ atoms in length. It is understood that the chain of atoms can be formed from a combination of atoms including, for example, carbon, nitrogen, sulfur and oxygen atoms. Further, each atom can optionally be bound to one or more substituents, as valencies allow. In addition, the chain of atoms can form part of a ring. Accordingly, in one embodiment, a moiety providing X atom separation between two other moieties (R and R') can be represented by R-$(L)_X$-R' where each L is independently selected from the group consisting of CR"R'", NR"", O, S, CO, CS, C=NR"", SO, $SO_2$, and the like, where any two or more of R", R'", R"" and R"" can be taken together to form a substituted or unsubstituted ring.

"Nitro" means the radical —$NO_2$.

"Oxaalkyl" means an alkyl, as defined above, except where one or more of the carbon atoms forming the alkyl chain are replaced with oxygen atoms (—O— or —OR, wherein R is hydrogen or a further substituent). For example, an oxa($C_{1-10}$)alkyl refers to a chain comprising between 1 and 10 carbons and one or more oxygen atoms.

"Oxoalkyl" means an alkyl, as defined above, except where one or more of the carbon atoms forming the alkyl chain are replaced with carbonyl groups (—C(=O)— or —C(=O)—R, wherein R is hydrogen or a further substituent). The carbonyl group may be an aldehyde, ketone, ester, amide, acid or acid halide. For example, an oxo($C_{1-10}$)alkyl refers to a chain comprising between 1 and 10 carbon atoms and one or more carbonyl groups.

"Oxy" means the radical —O— or —OR, wherein R is hydrogen or a further substituent. Accordingly, it is noted that the oxy radical may be further substituted with a variety of substituents to form different oxy groups including hydroxy, alkoxy, aryloxy, heteroaryloxy or carbonyloxy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid and the like.

Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like.

"Polycyclic ring" includes bicyclic and multi-cyclic rings. The individual rings comprising the polycyclic ring can be fused, spiro or bridging rings.

"Prodrug" means a compound that is convertible in vivo metabolically into an inhibitor according to the present invention. The prodrug itself may or may not also have activity with respect to a given target protein. For example, a compound comprising a hydroxy group may be administered as an ester that is converted by hydrolysis in vivo to the hydroxy compound. Suitable esters that may be converted in vivo into hydroxy compounds include acetates, citrates, lactates, phosphates, tartrates, malonates, oxalates, salicylates, propionates, succinates, fumarates, maleates, methylene-bis-b-hydroxynaphthoates, gentisates, isethionates, di-p-toluoyltartrates, methanesulfonates, ethanesulfonates, benzenesulfonates, p-toluenesulfonates, cyclohexylsulfamates, quinates, esters of amino acids, and the like. Similarly, a compound comprising an amine group may be administered as an amide that is converted by hydrolysis in vivo to the amine compound.

"Protected derivatives" means derivatives of inhibitors in which a reactive site or sites are blocked with protecting groups. Protected derivatives are useful in the preparation of inhibitors or in themselves may be active as inhibitors. A comprehensive list of suitable protecting groups can be found in T. W. Greene, *Protecting Groups in Organic Synthesis,* 3rd edition, John Wiley & Sons, Inc. 1999.

"Ring" and "ring assembly" means a carbocyclic or a heterocyclic system and includes aromatic and non-aromatic systems. The system can be monocyclic, bicyclic or polycyclic. In addition, for bicyclic and polycyclic systems, the individual rings comprising the polycyclic ring can be fused, spiro or bridging rings.

"Subject" and "patient" includes humans, non-human mammals (e.g., dogs, cats, rabbits, cattle, horses, sheep, goats, swine, deer, and the like) and non-mammals (e.g., birds, and the like).

"Substituent convertible to hydrogen in vivo" means any group that is convertible to a hydrogen atom by enzymological or chemical means including, but not limited to, hydrolysis and hydrogenolysis. Examples include hydrolyzable groups, such as acyl groups, groups having an oxycarbonyl group, amino acid residues, peptide residues, o-nitrophenylsulfenyl, trimethylsilyl, tetrahydro-pyranyl, diphenylphosphinyl, and the like. Examples of acyl groups include formyl, acetyl, trifluoroacetyl, and the like. Examples of groups having an oxycarbonyl group include ethoxycarbonyl, t-butoxycarbonyl[$(CH_3)_3$C—OCO—], benzyloxycarbonyl, p-methoxybenzyloxycarbonyl, vinyloxycarbonyl, β-(p-toluenesulfonyl)ethoxycarbonyl, and the like. Examples of suitable amino acid residues include amino acid residues per se and amino acid residues that are protected with a protecting group. Suitable amino acid residues include, but are not limited to, residues of Gly (glycine), Ala (alanine; $CH_3CH(NH_2)CO$—), Arg (arginine), Asn (asparagine), Asp (aspartic acid), Cys (cysteine), Glu (glutamic acid), His (histidine), Ile (isoleucine), Leu (leucine; $(CH_3)_2CHCH_2CH(NH_2)CO$—), Lys (lysine), Met (methionine), Phe (phenylalanine), Pro (proline), Ser (serine), Thr (threonine), Trp (tryptophan), Tyr (tyrosine), Val (valine), Nva (norvaline), Hse (homoserine), 4-Hyp (4-hydroxyproline), 5-Hyl (5-hydroxylysine), Orn (ornithine) and β-Ala. Examples of suitable protecting groups include those typically employed in peptide synthesis, including acyl groups (such as formyl and acetyl), arylmethyloxycarbonyl groups (such as benzyloxycarbonyl and p-nitrobenzyloxycarbonyl), t-butoxycarbonyl groups [$(CH_3)_3$C—OCO—], and the like. Suitable peptide residues include peptide residues comprising two to five, and optionally two to three, of the aforesaid amino acid residues. Examples of such peptide residues include, but are not limited to, residues of such peptides as Ala-Ala[$CH_3CH(NH_2)CO$—$NHCH(CH_3)CO$—], Gly-Phe, Nva-Nva, Ala-Phe, Gly-Gly, Gly-Gly-Gly, Ala-Met, Met-Met, Leu-Met and Ala-Leu. The residues of these amino acids or peptides can be present in stereochemical configurations of the D-form, the L-form or mixtures thereof. In addition, the amino acid or peptide residue may have an asymmetric carbon atom. Examples of suitable amino acid residues having an asymmetric carbon atom include residues of Ala, Leu, Phe, Trp, Nva, Val, Met, Ser, Lys, Thr and Tyr. Peptide residues having an asymmetric carbon atom include peptide residues having one or more constituent amino acid residues having an asymmetric carbon atom. Examples of suitable amino acid protecting groups include those typically employed in peptide synthesis, including acyl groups (such as formyl and acetyl), arylmethyloxycarbonyl groups (such as benzyloxycarbonyl and p-nitrobenzyloxycarbonyl), t-butoxycarbonyl groups [$(CH_3)_3$C—OCO—], and the like. Other examples of substituents "convertible to hydrogen in vivo" include reductively eliminable hydrogenolyzable groups. Examples of suitable reductively eliminable hydrogenolyzable groups include, but are not limited to, arylsulfonyl groups (such as o-toluenesulfonyl); methyl groups substituted with phenyl or benzyloxy (such as benzyl, trityl and benzyloxymethyl); arylmethoxycarbonyl groups (such as benzyloxycarbonyl and o-methoxybenzyloxycarbonyl); and halogenoethoxycarbonyl groups (such as β,β,β-trichloroethoxycarbonyl and O-iodoethoxycarbonyl).

"Substituted or unsubstituted" means that a given moiety may consist of only hydrogen substituents through available valencies (unsubstituted) or may further comprise one or more non-hydrogen substituents through available valencies (substituted) that are not otherwise specified by the name of the given moiety. For example, isopropyl is an example of an ethylene moiety that is substituted by —$CH_3$. In general, a non-hydrogen substituent may be any substituent that may be bound to an atom of the given moiety that is specified to be substituted. Examples of substituents include, but are not limited to, aldehyde, alicyclic, aliphatic, $(C_{1-10})$alkyl, alkylene, alkylidene, amide, amino, aminoalkyl, aromatic, aryl, bicycloalkyl, bicycloaryl, carbamoyl, carbocyclyl, carboxyl, carbonyl group, cycloalkyl, cycloalkylene, ester, halo, heterobicycloalkyl, heterocycloalkylene, heteroaryl, heterobicycloaryl, heterocycloalkyl, oxo, hydroxy, iminoketone, ketone, nitro, oxaalkyl, and oxoalkyl moieties, each of which may optionally also be substituted or unsubstituted. In one particular embodiment, examples of substituents include, but are not limited to, hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl. In addition, the substituent is itself optionally substituted by a further substituent. In one particular embodiment, examples of the further substituent include, but are not limited to, hydrogen, halo, nitro, cyano, thio, oxy, hydroxy, carbonyloxy, $(C_{1-10})$alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, (C$_{1-10}$)alkyl, halo(C$_{1-10}$) alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl (C$_{1-10}$)alkyl, (C$_{1-10}$)azaalkyl, imino(C$_{1-10}$)alkyl, (C$_{3-12}$)cycloalkyl(C$_{1-5}$)alkyl, hetero(C$_{3-12}$)cycloalkyl(C$_{1-10}$)alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero (C$_{1-10}$)aryl, (C$_{9-12}$)bicycloaryl and hetero(C$_{4-12}$)bicycloaryl.

"Sulfinyl" means the radical —SO— and/or —SO—R, wherein R is hydrogen or a further substituent. It is noted that the sulfinyl radical may be further substituted with a variety of substituents to form different sulfinyl groups including sulfinic acids, sulfinamides, sulfinyl esters, and sulfoxides.

"Sulfonyl" means the radical —SO$_2$— and/or —SO$_2$—R, wherein R is hydrogen or a further substituent. It is noted that the sulfonyl radical may be further substituted with a variety of substituents to form different sulfonyl groups including sulfonic acids, sulfonamides, sulfonate esters, and sulfones.

"Therapeutically effective amount" means that amount which, when administered to an animal for treating a disease, is sufficient to effect such treatment for the disease.

"Thio" denotes replacement of an oxygen by a sulfur and includes, but is not limited to, —SR, —S— and =S containing groups.

"Thioalkyl" means an alkyl, as defined above, except where one or more of the carbon atoms forming the alkyl chain are replaced with sulfur atoms (—S— or —S—R, wherein R is hydrogen or a further substituent). For example, a thio(C$_{1-10}$)alkyl refers to a chain comprising between 1 and 10 carbons and one or more sulfur atoms.

"Thiocarbonyl" means the radical —C(=S)— and/or —C(=S)—R, wherein R is hydrogen or a further substituent. It is noted that the thiocarbonyl radical may be further substituted with a variety of substituents to form different thiocarbonyl groups including thioacids, thioamides, thioesters, and thioketones.

"Treatment" or "treating" means any administration of a compound of the present invention and includes:

(1) preventing the disease from occurring in an animal which may be predisposed to the disease but does not yet experience or display the pathology or symptomatology of the disease, (2) inhibiting the disease in an animal that is experiencing or displaying the pathology or symptomatology of the diseased (i.e., arresting further development of the pathology and/or symptomatology), or (3) ameliorating the disease in an animal that is experiencing or displaying the pathology or symptomatology of the diseased (i.e., reversing the pathology and/or symptomatology).

It is noted in regard to all of the definitions provided herein that the definitions should be interpreted as being open ended in the sense that further substituents beyond those specified may be included. Hence, a C$_1$ alkyl indicates that there is one carbon atom but does not indicate what are the substituents on the carbon atom. Hence, a (C$_1$)alkyl comprises methyl (i.e., —CH$_3$) as well as —CRR'R" where R, R', and R" may each independently be hydrogen or a further substituent where the atom attached to the carbon is a heteroatom or cyano. Hence, CF$_3$, CH$_2$OH and CH$_2$CN, for example, are all (C$_1$)alkyls. Similarly, terms such as alkylamino and the like comprise dialkylamino and the like.

A compound having a formula that is represented with a dashed bond is intended to include the formulae optionally having zero, one or more double bonds, as exemplified and shown below:

represents

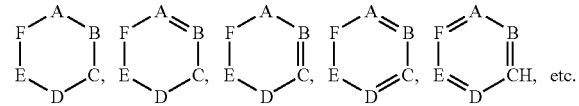

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}$C and $^{14}$C.

DETAILED DESCRIPTION OF THE INVENTION

The present invention relates to compounds that may be used to inhibit Mitogen-Activated Protein Kinases (referred to herein as MEK) and, in particular, MAPK/ERK Kinase 1 (referred to herein as MEK1) and/or MAPK/ERK Kinase 2 (referred to herein as MEK2). The present invention also relates to pharmaceutical compositions, kits and articles of manufacture comprising such compounds. In addition, the present invention relates to methods and intermediates useful for making the compounds. Further, the present invention relates to methods of using said compounds. It is noted that the compounds of the present invention may also possess activity for other members of the same protein family and thus may be used to address disease states associated with these other family members.

MEK belongs to the protein kinase family of enzymes. The mitogen-activated protein kinase (MAPK) pathways are evolutionarily conserved from yeast to man and respond to a variety of extracellular signals to induce cell differentiation and proliferation. The extracellular-regulated kinase (ERK) cascade is one of three major MAPK signaling pathways and is the predominant cascade that controls cell proliferation, migration, division, and differentiation (Schaeffer, H. J., and Weber, M. J. (1999) *Mol. Cell. Biol.* 19, 2435-2444). In this pathway, binding of GTP to the Ras protein initiates a three protein kinase cascade, which leads to ERK activation through the intervening protein kinases Raf-1 and MEK1/2. The MEK1/2 kinases are dual-specificity threonine/tyrosine kinases that activate the downstream ERK kinase by phosphorylating specific ERK threonine and tyrosine residues, and are themselves activated by phosphorylation of MEK serine residues by the upstream RAF kinase. MEK1 and MEK2 share a high degree of amino acid sequence similarity, particularly in their kinase domains, and both are capable of phosphorylating ERK (Zheng, C-F., and Guan, K. (1993) *J. Biol. Chem.* 268, 11435-11439).

Multiple studies have linked the RAF/MEK/ERK signaling pathway to the growth and survival of many diverse human tumors including, but not limited to cancers of the colon, pancreas ovaries, and non-small-cell lung cancers (reviewed in: Sebolt-Leopold, J. S. and Herrera R. (2004) *Nature Reviews: Cancer,* 4, 937-947). For these reasons there has been considerable interest in developing small molecule pharmaceutical inhibitors of this pathway.

It is noted that the compounds of the present invention may also possess inhibitory activity for other protein kinase family members and thus may be used to address disease states associated with these other family members.

Crystal Structure of MEK2

Takeda San Diego, Inc. solved the crystal structure of MEK2. Knowledge of the crystal structure was used to guide the design of the inhibitors provided herein.

The overall architecture of the MEK proteins resembles the conserved, two domain protein kinase fold, consisting of a large C-terminal comprised mostly of an α-helical domain and a smaller N-terminal lobe comprised primarily of a β-sheet. The N-lobe typically contains a single α-helix termed the Control or C-helix which influences the productive binding of nucleotides at the active region, which is located at the cleft between the two domains. Additionally, productive binding of nucleotide and substrates can be dependent upon an Activation Loop, or A-Loop, which is in an extended conformation when active, but often in a folded-back inactive conformation that at least partially occludes the active region. Phosphorylation of specific residues within the A-Loop can help stabilise the active, extended conformation. Common kinase inhibitory mechanisms typically target structural alterations within the C-Helix or A Loop.

MEK1 and/or MEK2 Inhibitors and Processes for Making Thereof

In one of its aspects, the present invention relates to MEK inhibitors. In one embodiment, MEK inhibitors of the present invention have the formula:

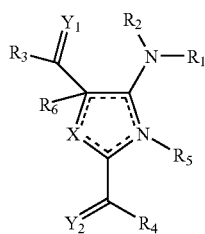

or a polymorph, solvate, ester, tautomer, enantiomer, pharmaceutically acceptable salt or prodrug thereof, wherein X is selected from the group consisting of —CR$_7$R$_8$—, —NR$_9$—, —O— and —S—;

Y$_1$ and Y$_2$ are each independently selected from the group consisting of O, S and NR$_{10}$;

R$_1$ is selected from the group consisting of (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted;

R$_2$ is hydrogen or a substituent convertible in vivo to hydrogen;

R$_3$ is selected from the group consisting of hydroxy, amino, (C$_{1-10}$)alkylamino, (C$_{1-10}$)alkoxyamino, hydroxy (C$_{1-10}$)alkoxyamino, hydroxy(C$_{1-10}$)alkylamino, cycloamino, sulfonamido, imino, (C$_{2-10}$)alkyl, halo (C$_{1-10}$)alkyl, carbonyl(C$_{1-3}$)alkyl, thiocarbonyl(C$_{1-3}$) alkyl, sulfonyl(C$_{1-3}$)alkyl, sulfinyl(C$_{1-3}$)alkyl, amino (C$_{1-10}$)alkyl, imino(C$_{1-3}$)alkyl, (C$_{3-12}$)cycloalkyl(C$_{1-5}$) alkyl, hetero(C$_{3-12}$)cycloalkyl(C$_{1-5}$)alkyl, aryl(C$_{1-10}$) alkyl, heteroaryl(C$_{1-5}$)alkyl, (C$_{9-12}$)bicycloaryl(C$_{1-5}$) alkyl, hetero(C$_{8-12}$)bicycloaryl(C$_{1-5}$)alkyl, (C$_{3-12}$) cycloalkyl, hetero(C$_{3-12}$)cycloalkyl, (C$_{9-12}$) bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$) bicycloaryl, each substituted or unsubstituted;

R$_4$ is selected from the group consisting of hydrogen, (C$_{1-10}$)alkoxy, (C$_{4-12}$)aryloxy, amino, (C$_{1-10}$)alkylamino, sulfonamido, imino, sulfonyl, sulfinyl, (C$_{1-10}$) alkyl, halo(C$_{1-10}$)alkyl, hydroxy(C$_{1-10}$)alkyl, carbonyl (C$_{1-10}$)alkyl, thiocarbonyl(C$_{1-10}$)alkyl, sulfonyl(C$_{1-10}$) alkyl, sulfinyl(C$_{1-10}$)alkyl, (C$_{1-10}$)azaalkyl, imino (C$_{1-10}$)alkyl, (C$_{3-12}$)cycloalkyl(C$_{1-5}$)alkyl, hetero (C$_{3-12}$)cycloalkyl(C$_{1-10}$)alkyl, aryl(C$_{1-10}$)alkyl, hetero (C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero (C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted;

R$_5$ is selected from the group consisting of hydrogen, (C$_{1-10}$)alkyl, halo(C$_{1-10}$)alkyl, amino (C$_{1-10}$)alkyl, imino(C$_{1-3}$)alkyl, (C$_{3-12}$)cycloalkyl(C$_{1-5}$)alkyl, hetero (C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero (C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted, or R$_5$ and R$_4$ are taken together to form a substituted or unsubstituted ring;

R$_6$ is selected from the group consisting of hydrogen, heteroaryloxy, amino, (C$_{1-10}$)alkylamino, (C$_{1-10}$)alkyl, halo(C$_{1-10}$)alkyl, sulfonyl(C$_{1-3}$)alkyl, sulfinyl(C$_{1-3}$) alkyl, amino(C$_{1-10}$)alkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{4-12}$)aryl and hetero(C$_{1-10}$)aryl, each substituted or unsubstituted, provided that R$_6$ is absent when the atom to which it is bound forms part of a double bond;

R$_7$ and R$_8$ are each independently selected from the group consisting of hydrogen, halo, nitro, cyano, thio, oxy, hydroxy, carbonyloxy, (C$_{1-10}$)alkoxy, (C$_{4-12}$)aryloxy, hetero(C$_{1-10}$)aryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$)alkyl, hydroxy(C$_{1-10}$)alkyl, carbonyl(C$_{1-10}$)alkyl, thiocarbonyl(C$_{1-10}$)alkyl, sulfonyl(C$_{1-10}$)alkyl, sulfinyl(C$_{1-10}$) alkyl, (C$_{1-10}$)azaalkyl, imino(C$_{1-10}$)alkyl, (C$_{3-12}$)cycloalkyl(C$_{1-5}$)alkyl, hetero(C$_{3-12}$)cycloalkyl(C$_{1-10}$) alkyl, aryl(C$_{1-10}$)alkyl, hetero(C$_{1-10}$)aryl(C$_{1-5}$)alkyl, (C$_{9-12}$)bicycloaryl(C$_{1-5}$)alkyl, hetero(C$_{8-12}$)bicycloaryl (C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$) aryl, hetero(C$_{1-10}$)aryl, (C$_{9-12}$)bicycloaryl and hetero (C$_{4-12}$)bicycloaryl, each substituted or unsubstituted, or R$_7$ and R$_3$ or R$_4$ are taken together to form a substituted or unsubstituted ring, provided that R$_8$ is absent when the atom to which it is bound forms part of a double bond;

R$_9$ is selected from the group consisting of hydrogen, (C$_{1-10}$)alkylamino, sulfonamido, imino, (C$_{1-10}$)alkyl, halo(C$_{1-10}$)alkyl, hydroxy(C$_{1-10}$)alkyl, carbonyl(C$_{1-10}$) alkyl, sulfonyl(C$_{1-10}$)alkyl, sulfinyl(C$_{1-10}$)alkyl, (C$_{1-10}$) azaalkyl, imino(C$_{1-10}$)alkyl, (C$_{3-12}$)cycloalkyl(C$_{1-5}$) alkyl, hetero(C$_{3-12}$)cycloalkyl(C$_{1-10}$)alkyl, aryl(C$_{1-10}$) alkyl, hetero(C$_{1-10}$)aryl(C$_{1-5}$)alkyl, (C$_{9-12}$)bicycloaryl (C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero (C$_{1-10}$)aryl, (C$_{9-12}$)bicycloaryl and hetero(C$_{4-12}$)

bicycloaryl, each substituted or unsubstituted, or R$_9$ and R$_3$ or R$_4$ are taken together to form a substituted or unsubstituted ring, provided that R$_9$ is absent when the atom to which it is bound forms part of a double bond; and R$_{10}$ is selected from the group consisting of hydrogen, (C$_{1-10}$)alkyl, halo(C$_{1-10}$)alkyl, hydroxy(C$_{1-10}$)alkyl, imino(C$_{1-10}$)alkyl, (C$_{3-12}$)cycloalkyl(C$_{1-5}$)alkyl, hetero (C$_{3-12}$)cycloalkyl(C$_{1-10}$)alkyl, aryl(C$_{1-10}$)alkyl, hetero (C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero (C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted, or R$_{10}$ and R$_3$ or R$_4$ are taken together to form a substituted or unsubstituted ring.

In one variation of the above embodiment, Y$_1$ is not S when X is —C(NH$_2$)=, Y$_2$ is O, R$_2$ is H, R$_3$ is —NH-Ph, R$_5$ is H and R$_6$ is H. In another variation of each of the above embodiment and variation, R$_3$ is not —OEt when X is —CH=, Y$_1$ is O, Y$_2$ is O, R$_2$ is H, R$_4$ is unsubstituted phenyl, R$_5$ is H and R$_6$ is H. In still another variation of each of the above embodiment and variations, X is not —C(CO—OMe)= when Y$_1$ is O, Y$_2$ is O, R$_2$ is H, R$_3$ is —OMe, R$_4$ is —OMe and R$_6$ is —CO—OMe.

In another embodiment, MEK inhibitors f the present invention have the formula:

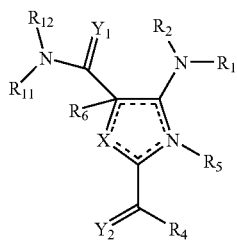

or a polymorph, solvate, ester, tautomer, enantiomer, pharmaceutically acceptable salt or prodrug thereof, wherein R$_{11}$ is hydrogen, a substituent convertible in vivo to hydrogen, a substituted or unsubstituted (C$_{1-10}$)alkyl, or a substituted or unsubstituted halo(C$_{1-10}$)alkyl; and R$_{12}$ is selected from the group consisting of hydrogen, oxy, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo(C$_{1-10}$)alkyl, carbonyl (C$_{1-3}$)alkyl, thiocarbonyl(C$_{1-3}$)alkyl, sulfonyl(C$_{1-3}$) alkyl, sulfinyl(C$_{1-3}$)alkyl, amino (C$_{1-10}$)alkyl, imino (C$_{1-3}$)alkyl, (C$_{3-12}$)cycloalkyl(C$_{1-5}$)alkyl, hetero(C$_{3-12}$) cycloalkyl(C$_{1-5}$)alkyl, aryl(C$_{1-10}$)alkyl, heteroaryl (C$_{1-5}$)alkyl, (C$_{9-12}$)bicycloaryl(C$_{1-5}$)alkyl, hetero (C$_{8-12}$)bicycloaryl(C$_{1-5}$)alkyl, (C$_{3-12}$)cycloalkyl, hetero (C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted, or R$_{11}$ and R$_{12}$ are taken together to form a substituted or unsubstituted ring.

In still another embodiment, MEK inhibitors of the present invention have the formula:

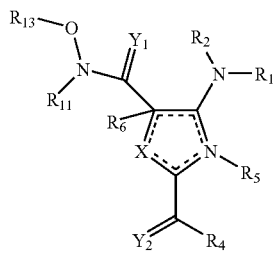

or a polymorph, solvate, ester, tautomer, enantiomer, pharmaceutically acceptable salt or prodrug thereof, wherein R$_{11}$ is hydrogen, a substituent convertible in vivo to hydrogen, a substituted or unsubstituted (C$_{1-10}$)alkyl, or a substituted or unsubstituted halo(C$_{1-10}$)alkyl; and R$_{13}$ is selected from the group consisting of hydrogen, (C$_{1-10}$)alkyl, halo(C$_{1-10}$)alkyl, carbonyl(C$_{1-3}$)alkyl, thiocarbonyl(C$_{1-3}$)alkyl, sulfonyl(C$_{1-3}$)alkyl, sulfinyl (C$_{1-3}$)alkyl, amino(C$_{1-10}$)alkyl, imino(C$_{1-3}$)alkyl, (C$_{3-12}$)cycloalkyl(C$_{1-5}$)alkyl, hetero(C$_{3-12}$)cycloalkyl (C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl (C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$) aryl, hetero(C$_{1-10}$)aryl, (C$_{9-12}$)bicycloaryl and hetero (C$_{4-12}$)bicycloaryl, each substituted or unsubstituted, or R$_{13}$ and R$_{11}$ are taken together to form a substituted or unsubstituted ring.

In yet another embodiment, MEK inhibitors of the present invention have the formula:

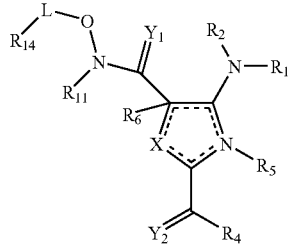

or a polymorph, solvate, ester, tautomer, enantiomer, pharmaceutically acceptable salt or prodrug thereof, wherein L is absent or a linker providing 1, 2, 3, 4, 5 or 6 atom separation between the atoms to which L is attached, wherein the atoms of the linker providing the separation are selected from the group consisting of carbon, oxygen, nitrogen, and sulfur;

R$_{11}$ is hydrogen, a substituent convertible in vivo to hydrogen, a substituted or unsubstituted (C$_{1-10}$)alkyl, or a substituted or unsubstituted halo(C$_{1-10}$)alkyl; and R$_{14}$ is selected from the group consisting of hydrogen, halo, nitro, cyano, thio, oxy, hydroxy, carbonyloxy, alkoxy, aryloxy, heteroaryloxy, carbonyl, oxycarbonyl, aminocarbonyl, amino, (C$_{1-10}$)alkylamino, sulfonamido, imino, sulfonyl, sulfinyl, (C$_{1-10}$)alkyl, halo(C$_{1-10}$) alkyl, carbonyl(C$_{1-3}$)alkyl, thiocarbonyl(C$_{1-3}$)alkyl, sulfonyl(C$_{1-3}$)alkyl, sulfinyl(C$_{1-13}$)alkyl, amino(C$_{1-10}$) alkyl, imino(C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero In a further embodiment, MEK inhibitors of the present invention have the formula:

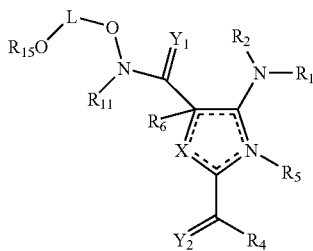

or a polymorph, solvate, ester, tautomer, enantiomer, pharmaceutically acceptable salt or prodrug thereof, wherein
L is absent or a linker providing 1, 2, 3, 4, 5 or 6 atom separation between the atoms to which L is attached, wherein the atoms of the linker providing the separation are selected from the group consisting of carbon, oxygen, nitrogen, and sulfur;
$R_{11}$ is hydrogen, a substituent convertible in vivo to hydrogen, a substituted or unsubstituted $(C_{1-10})$alkyl, or a substituted or unsubstituted halo$(C_{1-10})$alkyl; and
$R_{15}$ is selected from the group consisting of hydrogen, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl $(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$ aryl, hetero$(C_{1-10})$aryl, $(C_{9-12})$bicycloaryl and hetero $(C_{4-12})$bicycloaryl, each substituted or unsubstituted.

In still a further embodiment, MEK inhibitors of the present invention have the formula:

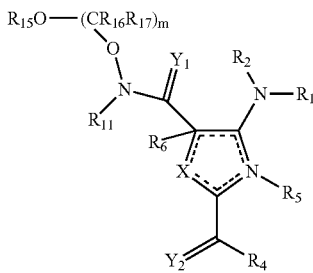

or a polymorph, solvate, ester, tautomer, enantiomer, pharmaceutically acceptable salt or prodrug thereof, wherein
m is selected from the group consisting of 0, 1, 2, 3, 4, 5, and 6;
$R_{11}$ is hydrogen, a substituent convertible in vivo to hydrogen, a substituted or unsubstituted $(C_{1-10})$alkyl, or a substituted or unsubstituted halo$(C_{1-10})$alkyl;
$R_{15}$ is selected from the group consisting of hydrogen, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl $(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$ aryl, hetero$(C_{1-10})$aryl, $(C_{9-12})$bicycloaryl and hetero $(C_{4-12})$bicycloaryl, each substituted or unsubstituted; and each $R_{16}$ and $R_{17}$ is independently selected from the group consisting of hydrogen, halo, nitro, cyano, thio, oxy, hydroxy, carbonyloxy, alkoxy, aryloxy, heteroaryloxy, carbonyl, oxycarbonyl, aminocarbonyl, amino, $(C_{1-10})$ alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl $(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$ aryl, hetero$(C_{1-10})$aryl, $(C_{9-12})$bicycloaryl and hetero $(C_{4-12})$bicycloaryl, each substituted or unsubstituted, or any two $R_{16}$ and $R_{17}$ are taken together to form a substituted or unsubstituted ring.

In yet a further embodiment, MEK inhibitors of the present invention have the formula:

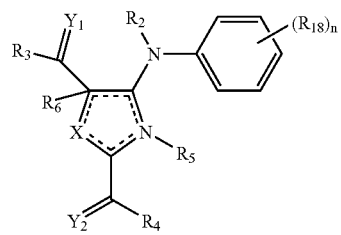

or a polymorph, solvate, ester, tautomer, enantiomer, pharmaceutically acceptable salt or prodrug thereof, wherein
n is selected from the group consisting of 0, 1, 2, 3, 4 and 5; and
each $R_{18}$ is independently selected from the group consisting of hydrogen, halo, nitro, cyano, thio, oxy, hydroxy, carbonyloxy, alkoxy, aryloxy, heteroaryloxy, carbonyl, oxycarbonyl, aminocarbonyl, amino, $(C_{1-10})$alkylamino, sulfonamido, imino, sulfonyl, sulfinyl, $(C_{1-10})$ alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl $(C_{1-5})$alkyl, hetero$(C_{3-12})$cycloalkyl$(C_{1-5})$alkyl, aryl $(C_{1-10})$alkyl, heteroaryl$(C_{1-5})$alkyl, $(C_{9-12})$bicycloaryl $(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{1-10})$aryl, $(C_{9-12})$bicycloaryl and hetero$(C_{4-12})$bicycloaryl, each substituted or unsubstituted, or two $R_{18}$ are taken together to form a substituted or unsubstituted ring.

In another embodiment, MEK inhibitors of the present invention have the formula:

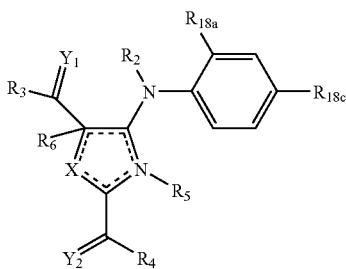

or a polymorph, solvate, ester, tautomer, enantiomer, pharmaceutically acceptable salt or prodrug thereof, wherein $R_{18a}$ and $R_{18c}$ are each independently selected from the group consisting of hydrogen, halo, nitro, cyano, thio, oxy, hydroxy, carbonyloxy, alkoxy, aryloxy, heteroaryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl $(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl $(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$ aryl, hetero$(C_{1-10})$aryl, $(C_{9-12})$bicycloaryl and hetero $(C_{4-12})$bicycloaryl, each substituted or unsubstituted.

In still another embodiment, MEK inhibitors of the present invention have the formula:

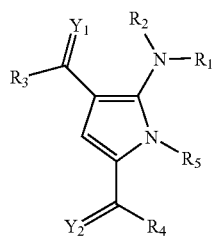

or a polymorph, solvate, ester, tautomer, enantiomer, pharmaceutically acceptable salt or prodrug thereof.

In yet another embodiment, MEK inhibitors of the present invention have the formula:

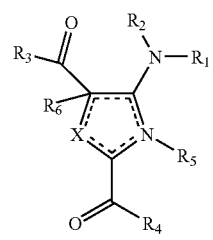

or a polymorph, solvate, ester, tautomer, enantiomer, pharmaceutically acceptable salt or prodrug thereof.

In a further embodiment, MEK inhibitors of the present invention have the formula:

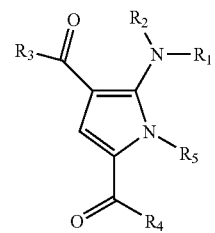

or a polymorph, solvate, ester, tautomer, enantiomer, pharmaceutically acceptable salt or prodrug thereof.

In still a further embodiment, MEK inhibitors of the present invention have the formula:

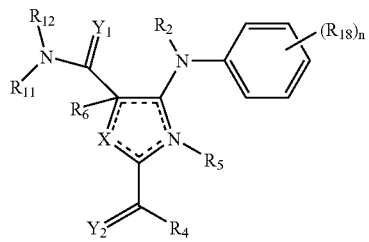

or a polymorph, solvate, ester, tautomer, enantiomer, pharmaceutically acceptable salt or prodrug thereof, wherein
n is selected from the group consisting of 0, 1, 2, 3, 4 and 5;
$R_{11}$ is hydrogen, a substituent convertible in vivo to hydrogen, a substituted or unsubstituted $(C_{1-10})$alkyl, or a substituted or unsubstituted halo$(C_{1-10})$alkyl;
$R_{12}$ is selected from the group consisting of hydrogen, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$ alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{11}$ and $R_{12}$ are taken together to form a substituted or unsubstituted ring; and
each $R_{18}$ is independently selected from the group consisting of hydrogen, halo, nitro, cyano, thio, oxy, hydroxy, carbonyloxy, alkoxy, aryloxy, heteroaryloxy, carbonyl, oxycarbonyl, aminocarbonyl, amino, $(C_{1-10})$alkylamino, sulfonamido, imino, sulfonyl, sulfinyl, $(C_{1-10})$ alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl $(C_{1-5})$alkyl, hetero$(C_{3-12})$cycloalkyl$(C_{1-5})$alkyl, aryl $(C_{1-10})$alkyl, heteroaryl$(C_{1-5})$alkyl, $(C_{9-12})$bicycloaryl $(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{1-10})$aryl, $(C_{9-12})$bicycloaryl and hetero$(C_{4-12})$bicycloaryl, each substituted or unsubstituted, or two $R_{18}$ are taken together to form a substituted or unsubstituted ring.

In yet a further embodiment, MEK inhibitors of the present invention have the formula:

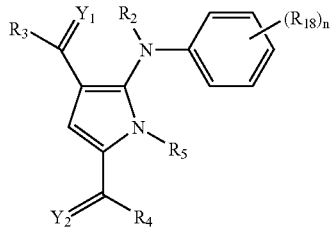

or a polymorph, solvate, ester, tautomer, enantiomer, pharmaceutically acceptable salt or prodrug thereof, wherein
n is selected from the group consisting of 0, 1, 2, 3, 4 and 5; and each $R_{18}$ is independently selected from the group consisting of hydrogen, halo, nitro, cyano, thio, oxy, hydroxy, carbonyloxy, alkoxy, aryloxy, heteroaryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or two $R_{18}$ are taken together to form a substituted or unsubstituted ring.

In another embodiment, MEK inhibitors of the present invention have the formula:

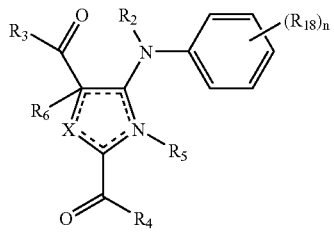

or a polymorph, solvate, ester, tautomer, enantiomer, pharmaceutically acceptable salt or prodrug thereof, wherein
n is selected from the group consisting of 0, 1, 2, 3, 4 and 5; and each $R_{18}$ is independently selected from the group consisting of hydrogen, halo, nitro, cyano, thio, oxy, hydroxy, carbonyloxy, alkoxy, aryloxy, heteroaryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or two $R_{18}$ are taken together to form a substituted or unsubstituted ring.

In still another embodiment, MEK inhibitors of the present invention have the formula:

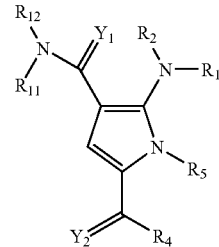

or a polymorph, solvate, ester, tautomer, enantiomer, pharmaceutically acceptable salt or prodrug thereof, wherein
$R_{11}$ is hydrogen, a substituent convertible in vivo to hydrogen, a substituted or unsubstituted $(C_{1-10})$alkyl, or a substituted or unsubstituted halo$(C_{1-10})$alkyl; and $R_{12}$ is selected from the group consisting of hydrogen, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{11}$ and $R_{12}$ are taken together to form a substituted or unsubstituted ring.

In yet another embodiment, MEK inhibitors of the present invention have the formula:

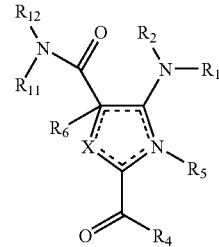

or a polymorph, solvate, ester, tautomer, enantiomer, pharmaceutically acceptable salt or prodrug thereof, wherein
$R_{11}$ is hydrogen, a substituent convertible in vivo to hydrogen, a substituted or unsubstituted $(C_{1-10})$alkyl, or a substituted or unsubstituted halo$(C_{1-10})$alkyl; and $R_{12}$ is selected from the group consisting of hydrogen, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl ($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{11}$ and $R_{12}$ are taken together to form a substituted or unsubstituted ring.

In a further embodiment, MEK inhibitors of the present invention have the formula:

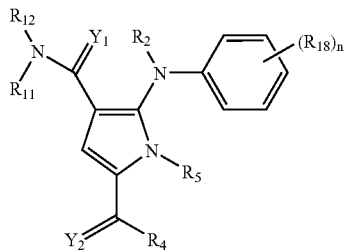

or a polymorph, solvate, ester, tautomer, enantiomer, pharmaceutically acceptable salt or prodrug thereof, wherein
n is selected from the group consisting of 0, 1, 2, 3, 4 and 5;
$R_{11}$ is hydrogen, a substituent convertible in vivo to hydrogen, a substituted or unsubstituted ($C_{1-10}$)alkyl, or a substituted or unsubstituted halo($C_{1-10}$)alkyl;
$R_{12}$ is selected from the group consisting of hydrogen, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino ($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{11}$ and $R_{12}$ are taken together to form a substituted or unsubstituted ring; and
each $R_{18}$ is independently selected from the group consisting of hydrogen, halo, nitro, cyano, thio, oxy, hydroxy, carbonyloxy, alkoxy, aryloxy, heteroaryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or two $R_{18}$ are taken together to form a substituted or unsubstituted ring.

In still a further embodiment, MEK inhibitors of the present invention have the formula:

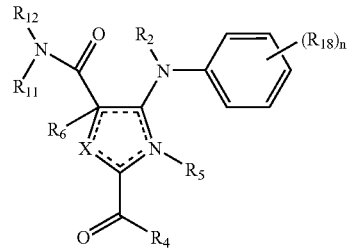

or a polymorph, solvate, ester, tautomer, enantiomer, pharmaceutically acceptable salt or prodrug thereof, wherein
n is selected from the group consisting of 0, 1, 2, 3, 4 and 5;
$R_{11}$ is hydrogen, a substituent convertible in vivo to hydrogen, a substituted or unsubstituted ($C_{1-10}$)alkyl, or a substituted or unsubstituted halo($C_{1-10}$)alkyl;
$R_{12}$ is selected from the group consisting of hydrogen, oxy, hydroxy, alkoxy, aryloxy, heteroaryloxy, carbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino ($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{11}$ and $R_{12}$ are taken together to form a substituted or unsubstituted ring; and
each $R_{18}$ is independently selected from the group consisting of hydrogen, halo, nitro, cyano, thio, oxy, hydroxy, carbonyloxy, alkoxy, aryloxy, heteroaryloxy, carbonyl, oxycarbonyl, aminocarbonyl, amino, ($C_{1-10}$)alkylamino, sulfonamido, imino, sulfonyl, sulfinyl, ($C_{1-10}$)alkyl, halo($C_{1-10}$)alkyl, carbonyl($C_{1-3}$)alkyl, thiocarbonyl($C_{1-3}$)alkyl, sulfonyl($C_{1-3}$)alkyl, sulfinyl($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or two $R_{18}$ are taken together to form a substituted or unsubstituted ring.

In yet a further embodiment, MEK inhibitors of the present invention have the formula:

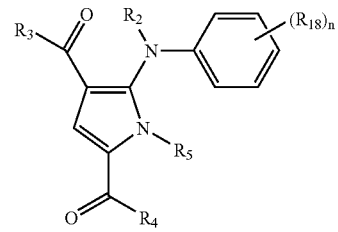

or a polymorph, solvate, ester, tautomer, enantiomer, pharmaceutically acceptable salt or prodrug thereof, wherein n is selected from the group consisting of 0, 1, 2, 3, 4 and 5; and each $R_{18}$ is independently selected from the group consisting of hydrogen, halo, nitro, cyano, thio, oxy, hydroxy, carbonyloxy, alkoxy, aryloxy, heteroaryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl $(C_{1-5})$alkyl, hetero$(C_{3-12})$cycloalkyl$(C_{1-5})$alkyl, aryl $(C_{1-10})$alkyl, heteroaryl$(C_{1-5})$alkyl, $(C_{9-12})$bicycloaryl $(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{1-10})$aryl, $(C_{9-12})$bicycloaryl and hetero$(C_{4-12})$bicycloaryl, each substituted or unsubstituted, or two $R_{18}$ are taken together to form a substituted or unsubstituted ring.

In another embodiment, MEK inhibitors of the present invention have the formula:

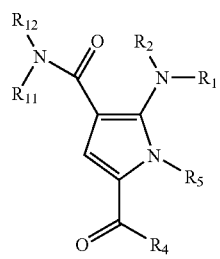

or a polymorph, solvate, ester, tautomer, enantiomer, pharmaceutically acceptable salt or prodrug thereof, wherein $R_{11}$ is hydrogen, a substituent convertible in vivo to hydrogen, a substituted or unsubstituted $(C_{1-10})$alkyl, or a substituted or unsubstituted halo$(C_{1-10})$alkyl; and $R_{12}$ is selected from the group consisting of hydrogen, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$ alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{11}$ and $R_{12}$ are taken together to form a substituted or unsubstituted ring.

In still another embodiment, MEK inhibitors of the present invention have the formula:

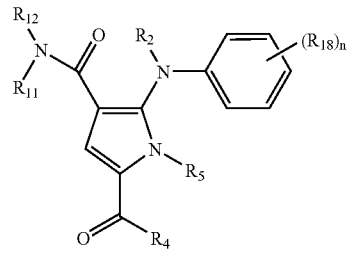

or a polymorph, solvate, ester, tautomer, enantiomer, pharmaceutically acceptable salt or prodrug thereof, wherein n is selected from the group consisting of 0, 1, 2, 3, 4 and 5;

$R_{11}$ is hydrogen, a substituent convertible in vivo to hydrogen, a substituted or unsubstituted $(C_{1-10})$alkyl, or a substituted or unsubstituted halo$(C_{1-10})$alkyl;

$R_{12}$ is selected from the group consisting of hydrogen, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$ alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{11}$ and $R_{12}$ are taken together to form a substituted or unsubstituted ring; and each $R_{18}$ is independently selected from the group consisting of hydrogen, halo, nitro, cyano, thio, oxy, hydroxy, carbonyloxy, alkoxy, aryloxy, heteroaryloxy, carbonyl, oxycarbonyl, aminocarbonyl, amino, $(C_{1-10})$alkylamino, sulfonamido, imino, sulfonyl, sulfinyl, $(C_{1-10})$ alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl $(C_{1-5})$alkyl, hetero$(C_{3-12})$cycloalkyl$(C_{1-5})$alkyl, aryl $(C_{1-10})$alkyl, heteroaryl$(C_{1-5})$alkyl, $(C_{9-12})$bicycloaryl $(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero $(C_{1-10})$aryl, $(C_{9-12})$bicycloaryl and hetero$(C_{4-12})$bicycloaryl, each substituted or unsubstituted, or two $R_{18}$ are taken together to form a substituted or unsubstituted ring.

In another of its aspects, the present invention relates to processes of making compounds of the present invention. In one embodiment, the process comprises:

reacting a compound having the formula

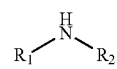

with a compound having the formula

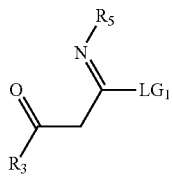

under conditions that form a first reaction product having the formula

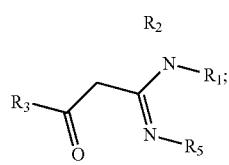

reacting the first reaction product with a compound having the formula

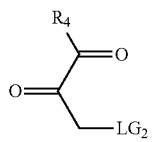

under conditions that form a second reaction product having the formula

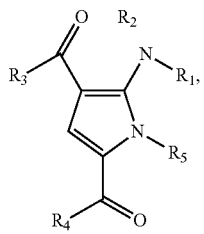

wherein $R_1$ is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_2$ is hydrogen or a substituent convertible in vivo to hydrogen;

$R_3$ is selected from the group consisting of hydroxy, amino, $(C_{1-10})$alkylamino, $(C_{1-10})$alkoxyamino, hydroxy$(C_{1-10})$alkoxyamino, hydroxy$(C_{1-10})$alkylamino, cycloamino, sulfonamido, imino, $(C_{2-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_4$ is selected from the group consisting of hydrogen, $(C_{1-10})$alkoxy, $(C_{4-12})$aryloxy, amino, $(C_{1-10})$alkylamino, sulfonamido, imino, sulfonyl, sulfinyl, $(C_{1-10})$alkyl, halo$(C_{1-10})$alkyl, hydroxy$(C_{1-10})$alkyl, carbonyl$(C_{1-10})$alkyl, thiocarbonyl$(C_{1-10})$alkyl, sulfonyl$(C_{1-10})$alkyl, sulfinyl$(C_{1-10})$alkyl, $(C_{1-10})$azaalkyl, imino$(C_{1-10})$alkyl, $(C_{3-12})$cycloalkyl$(C_{1-5})$alkyl, hetero$(C_{3-12})$cycloalkyl$(C_{1-10})$alkyl, aryl$(C_{1-10})$alkyl, hetero$(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_5$ is selected from the group consisting of hydrogen, $(C_{1-10})$alkyl, halo$(C_{1-10})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_5$ and $R_4$ are taken together to form a substituted or unsubstituted ring; and $LG_1$ and $LG_2$ are each independently a leaving group.

In one variation of the above embodiment, the second reaction product is treated under conditions that form a third reaction product having the formula

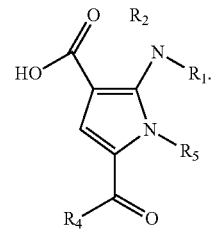

In one variation of the above embodiment or variation, the third reaction product is reacted with a compound having the formula

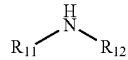

under conditions that form a product having the formula

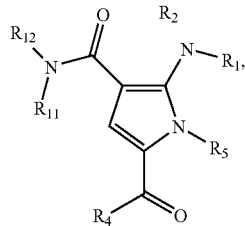

wherein
R$_{11}$ is hydrogen, a substituent convertible in vivo to hydrogen, a substituted or unsubstituted (C$_{1-10}$)alkyl, or a substituted or unsubstituted halo(C$_{1-10}$)alkyl; and
R$_{12}$ is selected from the group consisting of hydrogen, oxy, hydroxy, alkoxy, aryloxy, heteroaryloxy, carbonyl, amino, (C$_{1-10}$)alkylamino, sulfonamido, imino, sulfonyl, sulfinyl, (C$_{1-10}$)alkyl, halo(C$_{1-10}$)alkyl, carbonyl (C$_{1-3}$)alkyl, thiocarbonyl(C$_{1-3}$)alkyl, sulfonyl(C$_{1-3}$)alkyl, sulfinyl(C$_{1-3}$)alkyl, amino (C$_{1-10}$)alkyl, imino (C$_{1-3}$)alkyl, (C$_{3-12}$)cycloalkyl(C$_{1-5}$)alkyl, hetero(C$_{3-12}$)cycloalkyl(C$_{1-5}$)alkyl, aryl(C$_{1-10}$)alkyl, heteroaryl (C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted, or R$_{11}$ and R$_{12}$ are taken together to form a substituted or unsubstituted ring.

In another embodiment, the process comprises:
reacting a compound having the formula

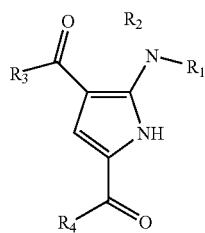

with a compound having the formula

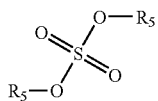

under conditions that form a product having the formula

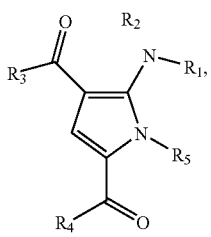

wherein
R$_1$ is selected from the group consisting of (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted;
R$_2$ is hydrogen or a substituent convertible in vivo to hydrogen;
R$_3$ is selected from the group consisting of hydroxy, amino, (C$_{1-10}$)alkylamino, (C$_{1-10}$)alkoxyamino, hydroxy (C$_{1-10}$)alkoxyamino, hydroxy(C$_{1-10}$)alkylamino, cycloamino, sulfonamido, imino, (C$_{2-10}$)alkyl, halo (C$_{1-10}$)alkyl, carbonyl(C$_{1-3}$)alkyl, thiocarbonyl(C$_{1-3}$)alkyl, sulfonyl(C$_{1-3}$)alkyl, sulfinyl(C$_{1-3}$)alkyl, amino (C$_{1-10}$)alkyl, imino(C$_{1-3}$)alkyl, (C$_{3-12}$)cycloalkyl(C$_{1-5}$) alkyl, hetero(C$_{3-12}$)cycloalkyl(C$_{1-5}$)alkyl, aryl(C$_{1-10}$) alkyl, heteroaryl(C$_{1-5}$)alkyl, (C$_{9-12}$)bicycloaryl(C$_{1-5}$) alkyl, hetero(C$_{8-12}$)bicycloaryl(C$_{1-5}$)alkyl, (C$_{3-12}$) cycloalkyl, hetero(C$_{3-12}$)cycloalkyl, (C$_{9-12}$) bicycloalkyl, hetero(C$_{3-12}$)bicycloalkyl, (C$_{4-12}$)aryl, hetero(C$_{1-10}$)aryl, (C$_{9-12}$)bicycloaryl and hetero(C$_{4-12}$) bicycloaryl, each substituted or unsubstituted;
R$_4$ is selected from the group consisting of hydrogen, (C$_{1-10}$)alkoxy, (C$_{4-12}$)aryloxy, amino, (C$_{1-10}$)alkylamino, sulfonamido, imino, sulfonyl, sulfinyl, (C$_{1-10}$) alkyl, halo(C$_{1-10}$)alkyl, hydroxy(C$_{1-10}$)alkyl, carbonyl (C$_{1-10}$)alkyl, thiocarbonyl(C$_{1-10}$)alkyl, sulfonyl(C$_{1-10}$) alkyl, sulfinyl(C$_{1-10}$)alkyl, (C$_{1-10}$)azaalkyl, imino (C$_{1-10}$)alkyl, (C$_{3-12}$)cycloalkyl(C$_{1-5}$)alkyl, hetero (C$_{3-12}$)cycloalkyl(C$_{1-10}$)alkyl, aryl(C$_{1-10}$)alkyl, hetero (C$_{1-10}$)aryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero (C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted; and
R$_5$ is selected from the group consisting of hydrogen, (C$_{1-10}$)alkyl, halo(C$_{1-10}$)alkyl, amino (C$_{1-10}$)alkyl, imino(C$_{1-3}$)alkyl, (C$_{3-12}$)cycloalkyl(C$_{1-5}$)alkyl, hetero (C$_{3-12}$)cycloalkyl(C$_{1-5}$)alkyl, aryl(C$_{1-10}$)alkyl, heteroaryl(C$_{1-5}$)alkyl, (C$_{9-12}$)bicycloaryl(C$_{1-5}$)alkyl, hetero(C$_{8-12}$)bicycloaryl(C$_{1-5}$)alkyl, (C$_{3-12}$)cycloalkyl, hetero(C$_{3-12}$)cycloalkyl, (C$_{9-12}$)bicycloalkyl, hetero (C$_{3-12}$)bicycloalkyl, (C$_{4-12}$)aryl, hetero(C$_{1-10}$)aryl, (C$_{9-12}$)bicycloaryl and hetero(C$_{4-12}$)bicycloaryl, each substituted or unsubstituted, or R$_5$ and R$_4$ are taken together to form a substituted or unsubstituted ring.

In still another of its aspects, the present invention relates to reagents useful in the preparation of MEK inhibitors. In one embodiment, the reagent has the formula:

wherein
Y$_1$ is selected from the group consisting of O, S and NR$_{10}$;
R$_1$ is selected from the group consisting of (C$_{3-12}$)cycloalkyl, hetero(C$_{3-12}$)cycloalkyl, (C$_{9-12}$)bicycloalkyl, hetero(C$_{3-12}$)bicycloalkyl, (C$_{4-12}$)aryl, hetero(C$_{1-10}$) aryl, (C$_{9-12}$)bicycloaryl and hetero(C$_{4-12}$)bicycloaryl, each substituted or unsubstituted;
R$_2$ is hydrogen or a substituent convertible in vivo to hydrogen;
R$_3$ is selected from the group consisting of hydroxy, amino, (C$_{1-10}$)alkylamino, (C$_{1-10}$)alkoxyamino, hydroxy (C$_{1-10}$)alkoxyamino, hydroxy(C$_{1-10}$)alkylamino, cycloamino, sulfonamido, imino, (C$_{2-10}$)alkyl, halo (C$_{1-10}$)alkyl, carbonyl(C$_{1-3}$)alkyl, thiocarbonyl(C$_{1-3}$) alkyl, sulfonyl(C$_{1-3}$)alkyl, sulfinyl(C$_{1-3}$)alkyl, amino (C$_{1-10}$)alkyl, imino(C$_{1-3}$)alkyl, (C$_{3-12}$)cycloalkyl(C$_{1-5}$) alkyl, hetero(C$_{3-12}$)cycloalkyl(C$_{1-5}$)alkyl, aryl(C$_{1-10}$) alkyl, heteroaryl(C$_{1-5}$)alkyl, (C$_{9-12}$)bicycloaryl(C$_{1-5}$) alkyl, hetero(C$_{8-12}$)bicycloaryl(C$_{1-5}$)alkyl, (C$_{3-12}$)

cycloalkyl, hetero($C_{3-12}$)cycloalkyl, ($C_{9-12}$) bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted;

$R_5$ is selected from the group consisting of hydrogen, ($C_{1-10}$)alkyl, halo($C_{1-10}$)alkyl, amino ($C_{1-10}$)alkyl, imino($C_{1-3}$)alkyl, ($C_{3-12}$)cycloalkyl($C_{1-5}$)alkyl, hetero ($C_{3-12}$)cycloalkyl($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_5$ and $R_4$ are taken together to form a substituted or unsubstituted ring; and $R_{10}$ is selected from the group consisting of hydrogen, ($C_{1-10}$)alkyl, halo($C_{1-10}$)alkyl, hydroxy($C_{1-10}$)alkyl, imino($C_{1-10}$)alkyl, ($C_{3-12}$)cycloalkyl($C_{1-5}$)alkyl, hetero ($C_{3-12}$)cycloalkyl($C_{1-10}$)alkyl, aryl($C_{1-10}$)alkyl, hetero ($C_{1-10}$)aryl($C_{1-5}$)alkyl, ($C_{9-12}$)bicycloaryl($C_{1-5}$)alkyl, hetero($C_{8-12}$)bicycloaryl($C_{1-5}$)alkyl, ($C_{3-12}$)cycloalkyl, hetero($C_{3-12}$)cycloalkyl, ($C_{9-12}$)bicycloalkyl, hetero ($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{10}$ and $R_3$ or $R_4$ are taken together to form a substituted or unsubstituted ring.

In one variation of the compounds and processes according to each of the above embodiments and variations, X is —N=. In another variation of the compounds and processes according to each of the above embodiments and variations, X is —$CR_7$=. In still another variation of the compounds and processes according to each of the above embodiments and variations, X is —O—.

In a further variation of the compounds and processes according to each of the above embodiments and variations, $Y_1$ is O.

In still a further variation of the compounds and processes according to each of the above embodiments and variations, $Y_1$ and $R_3$ are taken together to form a substituted or unsubstituted hetero($C_{1-6}$)aryl. In yet a further variation of the compounds and processes according to each of the above embodiments and variations, $Y_1$ and $R_3$ are taken together to form a substituted or unsubstituted triazolyl or oxadiazolyl.

In another variation of the compounds and processes according to each of the above embodiments and variations, $Y_2$ is O.

In still another variation of the compounds and processes according to each of the above embodiments and variations, $R_1$ is selected from the group consisting of ($C_{3-12}$)cycloalkyl, hetero($C_{3-12}$)cycloalkyl, ($C_{4-12}$)aryl and hetero($C_{1-10}$)aryl, each substituted or unsubstituted. In yet another variation of the compounds and processes according to each of the above embodiments and variations, $R_1$ is selected from the group consisting of ($C_{4-12}$)aryl and hetero($C_{1-10}$)aryl, each substituted or unsubstituted. In a further variation of the compounds and processes according to each of the above embodiments and variations, $R_1$ is a substituted or unsubstituted ($C_{4-12}$) aryl. In still a further variation of the compounds and processes according to each of the above embodiments and variations, $R_1$ is a substituted or unsubstituted phenyl. In yet a further variation of the compounds and processes according to each of the above embodiments and variations, $R_1$ is a substituted or unsubstituted ($C_{9-12}$)bicycloaryl. In another variation of the compounds and processes according to each of the above embodiments and variations, $R_1$ is a substituted or unsubstituted naphthyl. In still another variation of the compounds and processes according to each of the above embodiments and variations, $R_1$ is a substituted or unsubstituted hetero($C_{4-12}$)bicycloaryl. In yet another variation of the compounds and processes according to each of the above embodiments and variations, $R_1$ is substituted with one or more substituents selected from the group consisting of hydrogen, halo, cyano, thio, alkoxy, ($C_{1-3}$)alkyl, hydroxy ($C_{1-3}$)alkyl and ($C_{3-8}$)cycloalkyl, each substituted or unsubstituted. In a further variation of the compounds and processes according to each of the above embodiments and variations, $R_1$ is substituted with one or more substituents selected from the group consisting of hydrogen, fluoro, chloro, bromo, iodo, cyano, methylthio, methoxy, trifluoromethoxy, methyl, ethyl, trifluoromethyl, ethynyl, n-propanolyl and cyclopropyl.

In still a further variation of the compounds and processes according to each of the above embodiments and variations, $R_1$ comprises:

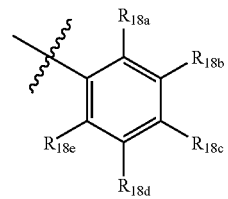

wherein $R_{18a}$, $R_{18b}$, $R_{18c}$, $R_{18d}$ and $R_{18e}$ are each independently selected from the group consisting of hydrogen, halo, cyano, thio, alkoxy, ($C_{1-3}$)alkyl and hydroxy($C_{1-3}$)alkyl, each substituted or unsubstituted.

In yet a further variation of the compounds and processes according to each of the above embodiments and variations, $R_2$ is hydrogen.

In another variation of the compounds and processes according to each of the above embodiments and variations, $R_3$ is $R_{13}$O-L-, L is absent or a linker providing 1, 2, 3, 4, 5 or 6 atom separation between the atoms to which L is attached, wherein the atoms of the linker providing the separation are selected from the group consisting of carbon, oxygen, nitrogen, and sulfur; and $R_{13}$ is selected from the group consisting of hydrogen, ($C_{1-10}$)alkyl, halo($C_{1-10}$)alkyl, carbonyl($C_{1-3}$) alkyl, thiocarbonyl($C_{1-3}$)alkyl, sulfonyl($C_{1-3}$)alkyl, sulfinyl ($C_{1-3}$)alkyl, amino ($C_{1-10}$)alkyl, imino($C_{1-3}$)alkyl, ($C_{3-12}$)cycloalkyl($C_{1-5}$)alkyl, hetero($C_{3-12}$)cycloalkyl($C_{1-5}$)alkyl, aryl ($C_{1-10}$)alkyl, heteroaryl($C_{1-5}$)alkyl, ($C_{9-12}$)bicycloaryl($C_{1-5}$) alkyl, hetero($C_{8-12}$)bicycloaryl($C_{1-5}$)alkyl, ($C_{3-12}$) cycloalkyl, hetero($C_{3-12}$)cycloalkyl, ($C_{9-12}$)bicycloalkyl, hetero($C_{3-12}$)bicycloalkyl, ($C_{4-12}$)aryl, hetero($C_{1-10}$)aryl, ($C_{9-12}$)bicycloaryl and hetero($C_{4-12}$)bicycloaryl, each substituted or unsubstituted, or $R_{13}$ and $R_{11}$ are taken together to form a substituted or unsubstituted ring.

In still another variation of the compounds and processes according to each of the above embodiments and variations, $R_4$ is selected from the group consisting of amino, ($C_{1-5}$) alkylamino, ($C_{1-5}$)alkyl, halo($C_{1-5}$)alkyl, hydroxy($C_{1-5}$) alkyl, ($C_{1-8}$)azaalkyl, hydroxy($C_{1-8}$)azaalkyl and ($C_{3-6}$)cycloalkyl, each substituted or unsubstituted.

In yet another variation of the compounds and processes according to each of the above embodiments and variations, $R_5$ is selected from the group consisting of hydrogen, ($C_{1-5}$) alkyl, amino($C_{1-10}$)alkyl, hydroxy($C_{1-10}$)alkyl and ($C_{3-12}$)cycloalkyl, each substituted or unsubstituted. In a further variation of the compounds and processes according to each of the above embodiments and variations, $R_5$ is selected from the group consisting of ($C_{1-5}$)alkyl and halo($C_{1-5}$)alkyl, each substituted or unsubstituted. In still a further variation of the compounds and processes according to each of the above embodiments and variations, $R_5$ is selected from the group consisting of $(C_{1-5})$alkyl, amino$(C_{1-5})$alkyl, carbonyl$(C_{1-5})$alkyl, hydroxy$(C_{1-5})$alkylalkoxy$(C_{1-5})$alkyl, hetero$(C_{3-12})$cycloalkyl$(C_{1-5})$alkyl and $(C_{3-8})$cycloalkyl, each substituted or unsubstituted. In yet a further variation of the compounds and processes according to each of the above embodiments and variations, $R_5$ is selected from the group consisting of $(C_{1-3})$alkyl, $(C_{1-3})$alkylamino$(C_{1-3})$alkyl, di$(C_{1-3})$alkylamino$(C_{1-3})$alkyl, terahydrofuranyl$(C_{1-3})$alkyl, pyrrolidinolyl$(C_{1-3})$alkyl, thiazolidinyl$(C_{1-3})$alkyl, hydroxyl-$(C_{1-3})$alkan-one-yl, $(C_{1-3})$alkoxy-$(C_{1-3})$alkan-one-yl, $(C_{1-5})$alkenyl, hydroxy$(C_{1-3})$alkyl, N—$(C_{1-3})$alkoxy-acetamido$(C_{1-3})$alkyl, tetrahydro-2H-1,2-oxazine-one-yl-$(C_{1-3})$alkyl, N—(($C_{1-3}$)alkylsulfinyl$(C_{1-3})$alkoxy)-amino$(C_{1-3})$alkyl, N—(($C_{1-3}$)alkylsulfinyl$(C_{1-3})$alkyl)-amino$(C_{1-3})$alkyl, $(C_{1-3})$alkylsulfonyl$(C_{1-3})$alkoxy$(C_{1-3})$alkyl, imidazolidin-one-yl-$(C_{1-3})$alkyl, dihydroxy-$(C_{1-5})$alkyl and isoxazolidin-one-yl-$(C_{1-3})$alkyl, each substituted or unsubstituted.

In another variation of the compounds and processes according to each of the above embodiments and variations, $R_5$ is selected from the group consisting of ethyl, propyl, n-butyl, cyclopropyl, cyclobutyl, cyclopentyl, cyclohexyl, methylaminomethyl, dimethylaminomethyl, terahydrofuranylmethyl, terahydrofuranylethyl, pyrrolidinolylmethyl, thiazolidinylmethyl, thiazolidinylethyl, hydroxyl-propan-one-yl, methoxy-propan-one-yl, butenyl, hydroxybutanyl, N-methoxy-acetamidomethyl, tetrahydro-2H-1,2-oxazine-one-yl-methyl, N-(methylsulfinylethoxy)-aminomethyl, N-(methylsulfinylpropyl)-aminomethyl, methylsulfonylethoxymethyl, imidazolidin-one-yl-ethyl, dihydroxy-butanyl and isoxazolidin-one-yl-methyl. In still another variation of the compounds and processes according to each of the above embodiments and variations, $R_5$ is hydrogen. In yet another variation of the compounds and processes according to each of the above embodiments and variations, $R_5$ is methyl.

In a further variation of the compounds and processes according to each of the above embodiments and variations, $R_6$ is selected from the group consisting of hydrogen and a substituted or unsubstituted $(C_{1-5})$alkyl. In still a further variation of the compounds and processes according to each of the above embodiments and variations, $R_6$ is hydrogen.

In yet a further variation of the compounds and processes according to each of the above embodiments and variations, $R_7$ is hydrogen. In another variation of the compounds and processes according to each of the above embodiments and variations, $R_7$ is a substituted or unsubstituted $(C_{1-3})$alkyl. In still another variation of the compounds and processes according to each of the above embodiments and variations, $R_7$ is halo.

In yet another variation of the compounds and processes according to each of the above embodiments and variations, $R_8$ is hydrogen.

In a further variation of the compounds and processes according to each of the above embodiments and variations, $R_9$ is hydrogen. In still a further variation of the compounds and processes according to each of the above embodiments and variations, $R_9$ is selected from the group consisting of $(C_{1-5})$alkyl and halo$(C_{1-5})$alkyl, each substituted or unsubstituted.

In yet a further variation of the compounds and processes according to each of the above embodiments and variations, $R_{10}$ is a substituted or unsubstituted $(C_{1-5})$alkyl.

In another variation of the compounds and processes according to each of the above embodiments and variations, $R_{11}$ is hydrogen. In still another variation of the compounds and processes according to each of the above embodiments and variations, $R_{11}$ is selected from the group consisting of $(C_{1-5})$alkyl and halo$(C_{1-5})$alkyl, each substituted or unsubstituted.

In yet another variation of the compounds and processes according to each of the above embodiments and variations, $R_{12}$ is selected from the group consisting of hydrogen, hydroxyl, alkoxy, $(C_{1-10})$alkyl, hydroxy$(C_{1-10})$alkyl, $(C_{3-12})$cycloalkyl, hetero$(C_{3-12})$cycloalkyl and hetero$(C_{1-10})$aryl, each substituted or unsubstituted.

In a further variation of the compounds and processes according to each of the above embodiments and variations, $R_{12}$ is $R_{13}$O-L-, L is absent or a linker providing 1, 2, 3, 4, 5 or 6 atom separation between the atoms to which L is attached, wherein the atoms of the linker providing the separation are selected from the group consisting of carbon, oxygen, nitrogen, and sulfur; and $R_{13}$ is selected from the group consisting of hydrogen, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{13}$ and $R_{11}$ are taken together to form a substituted or unsubstituted ring.

In still a further variation of the compounds and processes according to each of the above embodiments and variations, $R_{12}$ is selected from the group consisting of triazolyl, oxadiazolyl and oxazolyl, each substituted or unsubstituted. In yet a further variation of the compounds and processes according to each of the above embodiments and variations, $R_{12}$ is not taken together with $R_9$ to form a ring.

In another variation of the compounds and processes according to each of the above embodiments and variations, $R_{13}$ is selected from the group consisting of hydrogen, alkoxy, $(C_{1-10})$alkyl, hydroxy$(C_{1-10})$alkyl and hetero$(C_{3-12})$cycloalkyl$(C_{1-10})$alkyl, each substituted or unsubstituted.

In still another variation of the compounds and processes according to each of the above embodiments and variations, L is a substituted or unsubstituted $(C_{1-10})$alkylene. In yet another variation of the compounds and processes according to each of the above embodiments and variations, L is a substituted or unsubstituted $(C_{1-3})$alkylene.

In a further variation of the compounds and processes according to each of the above embodiments and variations, L is —$(CR_{16}R_{17})_m$—; m is selected from the group consisting of 0, 1, 2, 3, 4, 5, and 6; and each $R_{16}$ and $R_{17}$ is independently selected from the group consisting of hydrogen, halo, nitro, cyano, thio, oxy, hydroxy, carbonyloxy, alkoxy, aryloxy, heteroaryloxy, carbonyl, oxycarbonyl, aminocarbonyl, amino, $(C_{1-10})$alkylamino, sulfonamido, imino, sulfonyl, sulfinyl, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl$(C_{1-3})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or any two $R_{16}$ and $R_{17}$ are taken together to form a substituted or unsubstituted ring.

In still a further variation of the compounds and processes according to each of the above embodiments and variations, $R_{14}$ is selected from the group consisting of hydroxyl, $(C_{3-12})$ cycloalkyl and hetero$(C_{3-12})$cycloalkyl, each substituted or unsubstituted.

In yet a further variation of the compounds and processes according to each of the above embodiments and variations, $R_{14}$ is —$NR_{19}R_{20}$; and $R_{19}$ and $R_{20}$ are each independently selected from the group consisting of hydrogen, $(C_{1-10})$alkyl, halo$(C_{1-10})$alkyl, amino$(C_{1-10})$alkyl, imino$(C_{1-3})$alkyl, $(C_{3-12})$cycloalkyl$(C_{1-5})$alkyl, hetero$(C_{3-12})$cycloalkyl$(C_{1-5})$alkyl, aryl$(C_{1-10})$alkyl, heteroaryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{19}$ and $R_{20}$ are taken together to form a substituted or unsubstituted ring. In one particular variation, $R_{19}$ and/or $R_{20}$ are each independently hydrogen.

In another variation of the compounds and processes according to each of the above embodiments and variations, $R_{15}$ is selected from the group consisting of hydrogen and a substituted or unsubstituted $(C_{1-5})$alkyl.

In still another variation of the compounds and processes according to each of the above embodiments and variations, m is 0. In yet another variation of the compounds and processes according to each of the above embodiments and variations, m is 1.

In a further variation of the compounds and processes according to each of the above embodiments and variations, each $R_{16}$ is independently selected from the group consisting of hydrogen, hydroxyl, $(C_{1-5})$alkyl and hydroxy$(C_{1-5})$alkyl, each substituted or unsubstituted.

In still a further variation of the compounds and processes according to each of the above embodiments and variations, each $R_{17}$ is independently selected from the group consisting of hydrogen, hydroxyl, $(C_{1-5})$alkyl and hydroxy$(C_{1-5})$alkyl, each substituted or unsubstituted.

In yet a further variation of the compounds and processes according to each of the above embodiments and variations, n is 1. In another variation of the compounds and processes according to each of the above embodiments and variations, n is 2.

In still another variation of the compounds and processes according to each of the above embodiments and variations, each $R_{18}$ is independently selected from the group consisting of hydrogen, halo, cyano, carbonyl, $(C_{1-5})$alkyl and $(C_{3-12})$cycloalkyl, each substituted or unsubstituted. In yet another variation of the compounds and processes according to each of the above embodiments and variations, $R_{18a}$ is selected from the group consisting of hydrogen, halo, and a substituted or unsubstituted $(C_{1-5})$alkyl. In a further variation of the compounds and processes according to each of the above embodiments and variations, $R_{18a}$ is selected from the group consisting of fluoro, chloro and methyl. In still a further variation of the compounds and processes according to each of the above embodiments and variations, $R_{18c}$ is selected from the group consisting of hydrogen, halo, cyano, thio, $(C_{1-3})$alkyl and hydroxy$(C_{1-3})$alkyl, each substituted or unsubstituted. In yet a further variation of the compounds and processes according to each of the above embodiments and variations, $R_{18c}$ is selected from the group consisting of iodo and bromo.

In another variation of the compounds and processes according to each of the above embodiments and variations, $LG_1$ is phenoxy. In still another variation of the compounds and processes according to each of the above embodiments and variations, $LG_2$ is halo.

Particular examples of compounds according to the present invention include, but are not limited to:

5-Acetyl-2-(2-fluoro-4-iodo-phenylamino)-1H-pyrrole-3-carboxylic acid;

5-Acetyl-2-(2-fluoro-4-iodophenylamino)-N-(2-hydroxyethoxy)-1H-pyrrole-3-carboxamide;

5-Acetyl-2-(2-fluoro-4-iodophenylamino)-1-methyl-1H-pyrrole-3-carboxylic acid;

5-Acetyl-2-(2-fluoro-4-iodophenylamino)-N-(2-hydroxyethoxy)-1-methyl-1H-pyrrole-3-carboxamide;

5-Acetyl-2-(2-fluoro-4-iodophenylamino)-N-(3-hydroxypropoxy)-1-methyl-1H-pyrrole-3-carboxamide;

(R)-5-Acetyl-N-(2,3-dihydroxypropoxy)-2-(2-fluoro-4-iodophenylamino)-1-methyl-1H-pyrrole-3-carboxamide;

(S)-5-Acetyl-N-(2,3-dihydroxypropoxy)-2-(2-fluoro-4-iodophenylamino)-1-methyl-1H-pyrrole-3-carboxamide;

5-Acetyl-2-(2-fluoro-4-iodophenylamino)-N-(3-hydroxy-2-(hydroxymethyl)propoxy)-1-methyl-1H-pyrrole-3-carboxamide;

5-Acetyl-4-chloro-2-(2-fluoro-4-iodophenylamino)-1-methyl-1H-pyrrole-3-carboxylic acid;

(R)-5-Acetyl-4-chloro-N-(2,3-dihydroxypropoxy)-2-(2-fluoro-4-iodophenylamino)-1-methyl-1H-pyrrole-3-carboxamide;

(S)-5-Acetyl-4-chloro-N-(2,3-dihydroxypropoxy)-2-(2-fluoro-4-iodophenylamino)-1-methyl-1H-pyrrole-3-carboxamide;

5-Acetyl-4-chloro-2-(2-fluoro-4-iodophenylamino)-N-(2-hydroxyethoxy)-1-methyl-1H-pyrrole-3-carboxamide;

5-Acetyl-2-(2-fluoro-4-iodophenylamino)-1-methyl-1H-pyrrole-3-carboxamide;

5-Acetyl-N-(1,3-dihydroxypropan-2-yloxy)-2-(2-fluoro-4-iodophenylamino)-1-methyl-1H-pyrrole-3-carboxamide;

5-Acetyl-N-(2,3-dihydroxypropyl)-2-(2-fluoro-4-iodophenylamino)-1-methyl-1H-pyrrole-3-carboxamide;

5-Acetyl-2-(2-fluoro-4-iodophenylamino)-N-(3-hydroxypropyl)-1-methyl-1H-pyrrole-3-carboxamide;

5-Acetyl-2-(2-fluoro-4-iodophenylamino)-N-methoxy-N,1-dimethyl-1H-pyrrole-3-carboxamide;

1-(5-(2-Fluoro-4-iodophenylamino)-4-(4-hydroxyisoxazolidine-2-carbonyl)-1-methyl-1H-pyrrol-2-yl)ethanone;

(R)-5-Acetyl-N-(2,4-dihydroxybutoxy)-2-(2-fluoro-4-iodophenylamino)-1-methyl-1H-pyrrole-3-carboxamide;

(S)-5-Acetyl-N-(2,4-dihydroxybutoxy)-2-(2-fluoro-4-iodophenylamino)-1-methyl-1H-pyrrole-3-carboxamide;

1-(4-(Azetidine-1-carbonyl)-5-(2-fluoro-4-iodophenylamino)-1-methyl-1H-pyrrol-2-yl)ethanone;

1-(4-(3-Aminoazetidine-1-carbonyl)-5-(2-fluoro-4-iodophenylamino)-1-methyl-1H-pyrrol-2-yl)ethanone;

(S)-1-(5-(2-Fluoro-4-iodophenylamino)-4-(3-(hydroxymethyl)pyrrolidine-1-carbonyl)-1-methyl-1H-pyrrol-2-yl)ethanone;

1-(5-(2-Fluoro-4-iodophenylamino)-4-(2-(hydroxymethyl)azetidine-1-carbonyl)-1-methyl-1H-pyrrol-2-yl)ethanone;

(R)-1-(5-(2-Fluoro-4-iodophenylamino)-4-(3-(hydroxymethyl)pyrrolidine-1-carbonyl)-1-methyl-1H-pyrrol-2-yl)ethanone;

1-(4-((2R,3S,4S)-3,4-Dihydroxy-2-(hydroxymethyl)pyrrolidine-1-carbonyl)-5-(2-fluoro-4-iodophenylamino)-1-methyl-1H-pyrrol-2-yl)ethanone;

1-[5-(2-Fluoro-4-iodo-phenylamino)-4-(3-hydroxy-azetidine-1-carbonyl)-1-methyl-1H-pyrrol-2-yl]-ethanone;
1-[5-(2-Fluoro-4-iodo-phenylamino)-4-((R)-3-hydroxy-pyrrolidine-1-carbonyl)-1-methyl-1H-pyrrol-2-yl]-ethanone;
1-[5-(2-Fluoro-4-iodo-phenylamino)-4-((S)-3-hydroxy-pyrrolidine-1-carbonyl)-1-methyl-1H-pyrrol-2-yl]-ethanone;
1-[5-(2-Fluoro-4-iodo-phenylamino)-1-methyl-4-(pyrrolidine-1-carbonyl)-1H-pyrrol-2-yl]-ethanone;
1-[5-(2-Fluoro-4-iodo-phenylamino)-4-((S)-2-hydroxymethyl-pyrrolidine-1-carbonyl)-1-methyl-1H-pyrrol-2-yl]-ethanone;
1-[5-(2-Fluoro-4-iodo-phenylamino)-4-((R)-2-hydroxymethyl-pyrrolidine-1-carbonyl)-1-methyl-1H-pyrrol-2-yl]-ethanone;
1-[4-(3-(R)-Amino-pyrrolidine-1-carbonyl)-5-(2-fluoro-4-iodo-phenylamino)-1-methyl-1H-pyrrol-2-yl]-ethanone;
Methanesulfonic acid 1-[5-acetyl-2-(2-fluoro-4-iodo-phenylamino)-1-methyl-1H-pyrrole-3-carbonyl]-azetidin-3-yl ester;
1-{5-(2-Fluoro-4-iodo-phenylamino)-4-[3-(2-hydroxy-ethylamino)-azetidine-1-carbonyl]-1-methyl-1H-pyrrol-2-yl}-ethanone;
1-(5-(2-Fluoro-4-iodo-phenylamino)-4-{3-[(2-hydroxyethyl)-methyl-amino]-azetidine-1-carbonyl}-1-methyl-1H-pyrrol-2-yl)-ethanone;
1-[4-(3-Dimethylamino-azetidine-1-carbonyl)-5-(2-fluoro-4-iodo-phenylamino)-1-methyl-1H-pyrrol-2-yl]-ethanone;
1-[5-(2-Fluoro-4-iodo-phenylamino)-4-(3-hydroxy-3-hydroxymethyl-azetidine-1-carbonyl)-1-methyl-1H-pyrrol-2-yl]-ethanone;
Ethyl 5-acetyl-4-fluoro-2-(2-fluoro-4-iodophenylamino)-1-methyl-1H-pyrrole-3-carboxylate;
5-Acetyl-4-fluoro-2-(2-fluoro-4-iodophenylamino)-1-methyl-1H-pyrrole-3-carboxylic acid;
(R)-5-Acetyl-N-(2,3-dihydroxypropoxy)-4-fluoro-2-(2-fluoro-4-iodophenylamino)-1-methyl-1H-pyrrole-3-carboxamide;
(S)-5-acetyl-N-(2,3-dihydroxypropoxy)-4-fluoro-2-(2-fluoro-4-iodophenylamino)-1-methyl-1H-pyrrole-3-carboxamide;
5-Acetyl-2-(4-bromo-2-fluorophenylamino)-N-(2-hydroxyethoxy)-1-methyl-1H-pyrrole-3-carboxamide;
2-(2-fluoro-4-iodophenylamino)-N-(2-hydroxyethoxy)-1-methyl-5-propionyl-1H-pyrrole-3-carboxamide;
2-(2-fluoro-4-iodophenylamino)-5-(2-fluoroacetyl)-N-(2-hydroxyethoxy)-1-methyl-1H-pyrrole-3-carboxamide;
5-(2,2-difluoroacetyl)-2-(2-fluoro-4-iodophenylamino)-N-(2-hydroxyethoxy)-1-methyl-1H-pyrrole-3-carboxamide;
2-(2-fluoro-4-iodophenylamino)-N-(2-hydroxyethoxy)-1-methyl-5-(2,2,2-trifluoroacetyl)-1H-pyrrole-3-carboxamide;
5-(2-fluoro-4-iodophenylamino)-N4-(2-hydroxyethoxy)-1-methyl-1H-pyrrole-2,4-dicarboxamide;
5-(2-fluoro-4-iodophenylamino)-N4-(2-hydroxyethoxy)-N2,1-dimethyl-1H-pyrrole-2,4-dicarboxamide;
5-(cyclopropanecarbonyl)-2-(2-fluoro-4-iodophenylamino)-N-(2-hydroxyethoxy)-1-methyl-1H-pyrrole-3-carboxamide;
5-acetyl-2-(2-fluoro-4-iodophenylamino)-N-(2-hydroxyethoxy)-1,4-dimethyl-1H-pyrrole-3-carboxamide;
5-acetyl-4-fluoro-2-(2-fluoro-4-iodophenylamino)-N-(2-hydroxyethoxy)-1-methyl-1H-pyrrole-3-carboxamide;

1-(5-acetyl-2-(2-fluoro-4-iodophenylamino)-1-methyl-1H-pyrrol-3-yl)-2-hydroxyethanone;
2-(2-fluoro-4-iodophenylamino)-5-(2-hydroxyacetyl)-N-(2-hydroxyethoxy)-1-methyl-1H-pyrrole-3-carboxamide;
2-(2-fluoro-4-iodophenylamino)-N-(2-hydroxyethoxy)-5-(3-hydroxypropanoyl)-1-methyl-1H-pyrrole-3-carboxamide;
2-(2-fluoro-4-iodophenylamino)-N-(2-hydroxyethoxy)-1-methyl-5-(2-(methylamino)acetyl)-1H-pyrrole-3-carboxamide;
5-(2-(dimethylamino)acetyl)-2-(2-fluoro-4-iodophenylamino)-N-(2-hydroxyethoxy)-1-methyl-1H-pyrrole-3-carboxamide;
2-(2-fluoro-4-iodophenylamino)-N-(2-hydroxyethoxy)-5-(2-(2-hydroxyethylamino)acetyl)-1-methyl-1H-pyrrole-3-carboxamide;
2-acetyl-5-(2-fluoro-4-iodophenylamino)-N-(2-hydroxyethoxy)-1-methyl-1H-imidazole-4-carboxamide;
5-(2-fluoro-4-iodophenylamino)-N4-(2-hydroxyethoxy)-N2,1-dimethyl-1H-imidazole-2,4-dicarboxamide;
5-(2-fluoro-4-iodophenylamino)-N4-(2-hydroxyethoxy)-1-methyl-1H-imidazole-2,4-dicarboxamide;
5-(2-fluoro-4-iodophenylamino)-2-(2-hydroxyacetyl)-N-(2-hydroxyethoxy)-1-methyl-1H-imidazole-4-carboxamide;
5-acetyl-2-(2-chloro-4-iodophenylamino)-N-(2-hydroxyethoxy)-1-methyl-1H-pyrrole-3-carboxamide;
5-acetyl-N-(2-hydroxyethoxy)-2-(4-iodo-2-methylphenylamino)-1-methyl-1H-pyrrole-3-carboxamide;
5-acetyl-2-(4-bromo-2-chlorophenylamino)-N-(2-hydroxyethoxy)-1-methyl-1H-pyrrole-3-carboxamide;
5-acetyl-2-(2-fluoro-4-iodophenylamino)-N-hydroxy-1-methyl-1H-pyrrole-3-carboxamide;
5-acetyl-N-(2-(dimethylamino)ethoxy)-2-(2-fluoro-4-iodophenylamino)-1-methyl-1H-pyrrole-3-carboxamide;
5-acetyl-N-(cyclopropylmethoxy)-2-(2-fluoro-4-iodophenylamino)-1-methyl-1H-pyrrole-3-carboxamide;
1-(5-(2-fluoro-4-iodophenylamino)-1-methyl-4-(5-methyl-4H-1,2,4-triazol-3-yl)-1H-pyrrol-2-yl)ethanone;
1-(5-(2-fluoro-4-iodophenylamino)-1-methyl-4-(5-methyl-1,3,4-oxadiazol-2-yl)-1H-pyrrol-2-yl)ethanone;
5-acetyl-2-(2-fluoro-4-iodophenylamino)-1-methyl-N-(1,2,4-oxadiazol-5-yl)-1H-pyrrole-3-carboxamide;
5-acetyl-2-(2-fluoro-4-iodophenylamino)-1-methyl-N-(1,3,4-oxadiazol-2-yl)-1H-pyrrole-3-carboxamide;
5-acetyl-2-(2-fluoro-4-iodophenylamino)-1-methyl-N-(oxazol-2-yl)-1H-pyrrole-3-carboxamide; and
5-acetyl-2-(2-fluoro-4-iodophenylamino)-N-(2-hydroxyethyl)-1-methyl-1H-pyrrole-3-carboxamide.

Particular examples of compounds according to the present invention also include, but are not limited to:
5-Acetyl-2-(2-fluoro-4-iodophenylamino)-N-(2-hydroxyethoxy)-1-methyl-1H-pyrrole-3-carboxamide;
(R)-5-Acetyl-N-(2,3-dihydroxypropoxy)-2-(2-fluoro-4-iodophenylamino)-1-methyl-1H-pyrrole-3-carboxamide;
(S)-5-Acetyl-N-(2,3-dihydroxypropoxy)-2-(2-fluoro-4-iodophenylamino)-1-methyl-1H-pyrrole-3-carboxamide;
(R)-5-Acetyl-4-chloro-N-(2,3-dihydroxypropoxy)-2-(2-fluoro-4-iodophenylamino)-1-methyl-1H-pyrrole-3-carboxamide;
(S)-5-Acetyl-4-chloro-N-(2,3-dihydroxypropoxy)-2-(2-fluoro-4-iodophenylamino)-1-methyl-1H-pyrrole-3-carboxamide;

5-Acetyl-N-(1,3-dihydroxypropan-2-yloxy)-2-(2-fluoro-4-iodophenylamino)-1-methyl-1H-pyrrole-3-carboxamide;

(R)-5-Acetyl-N-(2,3-dihydroxypropoxy)-4-fluoro-2-(2-fluoro-4-iodophenylamino)-1-methyl-1H-pyrrole-3-carboxamide; and (S)-5-acetyl-N-(2,3-dihydroxypropoxy)-4-fluoro-2-(2-fluoro-4-iodophenylamino)-1-methyl-1H-pyrrole-3-carboxamide.

It is noted that the compounds of the present invention may be in the form of a pharmaceutically acceptable salt, biohydrolyzable ester, biohydrolyzable amide, biohydrolyzable carbamate, solvate, hydrate or prodrug thereof. For example, the compound optionally comprises a substituent that is convertible in vivo to a different substituent such as hydrogen.

It is further noted that the compound may be present as a mixture of stereoisomers, or the compound may be present as a single stereoisomer.

In another of its aspects, there is provided a pharmaceutical composition comprising as an active ingredient a compound according to any one of the above embodiments and variations. In one particular variation, the composition is a solid formulation adapted for oral administration. In another particular variation, the composition is a liquid formulation adapted for oral administration. In yet another particular variation, the composition is a tablet. In still another particular variation, the composition is a liquid formulation adapted for parenteral administration.

The present invention also provides a pharmaceutical composition comprising a compound according to any one of the above embodiments and variations, wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, and intrathecally.

In yet another of its aspects, there is provided a kit comprising a compound of any one of the above embodiments and variations; and instructions which comprise one or more forms of information selected from the group consisting of indicating a disease state for which the composition is to be administered, storage information for the composition, dosing information and instructions regarding how to administer the composition. In one particular variation, the kit comprises the compound in a multiple dose form.

In still another of its aspects, there is provided an article of manufacture comprising a compound of any one of the above embodiments and variations; and packaging materials. In one variation, the packaging material comprises a container for housing the compound. In one particular variation, the container comprises a label indicating one or more members of the group consisting of a disease state for which the compound is to be administered, storage information, dosing information and/or instructions regarding how to administer the compound. In another variation, the article of manufacture comprises the compound in a multiple dose form.

In a further of its aspects, there is provided a therapeutic method comprising administering a compound of any one of the above embodiments and variations to a subject.

In another of its aspects, there is provided a method of inhibiting a Mitogen-Activated Protein Kinase (MEK) comprising contacting the MEK with a compound of any one of the above embodiments and variations.

In yet another of its aspects, there is provided a method of inhibiting a Mitogen-Activated Protein Kinase (MEK) comprising causing a compound of any one of the above embodiments and variations to be present in a subject in order to inhibit the MEK in vivo.

In a further of its aspects, there is provided a method of inhibiting Mitogen-Activated Protein Kinase (MEK) comprising administering a first compound to a subject that is converted in vivo to a second compound wherein the second compound inhibits the MEK in vivo, the second compound being a compound according to any one of the above embodiments and variations.

In another of its aspects, there is provided a method of treating a disease state for which a Mitogen-Activated Protein Kinase (MEK) possesses activity that contributes to the pathology and/or symptomology of the disease state, the method comprising causing a compound of any one of the above embodiments and variations to be present in a subject in a therapeutically effective amount for the disease state.

In yet another of its aspects, there is provided a method of treating a disease state for which a Mitogen-Activated Protein Kinase (MEK) possesses activity that contributes to the pathology and/or symptomology of the disease state, the method comprising administering a compound of any one of the above embodiments and variations to a subject, wherein the compound is present in the subject in a therapeutically effective amount for the disease state.

In a further of its aspects, there is provided a method of treating a disease state for which a Mitogen-Activated Protein Kinase (MEK) possesses activity that contributes to the pathology and/or symptomology of the disease state, the method comprising administering a first compound to a subject that is converted in vivo to a second compound wherein the second compound inhibits the MEK in vivo. It is noted that the compounds of the present invention may be the first or second compounds.

In one variation of each of the above methods the disease state is selected from the group consisting of cancerous hyperproliferative disorders (e.g., brain, lung, squamous cell, bladder, gastric, pancreatic, breast, head, neck, renal, kidney, ovarian, prostate, colorectal, epidermoid, esophageal, testicular, gynecological or thyroid cancer); non-cancerous hyperproliferative disorders (e.g., benign hyperplasia of the skin (e.g., psoriasis), restenosis, and benign prostatic hypertrophy (BPH)); pancreatitis; kidney disease; pain; preventing blastocyte implantation; treating diseases related to vasculogenesis or angiogenesis (e.g., tumor angiogenesis, acute and chronic inflammatory disease such as rheumatoid arthritis, atherosclerosis, inflammatory bowel disease, skin diseases such as psoriasis, excema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer); asthma; neutrophil chemotaxis (e.g., reperfusion injury in myocardial infarction and stroke and inflammatory arthritis); septic shock; T-cell mediated diseases where immune suppression would be of value (e.g., the prevention of organ transplant rejection, graft versus host disease, lupus erythematosus, multiple sclerosis, and rheumatoid arthritis); atherosclerosis; inhibition of keratinocyte responses to growth factor cocktails; and other diseases.

In another variation of each of the above methods, the Mitogen-Activated Protein Kinase (MEK) is MEK1. In still another variation of each of the above methods, the Mitogen-Activated Protein Kinase (MEK) is MEK2.

In another of its aspects, there is provided a method of inhibiting an Extracellular Regulated Kinase (ERK) comprising contacting the ERK with a compound of any of the above embodiments and variations.

In still another of its aspects, there is provided a method of inhibiting Extracellular Regulated Kinase (ERK) comprising causing a compound of any of the above embodiments and variations to be present in a subject in order to inhibit the ERK in vivo.

In yet another of its aspects, there is provided a method of inhibiting Extracellular Regulated Kinase (ERK) comprising administering a first compound to a subject that is converted in vivo to a second compound wherein the second compound inhibits the ERK in vivo, the second compound being a compound according to any of the above embodiments and variations.

In one variation of the above methods, the Extracellular Regulated Kinase (ERK) is ERK1. In another variation of the above methods, the Extracellular Regulated Kinase (ERK) is ERK2.

In another of its aspects, there is provided a method of treating a disease state for which a mutation in the B-Raf gene contributes to the pathology and/or symptomology of the disease state including, for example, melanomas, lung cancer, colon cancer and other tumor types.

In still another of its aspects, the present invention relates to the use of a compound of any of the above embodiments and variations as a medicament.

In yet another of its aspects, the present invention relates to the use of a compound according to any one of the above embodiments and variations in the manufacture of a medicament for inhibiting a Mitogen-Activated Protein Kinase (MEK).

In a further of its aspects, the present invention relates to the use of a compound according to any one of the above embodiments and variations in the manufacture of a medicament for treating a disease state for which a Mitogen-Activated Protein Kinase (MEK) possesses activity that contributes to the pathology and/or symptomology of the disease state.

In still a further of its aspects, the present invention relates to the use of a compound according to any one of the above embodiments and variations in the manufacture of a medicament for treating hyperproliferative disorders; pancreatitis; kidney disease; pain; diseases involving blastocyte implantation; diseases related to vasculogenesis or angiogenesis; asthma; neutrophil chemotaxis; and septic shock.

Salts, Hydrates, and Prodrugs of MEK Inhibitors

It should be recognized that the compounds of the present invention may be present and optionally administered in the form of salts, hydrates and prodrugs that are converted in vivo into the compounds of the present invention. For example, it is within the scope of the present invention to convert the compounds of the present invention into and use them in the form of their pharmaceutically acceptable salts derived from various organic and inorganic acids and bases in accordance with procedures well known in the art.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids and their corresponding salts such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, malonate, mandelate, metaphosphate, methanesulfonate, methylbenzoate, monohydrogenphosphate, 2-naphthalenesulfonate, nicotinate, nitrate, oxalate, oleate, pamoate, pectinate, persulfate, phenylacetate, 3-phenylpropionate, phosphate, phosphonate and phthalate. It should be recognized that the free base forms will typically differ from their respective salt forms somewhat in physical properties such as solubility in polar solvents, but otherwise the salts are equivalent to their respective free base forms for the purposes of the present invention.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine(benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

Compounds of the present invention that comprise basic nitrogen-containing groups may be quaternized with such agents as ($C_{1-4}$) alkyl halides, e.g., methyl, ethyl, iso-propyl and tert-butyl chlorides, bromides and iodides; di($C_{1-4}$) alkyl sulfates, e.g., dimethyl, diethyl and diamyl sulfates; ($C_{10-18}$) alkyl halides, e.g., decyl, dodecyl, lauryl, myristyl and stearyl chlorides, bromides and iodides; and aryl ($C_{1-4}$) alkyl halides, e.g., benzyl chloride and phenethyl bromide. Such salts permit the preparation of both water-soluble and oil-soluble compounds of the present invention.

N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Prodrug derivatives of compounds according to the present invention can be prepared by modifying substituents of compounds of the present invention that are then converted in vivo to a different substituent. It is noted that in many instances, the prodrugs themselves also fall within the scope of the range of compounds according to the present invention. For example, prodrugs can be prepared by reacting a compound with a carbamylating agent (e.g., 1,1-acyloxyalkylcarbonochloridate, para-nitrophenyl carbonate, or the like) or an acylating agent. Further examples of methods of making prodrugs are described in Saulnier et al. (1994), Bioorganic and Medicinal Chemistry Letters, Vol. 4, p. 1985.

Protected derivatives of compounds of the present invention can also be made. Examples of techniques applicable to the creation of protecting groups and their removal can be found in T. W. Greene, Protecting Groups in Organic Synthesis, $3^{rd}$ edition, John Wiley & Sons, Inc. 1999.

Compounds of the present invention may also be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

A "pharmaceutically acceptable salt", as used herein, is intended to encompass any compound according to the present invention that is utilized in the form of a salt thereof, especially where the salt confers on the compound improved pharmacokinetic properties as compared to the free form of compound or a different salt form of the compound. The pharmaceutically acceptable salt form may also initially confer desirable pharmacokinetic properties on the compound that it did not previously possess, and may even positively affect the pharmacodynamics of the compound with respect to its therapeutic activity in the body. An example of a pharmacokinetic property that may be favorably affected is the manner in which the compound is transported across cell membranes, which in turn may directly and positively affect the absorption, distribution, biotransformation and excretion of the compound. While the route of administration of the pharmaceutical composition is important, and various anatomical, physiological and pathological factors can critically affect bioavailability, the solubility of the compound is usually dependent upon the character of the particular salt form thereof, which it utilized. One of skill in the art will appreciate that an aqueous solution of the compound will provide the most rapid absorption of the compound into the body of a subject being treated, while lipid solutions and suspensions, as well as solid dosage forms, will result in less rapid absorption of the compound.

Compositions Comprising MEK Inhibitors

A wide variety of compositions and administration methods may be used in conjunction with the compounds of the present invention. Such compositions may include, in addition to the compounds of the present invention, conventional pharmaceutical excipients, and other conventional, pharmaceutically inactive agents. Additionally, the compositions may include active agents in addition to the compounds of the present invention. These additional active agents may include additional compounds according to the invention, and/or one or more other pharmaceutically active agents.

The compositions may be in gaseous, liquid, semi-liquid or solid form, formulated in a manner suitable for the route of administration to be used. For oral administration, capsules and tablets are typically used. For parenteral administration, reconstitution of a lyophilized powder, prepared as described herein, is typically used.

Compositions comprising compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds and/or compositions according to the invention may also be administered or coadministered in slow release dosage forms.

The MEK inhibitors and compositions comprising them may be administered or coadministered in any conventional dosage form. Co-administration in the context of this invention is intended to mean the administration of more than one therapeutic agent, one of which includes a MEK inhibitor, in the course of a coordinated treatment to achieve an improved clinical outcome. Such co-administration may also be coextensive, that is, occurring during overlapping periods of time.

Solutions or suspensions used for parenteral, intradermal, subcutaneous, or topical application may optionally include one or more of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; agents for the adjustment of tonicity such as sodium chloride or dextrose, and agents for adjusting the acidity or alkalinity of the composition, such as alkaline or acidifying agents or buffers like carbonates, bicarbonates, phosphates, hydrochloric acid, and organic acids like acetic and citric acid. Parenteral preparations may optionally be enclosed in ampules, disposable syringes or single or multiple dose vials made of glass, plastic or other suitable material.

When compounds according to the present invention exhibit insufficient solubility, methods for solubilizing the compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate. Derivatives of the compounds, such as prodrugs of the compounds may also be used in formulating effective pharmaceutical compositions.

Upon mixing or adding compounds according to the present invention to a composition, a solution, suspension, emulsion or the like may be formed. The form of the resulting composition will depend upon a number of factors, including the intended mode of administration, and the solubility of the compound in the selected carrier or vehicle. The effective concentration needed to ameliorate the disease being treated may be empirically determined.

Compositions according to the present invention are optionally provided for administration to humans and animals in unit dosage forms, such as tablets, capsules, pills, powders, dry powders for inhalers, granules, sterile parenteral solutions or suspensions, and oral solutions or suspensions, and oil-water emulsions containing suitable quantities of the compounds, particularly the pharmaceutically acceptable salts, preferably the sodium salts, thereof. The pharmaceutically therapeutically active compounds and derivatives thereof are typically formulated and administered in unit-dosage forms or multiple-dosage forms. Unit-dose forms, as used herein, refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes individually packaged tablet or capsule. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pint or gallons. Hence, multiple dose form is a multiple of unit-doses that are not segregated in packaging.

In addition to one or more compounds according to the present invention, the composition may comprise: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to form a solution or suspension. If desired, the pharmaceutical composition to be administered may also contain minor amounts of auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known in the art, or will be apparent, to those skilled in this art; for example, see Remington's Pharmaceutical Sciences, Mack Publishing Company, Easton, Pa., 15th Edition, 1975. The composition or formulation to be administered will, in any event, contain a sufficient quantity of a inhibitor of the present invention to reduce MEK activity in vivo, thereby treating the disease state of the subject.

Dosage forms or compositions may optionally comprise one or more compounds according to the present invention in the range of 0.005% to 100% (weight/weight) with the balance comprising additional substances such as those described herein. For oral administration, a pharmaceutically acceptable composition may optionally comprise any one or more commonly employed excipients, such as, for example pharmaceutical grades of mannitol, lactose, starch, magnesium stearate, talcum, cellulose derivatives, sodium crosscarmellose, glucose, sucrose, magnesium carbonate, sodium saccharin, talcum. Such compositions include solutions, suspensions, tablets, capsules, powders, dry powders for inhalers and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparing these formulations are known to those skilled in the art. The compositions may optionally contain 0.01%-100% (weight/weight) of one or more MEK inhibitors, optionally 0.1-95%, and optionally 1-95%.

Salts, preferably sodium salts, of the inhibitors may be prepared with carriers that protect the compound against rapid elimination from the body, such as time release formulations or coatings. The formulations may further include other active compounds to obtain desired combinations of properties.

Formulations for Oral Administration

Oral pharmaceutical dosage forms may be as a solid, gel or liquid. Examples of solid dosage forms include, but are not limited to tablets, capsules, granules, and bulk powders. More specific examples of oral tablets include compressed, chewable lozenges and tablets that may be enteric-coated, sugar-coated or film-coated. Examples of capsules include hard or soft gelatin capsules. Granules and powders may be provided in non-effervescent or effervescent forms. Each may be combined with other ingredients known to those skilled in the art.

In certain embodiments, compounds according to the present invention are provided as solid dosage forms, preferably capsules or tablets. The tablets, pills, capsules, troches and the like may optionally contain one or more of the following ingredients, or compounds of a similar nature: a binder; a diluent; a disintegrating agent; a lubricant; a glidant; a sweetening agent; and a flavoring agent.

Examples of binders that may be used include, but are not limited to, microcrystalline cellulose, gum tragacanth, glucose solution, acacia mucilage, gelatin solution, sucrose and starch paste.

Examples of lubricants that may be used include, but are not limited to, talc, starch, magnesium or calcium stearate, *lycopodium* and stearic acid.

Examples of diluents that may be used include, but are not limited to, lactose, sucrose, starch, kaolin, salt, mannitol and dicalcium phosphate.

Examples of glidants that may be used include, but are not limited to, colloidal silicon dioxide.

Examples of disintegrating agents that may be used include, but are not limited to, crosscarmellose sodium, sodium starch glycolate, alginic acid, corn starch, potato starch, bentonite, methylcellulose, agar and carboxymethylcellulose.

Examples of coloring agents that may be used include, but are not limited to, any of the approved certified water-soluble FD and C dyes, mixtures thereof, and water insoluble FD and C dyes suspended on alumina hydrate.

Examples of sweetening agents that may be used include, but are not limited to, sucrose, lactose, mannitol and artificial sweetening agents such as sodium cyclamate and saccharin, and any number of spray-dried flavors.

Examples of flavoring agents that may be used include, but are not limited to, natural flavors extracted from plants such as fruits and synthetic blends of compounds that produce a pleasant sensation, such as, but not limited to peppermint and methyl salicylate.

Examples of wetting agents that may be used include, but are not limited to, propylene glycol monostearate, sorbitan monooleate, diethylene glycol monolaurate and polyoxyethylene lauryl ether.

Examples of anti-emetic coatings that may be used include, but are not limited to, fatty acids, fats, waxes, shellac, ammoniated shellac and cellulose acetate phthalates.

Examples of film coatings that may be used include, but are not limited to, hydroxyethylcellulose, sodium carboxymethylcellulose, polyethylene glycol 4000 and cellulose acetate phthalate.

If oral administration is desired, the salt of the compound may optionally be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it may optionally additionally comprise a liquid carrier such as a fatty oil. In addition, dosage unit forms may optionally additionally comprise various other materials that modify the physical form of the dosage unit, for example, coatings of sugar and other enteric agents.

Compounds according to the present invention may also be administered as a component of an elixir, suspension, syrup, wafer, sprinkle, chewing gum or the like. A syrup may optionally comprise, in addition to the active compounds, sucrose as a sweetening agent and certain preservatives, dyes and colorings and flavors.

The compounds of the present invention may also be mixed with other active materials that do not impair the desired action, or with materials that supplement the desired action, such as antacids, H2 blockers, and diuretics. For example, if a compound is used for treating asthma or hypertension, it may be used with other bronchodilators and antihypertensive agents, respectively.

Examples of pharmaceutically acceptable carriers that may be included in tablets comprising compounds of the present invention include, but are not limited to binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets may be compressed tablets to which different layers of pharmaceutically acceptable substances are applied. Film-coated tablets may be compressed tablets that have been coated with polymers or other suitable coating. Multiple compressed tablets may be compressed tablets made by more than one compression cycle utilizing the pharmaceutically acceptable substances previously mentioned. Coloring agents may also be used in tablets. Flavoring and sweetening agents may be used in tablets, and are especially useful in the formation of chewable tablets and lozenges.

Examples of liquid oral dosage forms that may be used include, but are not limited to, aqueous solutions, emulsions, suspensions, solutions and/or suspensions reconstituted from non-effervescent granules and effervescent preparations reconstituted from effervescent granules.

Examples of aqueous solutions that may be used include, but are not limited to, elixirs and syrups. As used herein, elixirs refer to clear, sweetened, hydroalcoholic preparations. Examples of pharmaceutically acceptable carriers that may be used in elixirs include, but are not limited to solvents. Particular examples of solvents that may be used include glycerin, sorbitol, ethyl alcohol and syrup. As used herein, syrups refer to concentrated aqueous solutions of a sugar, for example, sucrose. Syrups may optionally further comprise a preservative.

Emulsions refer to two-phase systems in which one liquid is dispersed in the form of small globules throughout another liquid. Emulsions may optionally be oil-in-water or water-in-oil emulsions. Examples of pharmaceutically acceptable carriers that may be used in emulsions include, but are not limited to non-aqueous liquids, emulsifying agents and preservatives.

Examples of pharmaceutically acceptable substances that may be used in non-effervescent granules, to be reconstituted into a liquid oral dosage form, include diluents, sweeteners and wetting agents.

Examples of pharmaceutically acceptable substances that may be used in effervescent granules, to be reconstituted into a liquid oral dosage form, include organic acids and a source of carbon dioxide.

Coloring and flavoring agents may optionally be used in all of the above dosage forms.

Particular examples of preservatives that may be used include glycerin, methyl and propylparaben, benzoic add, sodium benzoate and alcohol.

Particular examples of non-aqueous liquids that may be used in emulsions include mineral oil and cottonseed oil.

Particular examples of emulsifying agents that may be used include gelatin, acacia, tragacanth, bentonite, and surfactants such as polyoxyethylene sorbitan monooleate.

Particular examples of suspending agents that may be used include sodium carboxymethylcellulose, pectin, tragacanth, Veegum and acacia. Diluents include lactose and Particular examples of wetting agents that may be used include propylene glycol monostearate, sorbitan monooleate, diethylene glycol monolaurate and polyoxyethylene lauryl ether.

Particular examples of organic acids that may be used include citric and tartaric acid.

Sources of carbon dioxide that may be used in effervescent compositions include sodium bicarbonate and sodium carbonate. Coloring agents include any of the approved certified water soluble FD and C dyes, and mixtures thereof.

Particular examples of flavoring agents that may be used include natural flavors extracted from plants such fruits, and synthetic blends of compounds that produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603.

Injectables, Solutions, and Emulsions

The present invention is also directed to compositions designed to administer the compounds of the present invention by parenteral administration, generally characterized by subcutaneous, intramuscular or intravenous injection. Injectables may be prepared in any conventional form, for example as liquid solutions or suspensions, solid forms suitable for solution or suspension in liquid prior to injection, or as emulsions.

Examples of excipients that may be used in conjunction with injectables according to the present invention include, but are not limited to water, saline, dextrose, glycerol or ethanol. The injectable compositions may also optionally comprise minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. The percentage of active compound contained in such parenteral compositions is highly dependent on the specific nature thereof, as well as the activity of the compound and the needs of the subject.

Parenteral administration of the formulations includes intravenous, subcutaneous and intramuscular administrations. Preparations for parenteral administration include sterile solutions ready for injection, sterile dry soluble products, such as the lyophilized powders described herein, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

When administered intravenously, examples of suitable carriers include, but are not limited to physiological saline or phosphate buffered saline (PBS), and solutions containing thickening and solubilizing agents, such as glucose, polyethylene glycol, and polypropylene glycol and mixtures thereof.

Examples of pharmaceutically acceptable carriers that may optionally be used in parenteral preparations include, but are not limited to aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles that may optionally be used include Sodium Chloride Injection, Ringers Injection, Isotonic Dextrose Injection, Sterile Water Injection, Dextrose and Lactated Ringers Injection.

Examples of nonaqueous parenteral vehicles that may optionally be used include fixed oils of vegetable origin, cottonseed oil, corn oil, sesame oil and peanut oil.

Antimicrobial agents in bacteriostatic or fungistatic concentrations may be added to parenteral preparations, particularly when the preparations are packaged in multiple-dose containers and thus designed to be stored and multiple aliquots to be removed. Examples of antimicrobial agents that may be used include phenols or cresols, mercurials, benzyl alcohol, chlorobutanol, methyl and propyl p-hydroxybenzoic acid esters, thimerosal, benzalkonium chloride and benzethonium chloride.

Examples of isotonic agents that may be used include sodium chloride and dextrose. Examples of buffers that may be used include phosphate and citrate. Examples of antioxidants that may be used include sodium bisulfate. Examples of local anesthetics that may be used include procaine hydrochloride. Examples of suspending and dispersing agents that may be used include sodium carboxymethylcellulose, hydroxypropyl methylcellulose and polyvinylpyrrolidone. Examples of emulsifying agents that may be used include Polysorbate 80 (TWEEN 80). A sequestering or chelating agent of metal ions includes EDTA.

Pharmaceutical carriers may also optionally include ethyl alcohol, polyethylene glycol and propylene glycol for water miscible vehicles and sodium hydroxide, hydrochloric acid, citric acid or lactic acid for pH adjustment.

The concentration of an inhibitor in the parenteral formulation may be adjusted so that an injection administers a pharmaceutically effective amount sufficient to produce the desired pharmacological effect. The exact concentration of an inhibitor and/or dosage to be used will ultimately depend on the age, weight and condition of the patient or animal as is known in the art.

Unit-dose parenteral preparations may be packaged in an ampoule, a vial or a syringe with a needle. All preparations for parenteral administration should be sterile, as is know and practiced in the art.

Injectables may be designed for local and systemic administration. Typically a therapeutically effective dosage is formulated to contain a concentration of at least about 0.1% w/w up to about 90% w/w or more, preferably more than 1% w/w of the MEK inhibitor to the treated tissue(s). The inhibitor may be administered at once, or may be divided into a number of smaller doses to be administered at intervals of time. It is understood that the precise dosage and duration of treatment will be a function of the location of where the composition is parenterally administered, the carrier and other variables that may be determined empirically using known testing protocols or by extrapolation from in vivo or in vitro test data. It is to be noted that concentrations and dosage values may also vary with the age of the individual treated. It is to be further understood that for any particular subject, specific dosage regimens may need to be adjusted over time according to the individual need and the professional judgment of the person administering or supervising the administration of the formulations. Hence, the concentration ranges set forth herein are intended to be exemplary and are not intended to limit the scope or practice of the claimed formulations.

The MEK inhibitor may optionally be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the disease state and may be empirically determined.

Lyophilized Powders

The compounds of the present invention may also be prepared as lyophilized powders, which can be reconstituted for administration as solutions, emulsions and other mixtures. The lyophilized powders may also be formulated as solids or gels.

Sterile, lyophilized powder may be prepared by dissolving the compound in a sodium phosphate buffer solution containing dextrose or other suitable excipient. Subsequent sterile filtration of the solution followed by lyophilization under standard conditions known to those of skill in the art provides the desired formulation. Briefly, the lyophilized powder may optionally be prepared by dissolving dextrose, sorbitol, fructose, corn syrup, xylitol, glycerin, glucose, sucrose or other suitable agent, about 1-20%, preferably about 5 to 15%, in a suitable buffer, such as citrate, sodium or potassium phosphate or other such buffer known to those of skill in the art at, typically, about neutral pH. Then, a MEK inhibitor is added to the resulting mixture, preferably above room temperature, more preferably at about 30-35° C., and stirred until it dissolves. The resulting mixture is diluted by adding more buffer to a desired concentration. The resulting mixture is sterile filtered or treated to remove particulates and to insure sterility, and apportioned into vials for lyophilization. Each vial may contain a single dosage or multiple dosages of the inhibitor.

Topical Administration

The compounds of the present invention may also be administered as topical mixtures. Topical mixtures may be used for local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The MEK inhibitors may be formulated as aerosols for topical application, such as by inhalation (see, U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

The inhibitors may also be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the MEK inhibitor alone or in combination with other pharmaceutically acceptable excipients can also be administered.

Formulations for Other Routes of Administration

Depending upon the disease state being treated, other routes of administration, such as topical application, transdermal patches, and rectal administration, may also be used. For example, pharmaceutical dosage forms for rectal administration are rectal suppositories, capsules and tablets for systemic effect. Rectal suppositories are used herein mean solid bodies for insertion into the rectum that melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax, (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm. Tablets and capsules for rectal administration may be manufactured using the same pharmaceutically acceptable substance and by the same methods as for formulations for oral administration.

Examples of Formulations

The following are particular examples of oral, intravenous and tablet formulations that may optionally be used with compounds of the present invention. It is noted that these formulations may be varied depending on the particular compound being used and the indication for which the formulation is going to be used.

| ORAL FORMULATION | |
|---|---|
| Compound of the Present Invention | 10-100 mg |
| Citric Acid Monohydrate | 105 mg |
| Sodium Hydroxide | 18 mg |
| Flavoring | |
| Water | q.s. to 100 mL |
| INTRAVENOUS FORMULATION | |
| Compound of the Present Invention | 0.1-10 mg |
| Dextrose Monohydrate | q.s. to make isotonic |
| Citric Acid Monohydrate | 1.05 mg |
| Sodium Hydroxide | 0.18 mg |
| Water for Injection | q.s. to 1.0 mL |
| TABLET FORMULATION | |
| Compound of the Present Invention | 1% |
| Microcrystalline Cellulose | 73% |
| Stearic Acid | 25% |
| Colloidal Silica | 1% |

Kits Comprising MEK Inhibitors

The invention is also directed to kits and other articles of manufacture for treating diseases associated with MEK. It is noted that diseases are intended to cover all conditions for which the MEK possess activity that contributes to the pathology and/or symptomology of the condition.

In one embodiment, a kit is provided that comprises a composition comprising at least one inhibitor of the present invention in combination with instructions. The instructions may indicate the disease state for which the composition is to be administered, storage information, dosing information and/or instructions regarding how to administer the composition. The kit may also comprise packaging materials. The packaging material may comprise a container for housing the composition. The kit may also optionally comprise additional components, such as syringes for administration of the composition. The kit may comprise the composition in single or multiple dose forms.

In another embodiment, an article of manufacture is provided that comprises a composition comprising at least one inhibitor of the present invention in combination with packaging materials. The packaging material may comprise a container for housing the composition. The container may optionally comprise a label indicating the disease state for which the composition is to be administered, storage information, dosing information and/or instructions regarding how to administer the composition. The kit may also optionally comprise additional components, such as syringes for administration of the composition. The kit may comprise the composition in single or multiple dose forms.

It is noted that the packaging material used in kits and articles of manufacture according to the present invention may form a plurality of divided containers such as a divided bottle or a divided foil packet. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container that is employed will depend on the exact dosage form involved, for example a conventional cardboard box would not generally be used to hold a liquid suspension. It is feasible that more than one container can be used together in a single package to market a single dosage form. For example, tablets may be contained in a bottle that is in turn contained within a box. Typically the kit includes directions for the administration of the separate components. The kit form is particularly advantageous when the separate components are preferably administered in different dosage forms (e.g., oral, topical, transdermal and parenteral), are administered at different dosage intervals, or when titration of the individual components of the combination is desired by the prescribing physician.

One particular example of a kit according to the present invention is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

Another specific embodiment of a kit is a dispenser designed to dispense the daily doses one at a time in the order of their intended use. Preferably, the dispenser is equipped with a memory-aid, so as to further facilitate compliance with the regimen. An example of such a memory-aid is a mechanical counter that indicates the number of daily doses that has been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

Dosage, Host and Safety

The compounds of the present invention are stable and can be used safely. In particular, the compounds of the present invention are useful as MEK inhibitors for a variety of subjects (e.g., humans, non-human mammals and non-mammals). The optimal dose may vary depending upon such conditions as, for example, the type of subject, the body weight of the subject, the route of administration, and specific properties of the particular compound being used. In general, the daily dose for oral administration to an adult (body weight of about 60 kg) is about 1 to 1000 mg, about 3 to 300 mg, or about 10 to 200 mg. It will be appreciated that the daily dose can be given in a single administration or in multiple (e.g., 2 or 3) portions a day.

Combination Therapies

A wide variety therapeutic agents may have a therapeutic additive or synergistic effect with MEK inhibitors according to the present invention. Such therapeutic agents may additively or synergistically combine with the MEK inhibitors to inhibit undesirable cell growth, such as inappropriate cell growth resulting in undesirable benign conditions or tumor growth.

In one embodiment, a method is provided for treating a cell proliferative disease state comprising treating cells with a compound according to the present invention in combination with an anti-proliferative agent, wherein the cells are treated with the compound according to the present invention before, at the same time, and/or after the cells are treated with the anti-proliferative agent, referred to herein as combination therapy. It is noted that treatment of one agent before another is referred to herein as sequential therapy, even if the agents are also administered together. It is noted that combination therapy is intended to cover when agents are administered before or after each other (sequential therapy) as well as when the agents are administered at the same time.

Examples of therapeutic agents that may be used in combination with MEK inhibitors include, but are not limited to, anticancer agents, alkylating agents, antibiotic agents, antimetabolic agents, hormonal agents, plant-derived agents, and biologic agents.

Alkylating agents are polyfunctional compounds that have the ability to substitute alkyl groups for hydrogen ions. Examples of alkylating agents include, but are not limited to, bischloroethylamines (nitrogen mustards, e.g. chlorambucil, cyclophosphamide, ifosfamide, mechlorethamine, melphalan, uracil mustard), aziridines (e.g. thiotepa), alkyl alkone sulfonates (e.g. busulfan), nitrosoureas (e.g. carmustine, lomustine, streptozocin), nonclassic alkylating agents (altretamine, dacarbazine, and procarbazine), platinum compounds (carboplastin and cisplatin). These compounds react with phosphate, amino, hydroxyl, sulfihydryl, carboxyl, and imidazole groups. Under physiological conditions, these drugs ionize and produce positively charged ion that attach to susceptible nucleic acids and proteins, leading to cell cycle arrest and/or cell death. Combination therapy including a MEK inhibitor and an alkylating agent may have therapeutic synergistic effects on cancer and reduce sides affects associated with these chemotherapeutic agents.

Antibiotic agents are a group of drugs that produced in a manner similar to antibiotics as a modification of natural products. Examples of antibiotic agents include, but are not limited to, anthracyclines (e.g. doxorubicin, daunorubicin, epirubicin, idarubicin and anthracenedione), mitomycin C, bleomycin, dactinomycin, plicatomycin. These antibiotic agents interfere with cell growth by targeting different cellular components. For example, anthracyclines are generally believed to interfere with the action of DNA topoisomerase II in the regions of transcriptionally active DNA, which leads to DNA strand scissions. Bleomycin is generally believed to chelate iron and forms an activated complex, which then binds to bases of DNA, causing strand scissions and cell death. Combination therapy including a MEK inhibitor and an antibiotic agent may have therapeutic synergistic effects on cancer and reduce sides affects associated with these chemotherapeutic agents.

Antimetabolic agents are a group of drugs that interfere with metabolic processes vital to the physiology and proliferation of cancer cells. Actively proliferating cancer cells require continuous synthesis of large quantities of nucleic acids, proteins, lipids, and other vital cellular constituents. Many of the antimetabolites inhibit the synthesis of purine or pyrimidine nucleosides or inhibit the enzymes of DNA replication. Some antimetabolites also interfere with the synthesis of ribonucleosides and RNA and/or amino acid metabolism and protein synthesis as well. By interfering with the synthesis of vital cellular constituents, antimetabolites can delay or arrest the growth of cancer cells. Examples of antimetabolic agents include, but are not limited to, fluorouracil (5-FU), floxuridine (5-FUdR), methotrexate, leucovorin, hydroxyurea, thioguanine (6-TG), mercaptopurine (6-MP), cytarabine, pentostatin, fludarabine phosphate, cladribine (2-CDA), asparaginase, and gemcitabine. Combination therapy including a MEK inhibitor and a antimetabolic agent may have therapeutic synergistic effects on cancer and reduce sides affects associated with these chemotherapeutic agents.

Hormonal agents are a group of drug that regulate the growth and development of their target organs. Most of the hormonal agents are sex steroids and their derivatives and analogs thereof, such as estrogens, androgens, and progestins. These hormonal agents may serve as antagonists of receptors for the sex steroids to down regulate receptor expression and transcription of vital genes. Examples of such hormonal agents are synthetic estrogens (e.g. diethylstibestrol), antiestrogens (e.g. tamoxifen, toremifene, fluoxymesterol and raloxifene), antiandrogens (bicalutamide, nilutamide, flutamide), aromatase inhibitors (e.g., aminoglutethimide, anastrozole and tetrazole), ketoconazole, goserelin acetate, leuprolide, megestrol acetate and mifepristone. Combination therapy including a MEK inhibitor and a hormonal agent may have therapeutic synergistic effects on cancer and reduce sides affects associated with these chemotherapeutic agents.

Plant-derived agents are a group of drugs that are derived from plants or modified based on the molecular structure of the agents. Examples of plant-derived agents include, but are not limited to, vinca alkaloids (e.g., vincristine, vinblastine, vindesine, vinzolidine and vinorelbine), podophyllotoxins (e.g., etoposide (VP-16) and teniposide (VM-26)), taxanes (e.g., paclitaxel and docetaxel). These plant-derived agents generally act as antimitotic agents that bind to tubulin and inhibit mitosis. Podophyllotoxins such as etoposide are believed to interfere with DNA synthesis by interacting with topoisomerase TI, leading to DNA strand scission. Combination therapy including a MEK inhibitor and a plant-derived agent may have therapeutic synergistic effects on cancer and reduce sides affects associated with these chemotherapeutic agents.

Biologic agents are a group of biomolecules that elicit cancer/tumor regression when used alone or in combination with chemotherapy and/or radiotherapy. Examples of biologic agents include, but are not limited to, immuno-modulating proteins such as cytokines, monoclonal antibodies against tumor antigens, tumor suppressor genes, and cancer vaccines. Combination therapy including a MEK inhibitor and a biologic agent may have therapeutic synergistic effects on cancer, enhance the patient's immune responses to tumorigenic signals, and reduce potential sides affects associated with this chemotherapeutic agent.

Cytokines possess profound immunomodulatory activity. Some cytokines such as interleukin-2 (IL-2, aldesleukin) and interferon have demonstrated antitumor activity and have been approved for the treatment of patients with metastatic renal cell carcinoma and metastatic malignant melanoma. IL-2 is a T-cell growth factor that is central to T-cell-mediated immune responses. The selective antitumor effects of IL-2 on some patients are believed to be the result of a cell-mediated immune response that discriminate between self and nonself. Examples of interleukins that may be used in conjunction with MEK inhibitor include, but are not limited to, interleukin 2 (IL-2), and interleukin 4 (IL-4), interleukin 12 (IL-12).

Interferon include more than 23 related subtypes with overlapping activities, all of the IFN subtypes within the scope of the present invention. IFN has demonstrated activity against many solid and hematologic malignancies, the later appearing to be particularly sensitive.

Other cytokines that may be used in conjunction with a MEK inhibitor include those cytokines that exert profound effects on hematopoiesis and immune functions. Examples of such cytokines include, but are not limited to erythropoietin, granulocyte-CSF (filgrastin), and granulocyte, macrophage-CSF (sargramostim). These cytokines may be used in conjunction with a MEK inhibitor to reduce chemotherapy-induced myelopoietic toxicity.

Other immuno-modulating agents other than cytokines may also be used in conjunction with a MEK inhibitor to inhibit abnormal cell growth. Examples of such immuno-modulating agents include, but are not limited to bacillus Calmette-Guerin, levamisole, and octreotide, a long-acting octapeptide that mimics the effects of the naturally occurring hormone somatostatin.

Monoclonal antibodies against tumor antigens are antibodies elicited against antigens expressed by tumors, preferably tumor-specific antigens. For example, monoclonal antibody HERCEPTIN® (Trastruzumab) is raised against human epidermal growth factor receptor2 (HER2) that is overexpressed in some breast tumors including metastatic breast cancer. Overexpression of HER2 protein is associated with more aggressive disease and poorer prognosis in the clinic. HERCEPTIN® is used as a single agent for the treatment of patients with metastatic breast cancer whose tumors over express the HER2 protein. Combination therapy including MEK inhibitor and HERCEPTIN® may have therapeutic synergistic effects on tumors, especially on metastatic cancers.

Another example of monoclonal antibodies against tumor antigens is RITUXAN® (Rituximab) that is raised against CD20 on lymphoma cells and selectively deplete normal and malignant $CD20^+$ pre-B and mature B cells. RITUXAN® is used as single agent for the treatment of patients with relapsed or refractory low-grade or follicular, CD20+, B cell non-Hodgkin's lymphoma. Combination therapy including MEK inhibitor and RITUXAN® may have therapeutic synergistic effects not only on lymphoma, but also on other forms or types of malignant tumors.

Tumor suppressor genes are genes that function to inhibit the cell growth and division cycles, thus preventing the development of neoplasia. Mutations in tumor suppressor genes cause the cell to ignore one or more of the components of the network of inhibitory signals, overcoming the cell cycle check points and resulting in a higher rate of controlled cell growth-cancer. Examples of the tumor suppressor genes include, but are not limited to, DPC-4, NF-1, NF-2, RB, p53, WT1, BRCA1 and BRCA2.

DPC-4 is involved in pancreatic cancer and participates in a cytoplasmic pathway that inhibits cell division. NF-1 codes for a protein that inhibits Ras, a cytoplasmic inhibitory protein. NF-1 is involved in neurofibroma and pheochromocytomas of the nervous system and myeloid leukemia. NF-2 encodes a nuclear protein that is involved in meningioma, schwanoma, and ependymoma of the nervous system. RB codes for the pRB protein, a nuclear protein that is a major inhibitor of cell cycle. RB is involved in retinoblastoma as well as bone, bladder, small cell lung and breast cancer. P53 codes for p53 protein that regulates cell division and can induce apoptosis. Mutation and/or inaction of p53 is found in a wide ranges of cancers. WT1 is involved in Wilms tumor of the kidneys. BRCA1 is involved in breast and ovarian cancer, and BRCA2 is involved in breast cancer. The tumor suppressor gene can be transferred into the tumor cells where it exerts its tumor suppressing functions. Combination therapy including a MEK inhibitor and a tumor suppressor may have therapeutic synergistic effects on patients suffering from various forms of cancers.

Cancer vaccines are a group of agents that induce the body's specific immune response to tumors. Most of cancer vaccines under research and development and clinical trials are tumor-associated antigens (TAAs). TAA are structures (i.e. proteins, enzymes or carbohydrates) which are present on tumor cells and relatively absent or diminished on normal cells. By virtue of being fairly unique to the tumor cell, TAAs provide targets for the immune system to recognize and cause their destruction. Example of TAAs include, but are not limited to gangliosides (GM2), prostate specific antigen (PSA), alpha-fetoprotein (AFP), carcinoembryonic antigen (CEA)

(produced by colon cancers and other adenocarcinomas, e.g. breast, lung, gastric, and pancreas cancer s), melanoma associated antigens (MART-1, gp 100, MAGE 1,3 tyrosinase), papillomavirus E6 and E7 fragments, whole cells or portions/lysates of antologous tumor cells and allogeneic tumor cells.

An adjuvant may be used to augment the immune response to TAAs. Examples of adjuvants include, but are not limited to, *bacillus* Calmette-Guerin (BCG), endotoxin lipopolysaccharides, keyhole limpet hemocyanin (GKLH), interleukin-2 (IL-2), granulocyte-macrophage colony-stimulating factor (GM-CSF) and cytoxan, a chemotherapeutic agent which is believe to reduce tumor-induced suppression when given in low doses.

Further examples of therapeutic agents that may be used in combination with MEK inhibitors include, but are not limited to, P13/Akt signaling inhibitors. Examples of P13/Akt inhibitors that may be used in combination with MEK inhibitors include, but are not limited to, human epidermal growth factor receptor (HER2) inhibitors. Examples of HER2 inhibitors include, but are not limited to, Herceptin® (Trastruzumab) and Tykerb® (Lapatinib). Tykerb®, a small molecule that can be administered orally, inhibits the tyrosine kinase components of ErbB1 and ErbB2 receptors. Stimulation of ErbB1 and ErbB2 is associated with cell proliferation and with multiple processes involved in tumor progression, invasion, and metastasis. Overexpression of these receptors has been reported in a variety of human tumors and is associated with poor prognosis and reduced overall survival.

Still further examples of therapeutic agents that may be used in combination with MEK inhibitors include, but are not limited to, histone deacetylase (HDAC) inhibitors. Examples of HDAC inhibitors that may be used in combination with MEK inhibitors include, but are not limited to, suberoylanilide hydroxamic acid (SAHA).

EXAMPLES

Preparation of MEK Inhibitors

Various methods may be developed for synthesizing compounds according to the present invention. Representative methods for synthesizing these compounds are provided in the Examples. It is noted, however, that the compounds of the present invention may also be synthesized by other synthetic routes that others may devise.

It will be readily recognized that certain compounds according to the present invention have atoms with linkages to other atoms that confer a particular stereochemistry to the compound (e.g., chiral centers). It is recognized that synthesis of compounds according to the present invention may result in the creation of mixtures of different stereoisomers (i.e., enantiomers and diastereomers). Unless a particular stereochemistry is specified, recitation of a compound is intended to encompass all of the different possible stereoisomers.

Various methods for separating mixtures of different stereoisomers are known in the art. For example, a racemic mixture of a compound may be reacted with an optically active resolving agent to form a pair of diastereoisomeric compounds. The diastereomers may then be separated in order to recover the optically pure enantiomers. Dissociable complexes may also be used to resolve enantiomers (e.g., crystalline diastereoisomeric salts). Diastereomers typically have sufficiently distinct physical properties (e.g., melting points, boiling points, solubilities, reactivity, etc.) and can be readily separated by taking advantage of these dissimilarities. For example, diastereomers can typically be separated by chromatography or by separation/resolution techniques based upon differences in solubility. A more detailed description of techniques that can be used to resolve stereoisomers of compounds from their racemic mixture can be found in Jean Jacques Andre Collet, Samuel H. Wilen, Enantiomers, Racemates and Resolutions, John Wiley & Sons, Inc. (1981).

Compounds according to the present invention can also be prepared as a pharmaceutically acceptable acid addition salt by reacting the free base form of the compound with a pharmaceutically acceptable inorganic or organic acid. Alternatively, a pharmaceutically acceptable base addition salt of a compound can be prepared by reacting the free acid form of the compound with a pharmaceutically acceptable inorganic or organic base. Inorganic and organic acids and bases suitable for the preparation of the pharmaceutically acceptable salts of compounds are set forth in the definitions section of this Application. Alternatively, the salt forms of the compounds can be prepared using salts of the starting materials or intermediates.

The free acid or free base forms of the compounds can be prepared from the corresponding base addition salt or acid addition salt form. For example, a compound in an acid addition salt form can be converted to the corresponding free base by treating with a suitable base (e.g., ammonium hydroxide solution, sodium hydroxide, and the like). A compound in a base addition salt form can be converted to the corresponding free acid by treating with a suitable acid (e.g., hydrochloric acid, etc).

The N-oxides of compounds according to the present invention can be prepared by methods known to those of ordinary skill in the art. For example, N-oxides can be prepared by treating an unoxidized form of the compound with an oxidizing agent (e.g., trifluoroperacetic acid, permaleic acid, perbenzoic acid, peracetic acid, meta-chloroperoxybenzoic acid, or the like) in a suitable inert organic solvent (e.g., a halogenated hydrocarbon such as dichloromethane) at approximately 0° C. Alternatively, the N-oxides of the compounds can be prepared from the N-oxide of an appropriate starting material.

Compounds in an unoxidized form can be prepared from N-oxides of compounds by treating with a reducing agent (e.g., sulfur, sulfur dioxide, triphenyl phosphine, lithium borohydride, sodium borohydride, phosphorus trichloride, tribromide, or the like) in an suitable inert organic solvent (e.g., acetonitrile, ethanol, aqueous dioxane, or the like) at 0 to 80° C.

Prodrug derivatives of the compounds can be prepared by methods known to those of ordinary skill in the art (e.g., for further details see Saulnier et al. (1994), Bioorganic and Medicinal Chemistry Letters, Vol. 4, p. 1985). For example, appropriate prodrugs can be prepared by reacting a non-derivatized compound with a suitable carbamylating agent (e.g., 1,1-acyloxyalkylcarbonochloridate, para-nitrophenyl carbonate, or the like).

Protected derivatives of the compounds can be made by methods known to those of ordinary skill in the art. A detailed description of the techniques applicable to the creation of protecting groups and their removal can be found in T. W. Greene, Protecting Groups in Organic Synthesis, $3^{rd}$ edition, John Wiley & Sons, Inc. 1999.

Compounds according to the present invention may be conveniently prepared, or formed during the process of the invention, as solvates (e.g., hydrates). Hydrates of compounds of the present invention may be conveniently prepared by recrystallization from an aqueous/organic solvent mixture, using organic solvents such as dioxin, tetrahydrofuran or methanol.

Compounds according to the present invention can also be prepared as their individual stereoisomers by reacting a racemic mixture of the compound with an optically active resolving agent to form a pair of diastereoisomeric compounds, separating the diastereomers and recovering the optically pure enantiomer. While resolution of enantiomers can be carried out using covalent diastereomeric derivatives of compounds, dissociable complexes are preferred (e.g., crystalline diastereoisomeric salts). Diastereomers have distinct physical properties (e.g., melting points, boiling points, solubilities, reactivity, etc.) and can be readily separated by taking advantage of these dissimilarities. The diastereomers can be separated by chromatography or, preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques Andre Collet, Samuel H. Wilen, Enantiomers, Racemates and Resolutions, John Wiley & Sons, Inc. (1981).

As used herein the symbols and conventions used in these processes, schemes and examples are consistent with those used in the contemporary scientific literature, for example, the Journal of the American Chemical Society or the Journal of Biological Chemistry. Standard single-letter or thee-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

| | |
|---|---|
| µL (microliters) | Ac (acetyl) |
| atm (atmosphere) | ATP (Adenosine Triphophatase) |
| BOC (tert-butyloxycarbonyl) | BOP (bis(2-oxo-3-oxazolidinyl)-phosphinic chloride) |
| BSA (Bovine Serum Albumin) | CBZ (benzyloxycarbonyl) |
| CDI (1,1-carbonyldiimidazole) | DCC (dicyclohexylcarbodiimide) |
| DCE (dichloroethane) | DCM (dichloromethane) |
| DMAP (4-dimethylaminopyridine) | DME (1,2-dimethoxyethane) |
| DMF (N,N-dimethylformamide) | DMPU (N,N'-dimethylpropyleneurea) |
| DMSO (dimethylsulfoxide) | EDCI (ethylcarbodiimide hydrochloride) |
| EDTA (Ethylenediaminetetraacetic acid) | Et (ethyl) |
| Et$_2$O (diethyl ether) | EtOAc (ethyl acetate) |
| FMOC (9-fluorenylmethoxycarbonyl) | g (grams) |
| h (hours) | HOAc or AcOH (acetic acid) |
| HOBT (1-hydroxybenzotriazole) | HOSu (N-hydroxysuccinimide) |
| HPLC (high pressure liquid chromatography) | Hz (Hertz) |
| i.v. (intravenous) | IBCF (isobutyl chloroformate) |
| i-PrOH (isopropanol) | L (liters) |
| M (molar) | mCPBA (meta-chloroperbenzoic acid) |
| Me (methyl) | MeOH (methanol) |
| mg (milligrams) | MHz (megahertz) |
| min (minutes) | mL (milliliters) |
| mM (millimolar) | mmol (millimoles) |
| mol (moles) | MOPS (Morpholinepropanesulfonic acid) |
| mp (melting point) | NaOAc (sodium acetate) |
| OMe (methoxy) | psi (pounds per square inch) |
| RP (reverse phase) | RT (ambient temperature) |
| SPA (Scintillation Proximity Assay) | TBAF (tetra-n-butylammonium fluoride) |

-continued

| | |
|---|---|
| TBS (t-butyldimethylsilyl) | tBu (tert-butyl) |
| TEA (triethylamine) | TFA (trifluoroacetic acid) |
| TFAA (trifluoroacetic anhydride) | THF (tetrahydrofuran) |
| TIPS (triisopropylsilyl) | TLC (thin layer chromatography) |
| TMS (trimethylsilyl) | TMSE (2-(trimethylsilyl)ethyl) |
| Tr (retention time) | |

All references to ether or Et$_2$O are to diethyl ether; and brine refers to a saturated aqueous solution of NaCl. Unless otherwise indicated, all temperatures are expressed in ° C. (degrees Centigrade). All reactions are conducted under an inert atmosphere at RT unless otherwise noted.

$^1$H NMR spectra were recorded on a Bruker Avance 400. Chemical shifts are expressed in parts per million (ppm). Coupling constants are in units of Hertz (Hz). Splitting patterns describe apparent multiplicities and are designated as s (singlet), d (doublet), t (triplet), q (quartet), m (multiplet), br (broad).

Low-resolution mass spectra (MS) and compound purity data were acquired on a Waters ZQ LC/MS single quadrupole system equipped with electrospray ionization (ESI) source, UV detector (220 and 254 nm), and evaporative light scattering detector (ELSD). Thin-layer chromatography was performed on 0.25 mm E. Merck silica gel plates (60F-254), visualized with UV light, 5% ethanolic phosphomolybdic acid, Ninhydrin or p-anisaldehyde solution. Flash column chromatography was performed on silica gel (230-400 mesh, Merck).

The starting materials and reagents used in preparing these compounds are either available from commercial suppliers such as the Aldrich Chemical Company (Milwaukee, Wis.), Bachem (Torrance, Calif.), Sigma (St. Louis, Mo.), or may be prepared by methods well known to a person of ordinary skill in the art, following procedures described in such standard references as Fieser and Fieser's Reagents for Organic Synthesis, vols. 1-17, John Wiley and Sons, New York, N.Y., 1991; Rodd's Chemistry of Carbon Compounds, vols. 1-5 and supps., Elsevier Science Publishers, 1989; Organic Reactions, vols. 1-40, John Wiley and Sons, New York, N.Y., 1991; March J.: Advanced Organic Chemistry, 4th ed., John Wiley and Sons, New York, N.Y.; and Larock: Comprehensive Organic Transformations, VCH Publishers, New York, 1989.

The entire disclosures of all documents cited throughout this application are incorporated herein by reference.

Synthetic Schemes for Compounds of the Present Invention

Compounds according to the present invention may be synthesized according to the reaction schemes shown below. Other reaction schemes could be readily devised by those skilled in the art. It should also be appreciated that a variety of different solvents, temperatures and other reaction conditions can be varied to optimize the yields of the reactions.

In the reactions described hereinafter it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in "Protective Groups in Organic Chemistry" John Wiley and Sons, 1991.

Scheme 1:

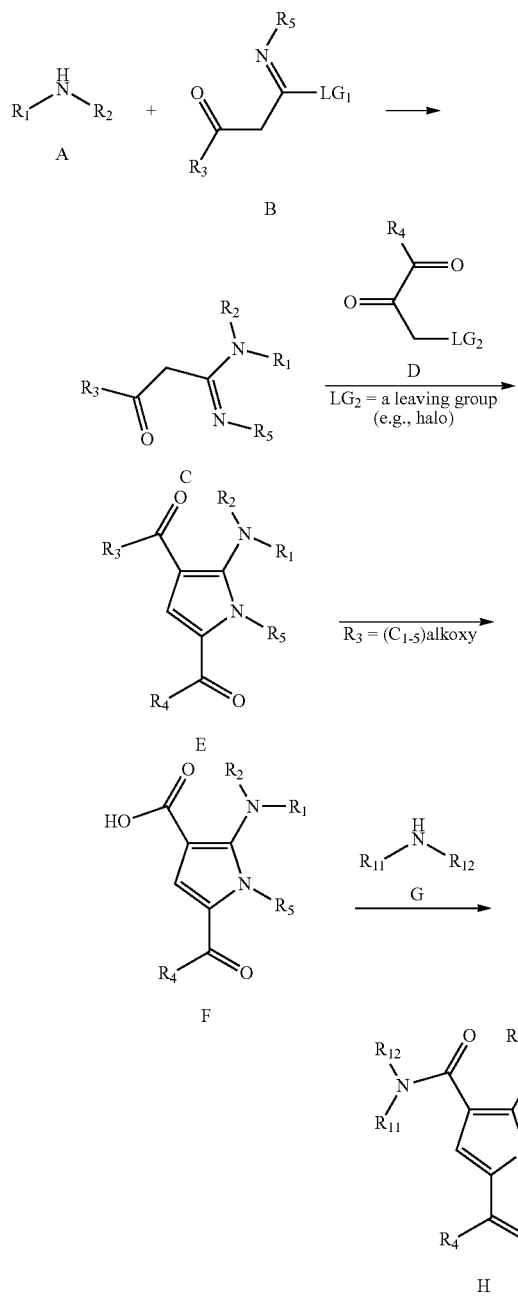

Scheme 2:

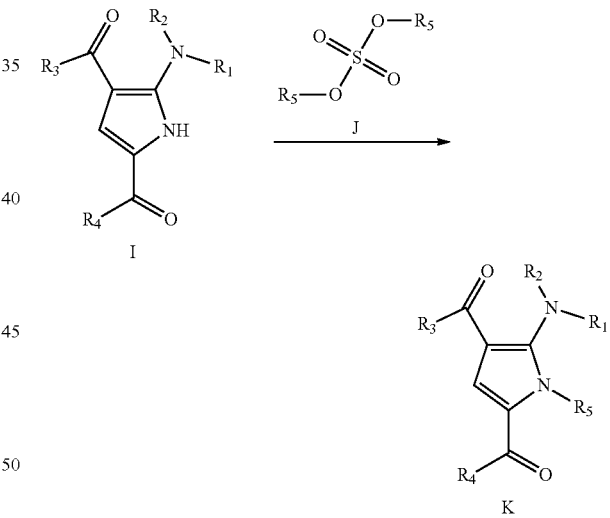

A general synthetic route for producing compounds of the present invention is shown in Scheme 1. Compound A is reacted with Compound B in any of a variety of solvents including, for example, EtOAc (see, Danswan et al., *J. Heterocyclic Chem.*, 26, 1989, 293-299). The resulting mixture is optionally stirred at reflux for 30 minutes or more, and optionally concentrated in vacuo. Compound C is isolated by dissolving the residue in a solvent (e.g., ether) and collecting the precipitate. In addition, Compound C is optionally purified using any of a variety of purification techniques known in the art, including column chromatography.

Compound C is then mixed with Compound D in any of a variety of solvents including, for example, THF (see, Matulennko et al, *Bioorg. Med. Chem.*, 13, 2005, 3705-3720). The resulting mixture is then optionally stirred at room temperature for 4 hours or more, and then optionally heated at reflux for 1 hour or more. The solution is then concentrated in vacuo and the residue dissolved (e.g., in $CH_2Cl_2$). Compound E is isolated by washing the organic layer with an acid (e.g., 0.1N HCl) and brine, drying (e.g., $MgSO_4$), and concentrating. Compound E is optionally purified using any of a variety of purification techniques known in the art, including silica gel chromatography.

When $R_3$ is a $(C_{1-5})$alkoxy, Compound E can be treated with a base (e.g., 1N NaOH) at reflux for 10 hours or more, in any of a variety of solvents (e.g., MeOH). The solution is then optionally cooled, made acidic (e.g., using 1N HCl), and extracted (e.g., using $CHCl_3$). The organic layer is then dried (e.g., $MgSO_4$) and concentrated in vacuo to provide Compound F. Compound F can be optionally purified using any of a variety of purification techniques known in the art, including silica gel chromatography.

Additionally, Compound F can be reacted with Compound G in the presence of O-(7-Azabenzotriazole-1-yl)-N,N,N'N'-tetramethyluronium hexafluorophosphate (HATU) and triethylamine at room temperature in any of a variety of solvents (e.g., $CH_2Cl_2$). The resulting mixture is then washed with an acid (e.g., 0.1N HCl) and brine, dried (e.g., $MgSO_4$), and concentrated in vacuo to provide Compound H. In addition, Compound H is optionally purified using any of a variety of purification techniques known in the art, including silica gel chromatography.

Compounds of the present invention can also be prepared using the synthetic route shown in Scheme 2. Compound I is reacted with Compound J in the presence of a base (e.g., NaH, lithium diisopropyl amide (LDA), BuLi or the like) at temperatures from −78° C. to 100° C. The resulting mixture is then optionally diluted with a solvent (e.g., EtOAc), washed with an acid (e.g., 1N HCl) and brine, dried (e.g., $MgSO_4$), and concentrated in vacuo to provide Compound K. In addition, Compound K is optionally purified using any of a variety of purification techniques known in the art, including silica gel chromatography.

Chiral components can be separated and purified using any of a variety of techniques known to those skilled in the art. For example, chiral components can be purified using supercritical fluid chromatography (SFC). In one particular variation, chiral analytical SFC/MS analyses are conducted using a Berger analytical SFC system (AutoChem, Newark, Del.) which consists of a Berger SFC dual pump fluid control module with a Berger FCM 1100/1200 supercritical fluid pump and FCM 1200 modifier fluid pump, a Berger TCM 2000 oven, and an Alcott 718 autosampler. The integrated system can be controlled by BI-SFC Chemstation software version 3.4. Detection can be accomplished with a Waters ZQ 2000 detector operated in positive mode with an ESI interface and a scan range from 200-800 Da with 0.5 second per scan. Chromatographic separations can be performed on a ChiralPak AD-H, ChiralPak AS-H, ChiralCel OD-H, or ChiralCel OJ-H column (5μ, 4.6×250 mm; Chiral Technologies, Inc. West Chester, Pa.) with 10 to 40% methanol as the modifier and with or without ammonium acetate (10 mM). Any of a variety of flow rates can be utilized including, for example, 1.5 or 3.5 mL/min with an inlet pressure set at 100 bar. Additionally, a variety of sample injection conditions can be used including, for example, sample injections of either 5 or 10 μL in methanol at 0.1 mg/mL in concentration.

In another variation, preparative chiral separations are performed using a Berger MultiGram II SFC purification system. For example, samples can be loaded onto a ChiralPak AD column (21×250 mm, 10μ). In particular variations, the flow rate for separation can be 70 mL/min, the injection volume up to 2 mL, and the inlet pressure set at 130 bar. Stacked injections can be applied to increase the efficiency.

In each of the above reaction procedures or schemes, the various substituents may be selected from among the various substituents otherwise taught herein.

Descriptions of the syntheses of particular compounds according to the present invention based on the above reaction scheme are set forth herein.

Examples of MEK Inhibitors

The present invention is further exemplified, but not limited by, the following examples that describe the synthesis of particular compounds according to the invention.

Example 1a

Ethyl 3-(2-fluoro-4-iodophenylamino)-3-iminopropanoate

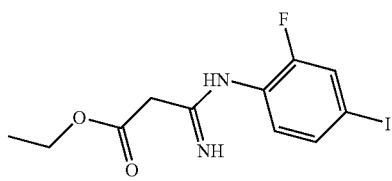

2-Fluoro-4-iodo-aniline (3.5 g, 14.7 mmol) was added to a suspension of ethyl 3-imino-3-phenoxypropionate, hydrochloride (see, Danswan et al, *J. Heterocyclic Chem.*, 26, 1989, 293-299; 3.42 g, 14.0 mmol) in EtOAc (20 mL). The reaction was stirred at reflux for 2 h and then concentrated in vacuo. The residue was taken up in ether, and the precipitate was collected by filtration to give 3.24 g (60%) of the hydrochloride salt of the title compound as a light blue solid. $^1$H NMR (400 MHz, DMSO-$d_6$): δ 10.04 (s, 1H), 9.12 (s, 1H), 7.92 (dd, 1H, J=9.6, 2.0 Hz), 7.72 (dd, 1H, J=8.4, 1.2 Hz), 7.13 (t, 1H, J=8.4 Hz), 4.18 (q, 2H, J=6.8 Hz), 3.92 (s, 2H), 1.23 (t, 3H). MS (ES) [m+H] calc'd for $C_{11}H_{12}FIN_2O_2$, 351; found 351.

Example 1b

Ethyl 5-acetyl-2-(2-fluoro-4-iodophenylamino)-1H-pyrrole-3-carboxylate

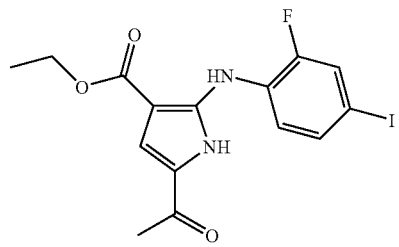

Example 1a (840 mg, 2.4 mmol) and 1-bromo-2,3-butanedione (see, Matulennko et al., *Bioorg. Med. Chem.*, 13, 2005, 3705-3720; 436 mg, 2.64 mmol) were stirred in THF at room temperature for 6 h, and then heated at reflux for 2 h. The solution was concentrated in vacuo, and the residue was dissolved in $CH_2Cl_2$. Organics were washed with 0.1N HCl and brine, dried ($MgSO_4$), and concentrated. Purification by silica gel chromatography gave 320 mg (32%) of the title compound as a brown solid. MS (ES) [m+H] calc'd for $C_{15}H_{14}FIN_2O_3$, 417; found 417.

Example 1

5-Acetyl-2-(2-fluoro-4-iodo-phenylamino)-1H-pyrrole-3-carboxylic acid

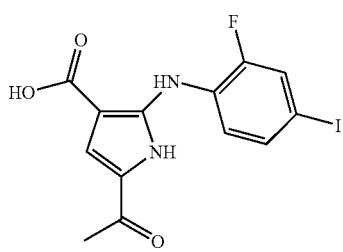

Example 1b (80 mg, 0.19 mmol) was stirred in MeOH (10 mL) with 1N NaOH (5 mL) at reflux for 16 h. The cooled solution was made acidic with 1N HCl and extracted (3×) with $CHCl_3$. Organics were dried ($MgSO_4$) and concentrated in vacuo. Purification by silica gel chromatography gave 32 mg (43%) of the title compound as an off-white solid. $^1$H NMR (400 MHz, MeOD-$d_4$): δ 7.59 (dd, 1H, J=9.2, 2.0 Hz), 7.54 (dd, 1H, J=8.2, 1.2 Hz), 7.38 (s, 1H), 7.29 (t, 1H, J=8.4 Hz), 2.38 (s, 3H). MS (ES) [m+H] calc'd for $C_{13}H_{10}FIN_2O_3$, 389; found 389.

Example 2

5-Acetyl-2-(2-fluoro-4-iodophenylamino)-N-(2-hydroxyethoxy)-1H-pyrrole-3-carboxamide

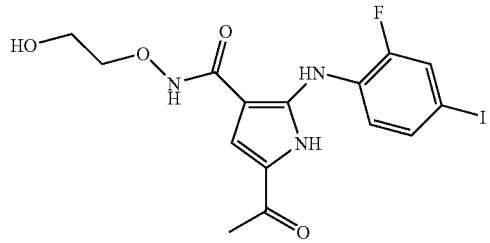

Example 1 (18 mg, 0.046 mmol), O-(2-tert-butoxy-ethyl)-hydroxylamine (see, WO05/110410; 19 mg, 0.14 mmol), HATU (35 mg, 0.092 mmol), and triethylamine (20 μL, 0.14 mmol) were stirred in $CH_2Cl_2$ (5 mL) at room temperature for 2 h. The solution was washed with 0.1N HCl and brine, dried ($MgSO_4$), and concentrated in vacuo. The residue was stirred in TFA (4 mL) for 2 h and then concentrated. Purification by silica gel chromatography gave 5.7 mg (28%) of the title compound as a tan solid. $^1$H NMR (400 MHz, MeOD-$d_4$): δ 7.90 (s, 1H), 7.55 (dd, 1H, J=9.6, 2.0 Hz), 7.50 (dd, 1H, J=8.4, 1.2 Hz), 7.32 (br s, 1H), 7.24 (t, 1H, J=8.4 Hz), 3.99 (t, 2H, J=4.8 Hz), 3.75 (t, 2H, J=4.8 Hz), 2.35 (s, 3H). MS (ES) [m+H] calc'd for $C_{15}H_{15}FIN_3O_4$, 448; found 448.

Example 3a

Ethyl 5-acetyl-2-(2-fluoro-4-iodophenylamino)-1-methyl-1H-pyrrole-3-carboxylate

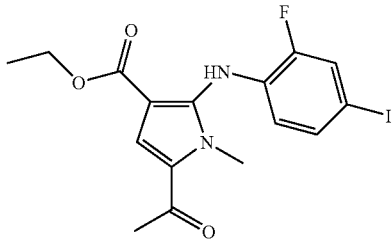

Example 1b (90 mg, 0.22 mmol) and dimethylsulfate (25 μL, 0.26 mmol) were stirred in THF at 0° C. NaH (60%, 17 mg, 0.43 mmol) was added, and the reaction stirred for 4 h while warming to room temperature. The solution was diluted with EtOAc, washed with 1N HCl and brine, dried ($MgSO_4$), and concentrated in vacuo. Purification by silica gel chromatography (1:1:1 EtOAc/hexanes/$CH_2Cl_2$) gave 82 mg (88%) of the title compound as a tan oil. $^1$H NMR (400 MHz, MeOD-$d_4$): δ 7.52 (s, 1H), 7.47 (dd, 1H, J=10.4, 2.0 Hz), 7.31 (dd, 1H, J=8.8, 1.2 Hz), 6.30 (t, 1H, J=8.8 Hz), 4.15 (q, 2H, =6.8 Hz), 3.69 (s, 3H), 2.45 (s, 3H), 1.21 (t, 3H, J=6.8 Hz). MS (ES) [m+H] calc'd for $C_{16}H_{16}FIN_2O_3$, 431; found 431.

Example 3

5-Acetyl-2-(2-fluoro-4-iodophenylamino)-1-methyl-1H-pyrrole-3-carboxylic acid

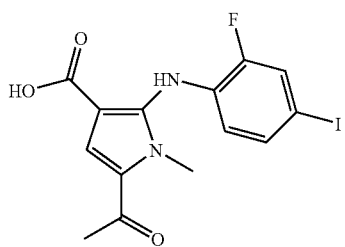

The title compound was prepared in 55% yield from Example 3a according to the general procedure outlined for Example 1. $^1$H NMR (400 MHz, MeOD-$d_4$): δ 7.51 (s, 1H), 7.46 (dd, 1H, J=10.8, 2.0 Hz), 7.33 (dd, 1H, J=8.4, 1.2 Hz), 6.33 (t, 1H, J=8.4 Hz), 3.63 (s, 3H), 2.44 (s, 3H). MS (ES) [m+H] calc'd for $C_{14}H_{12}FIN_2O_3$, 403; found 403.

Example 4

5-Acetyl-2-(2-fluoro-4-iodophenylamino)-N-(2-hydroxyethoxy)-1-methyl-1H-pyrrole-3-carboxamide

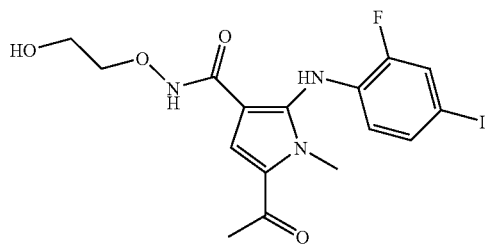

Example 3 (28 mg, 0.069 mmol), O-(2-tert-butoxy-ethyl)-hydroxylamine (see, WO05/110410; 28 mg, 0.21 mmol), HATU (40 mg, 0.10 mmol), and triethylamine (29 μL, 0.21 mmol) were stirred in $CH_2Cl_2$ (3 mL) at room temperature for 2 h. The solution was washed with 0.1N HCl and brine, dried ($MgSO_4$), and concentrated in vacuo. The residue was stirred in TFA (4 mL) for 2 h and then concentrated. Purification by silica gel chromatography gave 8.8 mg (28%) of the title compound as a white solid. $^1$H NMR (400 MHz, MeOD-$d_4$): δ 7.47 (dd, 1H, J=10.8, 2.0 Hz), 7.44 (br s, 1H), 7.33 (dd, 1H, J=8.4, 1.2 Hz), 6.32 (t, 1H, J=8.4 Hz), 3.90 (t, 2H, J=4.8 Hz), 3.66 (t, 2H, J=4.8 Hz), 3.64 (s, 3H), 2.44 (s, 3H). MS (ES) [m+H] calc'd for $C_{16}H_{17}FIN_3O_4$, 461; found 461.

Example 5a 2-(3-tert-butoxypropoxy)isoindoline-1,3-dione

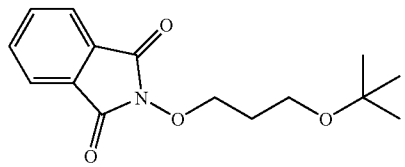

Diisopropyl azodicarboxylate (13.4 mL, 68 mmol) was added dropwise at 0° C. to a stirred suspension of 3-tert-butoxy-propan-1-ol (9.0 g, 68 mmol), triphenylphosphine (17.8 g, 68 mmol), and N-hydroxyphthalimide (11.1 g, 68 mmol) in THF (150 mL), and the reaction stirred for 16 h at room temperature. The solution was concentrated in vacuo and purified by silica gel chromatography (20% Et$_2$O/hexanes) to give 15.5 g (82%) of the title compound as a faintly yellow solid. $^1$H NMR (400 MHz, CDCl$_3$): δ 7.72-7.84 (m, 4H), 4.30 (t, 2H, J=4.8 Hz), 3.58 (t, 2H, J=4.8 Hz), 1.94-2.00 (m, 2H), 1.20 (s, 9H). MS (ES) [m+H] calc'd for C$_{15}$H$_{19}$NO$_4$, 278; found 278.

Example 5b 2-(3-tert-Butoxypropoxy)isoindoline-1,3-dione

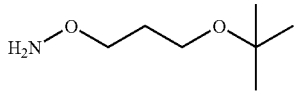

Hydrazine hydrate (1.36 mL, 43.3 mmol) was added to a solution of Example 5a (6.0 g, 21.7 mmol) in CH$_2$Cl$_2$ (50 mL) with MeOH (5 mL), and the reaction stirred 1 h at room temperature. The precipitate was removed by filtration, and the filtrate was purified by silica gel chromatography (6% MeOH/CH$_2$Cl$_2$) to give 2.4 g (75%) of the title compound as a clear oil. $^1$H NMR (400 MHz, CDCl$_3$): δ 4.94 (br s, 2H), 3.71 (t, 2H, J=6.4 Hz), 3.38 (t, 2H, J=6.4 Hz), 1.70-1.79 (m, 2H), 1.15 (s, 9H).

Example 5

5-Acetyl-2-(2-fluoro-4-iodophenylamino)-N-(3-hydroxypropoxy)-1-methyl-1H-pyrrole-3-carboxamide

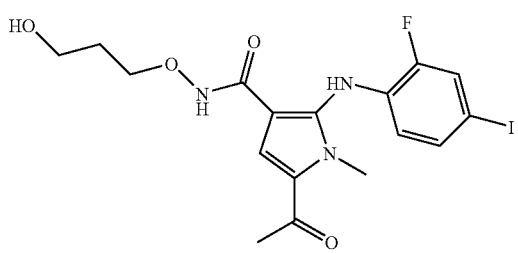

The title compound was prepared in 51% yield from Example 3 and Example 5b according to the general procedure outlined for Example 2. $^1$H NMR (400 MHz, MeOD-d$_4$): δ 7.46 (dd, 1H, J=10.8, 2.0 Hz), 7.43 (s, 1H), 7.33 (dd, 1H, J=8.4, 1.2 Hz), 6.32 (t, 1H, J=8.4 Hz), 3.93 (t, 2H, J=6.0 Hz), 3.66 (t, 2H, J=6.0 Hz), 3.64 (s, 3H), 2.43 (s, 3H), 1.79-1.83 (m, 2H). MS (ES) [m+H] calc'd for C$_{17}$H$_{19}$FIN$_3$O$_4$, 476; found 476.

Example 6

(R)-5-Acetyl-N-(2,3-dihydroxypropoxy)-2-(2-fluoro-4-iodophenylamino)-1-methyl-1H-pyrrole-3-carboxamide

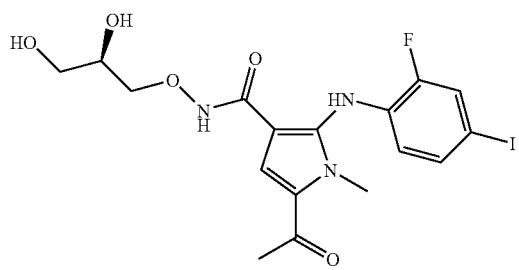

Example 3 (80 mg, 0.2 mmol), (R)-(2,2-dimethyl-1,3-dioxolan-4-yl)methoxyamine (see Bailey et al., *J. Med. Chem.*, 34, 1991, 51-65; 88 mg, 0.6 mmol), and HOBt (30 mg, 0.22 mmol) were stirred in CH$_2$Cl$_2$ (5 mL) at room temperature. EDC (58 mg, 0.3 mmol) and then triethylamine (84 μL, 0.6 mmol) were added, and the reaction stirred for 2 h. The solution was washed with 0.1N HCl and brine, dried (MgSO$_4$), and concentrated in vacuo. The residue was stirred in MeOH (2.5 mL) and H$_2$O (300 μL) with p-toluenesulfonic acid (19 mg, 0.1 mmol) for 16 h. Triethylamine (25 μL) was added, and the solution was concentrated in vacuo. Purification by silica gel chromatography gave 48 mg (49%) of the title compound as a white solid. $^1$H NMR (400 MHz, MeOD-d$_4$): δ 7.47 (dd, 1H, J=10.8, 2.0 Hz), 7.45 (s, 1H), 7.33 (dd, 1H, J=8.4, 1.2 Hz), 6.32 (t, 1H, J=8.4 Hz), 3.86-3.94 (m, 1H), 3.72-3.83 (m, 2H), 3.64 (s, 3H), 3.52-3.59 (m, 2H), 2.43 (s, 3H). MS (ES) [m+H] calc'd for C$_{17}$H$_{19}$FIN$_3$O$_5$, 492; found 492.

Example 7

(S)-5-Acetyl-N-(2,3-dihydroxypropoxy)-2-(2-fluoro-4-iodophenylamino)-1-methyl-1H-pyrrole-3-carboxamide

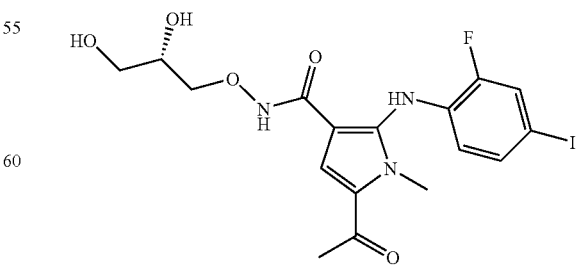

Example 3 (20 mg, 0.05 mmol), (S)-(2,2-dimethyl-1,3-dioxolan-4-yl)methoxyamine (see Bailey et al., *J. Med.*

Chem., 34, 1991, 51-65; 22 mg, 0.15 mmol), and HOBt (7.5 mg, 0.055 mmol) were stirred in CH$_2$Cl$_2$ (3 mL) at room temperature. EDC (14 mg, 0.075 mmol) and then triethylamine (21 µL, 0.15 mmol) were added, and the reaction stirred for 2 h. The solution was washed with 0.1N HCl and brine, dried (MgSO$_4$), and concentrated in vacuo. The residue was stirred in MeOH (2.5 mL) and H$_2$O (300 µL) with p-toluenesulfonic acid (5.0 mg, 0.026 mmol) for 16 h. Triethylamine (25 µL) was added, and the solution was concentrated in vacuo. Purification by silica gel chromatography gave 16 mg (65%) of the title compound as a white solid. $^1$H NMR (400 MHz, MeOD-d$_4$): δ 7.47 (dd, 1H, J=10.8, 2.0 Hz), 7.45 (s, 1H), 7.33 (dd, 1H, J=8.4, 1.2 Hz), 6.32 (t, 1H, J=8.4 Hz), 3.86-3.94 (m, 1H), 3.72-3.83 (m, 2H), 3.64 (s, 3H), 3.52-3.59 (m, 2H), 2.43 (s, 3H). MS (ES) [m+H] calc'd for C$_{17}$H$_{19}$FIN$_3$O$_5$, 492; found 492.

Example 8

5-Acetyl-2-(2-fluoro-4-iodophenylamino)-N-(3-hydroxy-2-(hydroxymethyl)propoxy)-1-methyl-1H-pyrrole-3-carboxamide

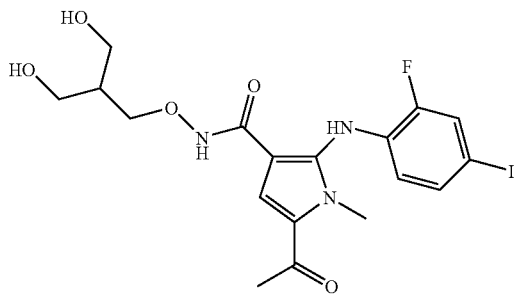

The title compound was prepared in 67% yield from Example 3 and (2,2-dimethyl-1,3-dioxan-5-yl)methoxyamine (see Harnden et al, *J. Med. Chem.*, 33, 1990, 187-196) according to the general procedure outlined for Example 6. $^1$H NMR (400 MHz, MeOD-d$_4$): δ 7.47 (dd, 1H, J=10.8, 2.0 Hz), 7.44 (br s, 1H), 7.33 (dd, 1H, J=8.4, 1.2 Hz), 6.32 (t, 1H, J=8.4 Hz), 3.81 (d, 2H, J=6.0 Hz), 3.48-3.57 (m, 7H), 2.43 (s, 3H), 1.85-1.95 (m, 1H). MS (ES) [m+H] calc'd for C$_{18}$H$_{21}$FIN$_3$O$_5$, 506; found 506.

Example 9a

Ethyl 5-acetyl-4-chloro-2-(2-fluoro-4-iodophenylamino)-1H-pyrrole-3-carboxylate

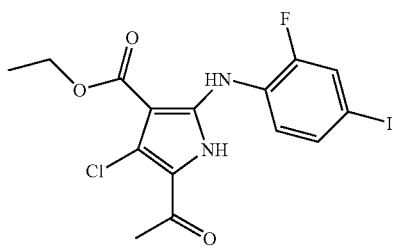

Example 1b (700 mg, 1.68 mmol) was stirred in CH$_2$Cl$_2$ until completely dissolved, and then was cooled to 0° C. A solution of N-chlorosuccinimide (240 mg, 1.77 mmol) in CH$_2$Cl$_2$ was added, and the reaction stirred 18 h at r.t. The solution was concentrated and purified by silica gel chromatography (100% CH$_2$Cl$_2$) to give 402 mg (53%) of the title compound as a pale yellow solid. $^1$H NMR (400 MHz, CDCl$_3$): δ 9.10 (s, 1H), 8.82 (s, 1H), 7.45-7.56 (m, 2H), 7.08 (t, 1H, J=8.4 Hz), 4.37 (q, 2H, J=6.8 Hz), 2.52 (s, 3H), 1.37 (t, 3H). MS (ES) [m+H] calc'd for C$_{15}$H$_{14}$ClFIN$_2$O$_3$, 451, 453; found 451, 453.

Example 9b

Ethyl 5-acetyl-4-chloro-2-(2-fluoro-4-iodophenylamino)-1-methyl-1H-pyrrole-3-carboxylate

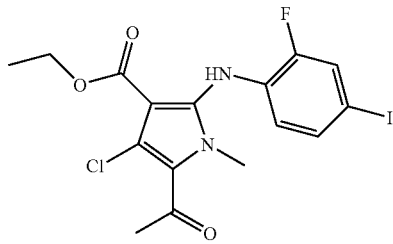

Example 9a (402 mg, 0.89 mmol), cesium carbonate (180 mg, 1.43 mmol), and dimethylsulfate (135 µL, 1.43 mmol) were stirred in DMF (6 mL) at 48° C. for 18 h. The solution was diluted with H$_2$O and extracted (3×) with Et$_2$O. Organics were dried (MgSO$_4$) and concentrated in vacuo. Purification by silica gel chromatography (1:1:1 EtOAc/hexanes/CH$_2$Cl$_2$) gave 222 mg (54%) of the title compound as a tan oil. MS (ES) [m+H] calc'd for C$_{16}$H$_{15}$ClFIN$_2$O$_3$, 465, 467; found 465, 467.

Example 9

5-Acetyl-4-chloro-2-(2-fluoro-4-iodophenylamino)-1-methyl-1H-pyrrole-3-carboxylic acid

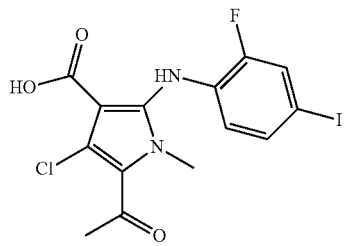

Example 9b (222 mg, 0.48 mmol) was stirred in MeOH (10 mL) with 1N NaOH (5 mL) at reflux for 3 h. The cooled solution was made acidic with 1N HCl and extracted (3×) with CHCl$_3$. Organics were dried (MgSO$_4$) and concentrated in vacuo. Purification by silica gel chromatography (5% MeOH/CH$_2$Cl$_2$) gave 140 mg (67%) of the title compound as an off-white solid. $^1$H NMR (400 MHz, MeOD-d$_4$): δ 7.50 (dd, 1H, J=9.2, 2.0 Hz), 7.36 (dd, 1H, J=8.2, 1.2 Hz), 6.37 (t, 1H, J=8.4 Hz), 3.55 (s, 3H), 2.62 (s, 3H). MS (ES) [m+H] calc'd for C₁₄H₁₁ClFIN₂O₃, 437, 439; found 437, 439.

Example 10

(R)-5-Acetyl-4-chloro-N-(2,3-dihydroxypropoxy)-2-(2-fluoro-4-iodophenylamino)-1-methyl-1H-pyrrole-3-carboxamide

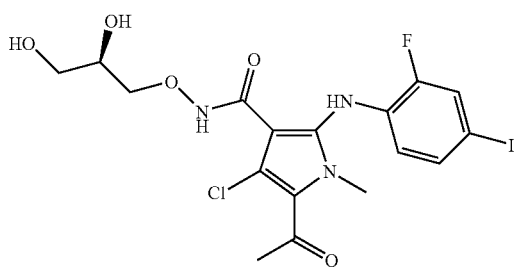

The title compound was prepared in 56% yield from example 9 and (R)—O-((2,2-dimethyl-1,3-dioxolan-4-yl)methyl)hydroxylamine according to the general procedure outlined for example 6. ¹H NMR (400 MHz, MeOD-d₄): δ 7.45 (dd, 1H, J=10.8, 2.0 Hz), 7.32 (dd, 1H, J=8.4, 1.2 Hz), 6.38 (t, 1H, J=8.4 Hz), 3.70-3.86 (m, 3H), 3.62 (s, 3H), 3.50-3.58 (m, 2H), 2.60 (s, 3H). MS (ES) [m+H] calc'd for C₁₇H₁₈ClFIN₃O₅, 526, 528; found 526, 528.

Example 11

(S)-5-Acetyl-4-chloro-N-(2,3-dihydroxypropoxy)-2-(2-fluoro-4-iodophenylamino)-1-methyl-1H-pyrrole-3-carboxamide

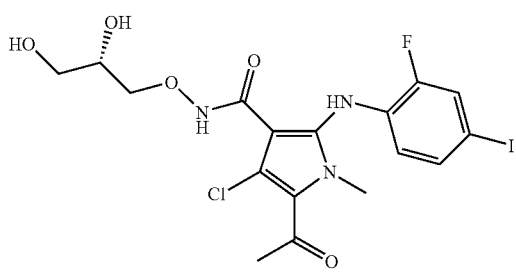

The title compound was prepared in 31% yield from example 9 and (S)—O-((2,2-dimethyl-1,3-dioxolan-4-yl)methyl)hydroxylamine according to the general procedure outlined for example 6. ¹H NMR (400 MHz, MeOD-d₄): δ 7.45 (dd, 1H, J=10.8, 2.0 Hz), 7.32 (dd, 1H, J=8.4, 1.2 Hz), 6.38 (t, 1H, J=8.4 Hz), 3.70-3.86 (m, 3H), 3.62 (s, 3H), 3.50-3.58 (m, 2H), 2.60 (s, 3H). MS (ES) [m+H] calc'd for C₁₇H₁₈ClFIN₃O₅, 526, 528; found 526, 528.

Example 12

5-Acetyl-4-chloro-2-(2-fluoro-4-iodophenylamino)-N-(2-hydroxyethoxy)-1-methyl-1H-pyrrole-3-carboxamide

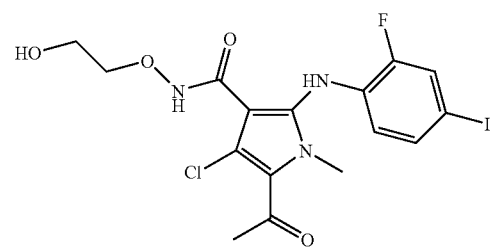

The title compound was prepared in 35% yield from example 9 and O-(2-tert-butoxy-ethyl)-hydroxylamine (see, WO05/110410) according to the general procedure outlined for example 2. ¹H NMR (400 MHz, MeOD-d₄): δ 7.45 (dd, 1H, J=10.8, 2.0 Hz), 7.31 (dd, 1H, J=8.4, 2.0 Hz), 6.39 (t, 1H, J=8.4 Hz), 3.78 (t, 2H, J=4.8 Hz), 3.66 (s, 3H), 3.60 (t, 2H, J=4.8 Hz), 2.61 (s, 3H). MS (ES) [m+H] calc'd for C₁₆H₁₆ClFIN₃O₅, 496, 498; found 496, 498.

Example 13

5-Acetyl-2-(2-fluoro-4-iodophenylamino)-1-methyl-1H-pyrrole-3-carboxamide

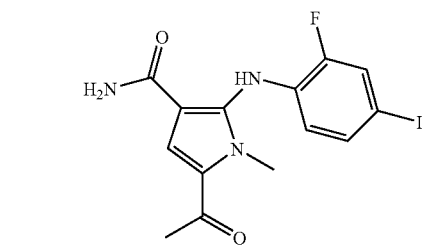

The title compound was prepared in 80% yield from example 3 and 2,4-dimethoxybenzylamine in a manner similar to the general procedure outlined for example 2. ¹H NMR (400 MHz, MeOD-d₄): δ 7.55 (s, 1H), 7.43 (dd, 1H, J=10.8, 2.0 Hz), 7.30 (dd, 1H, J=8.4, 1.2 Hz), 6.29 (t, 1H, J=8.4 Hz), 3.57 (s, 3H), 2.40 (s, 3H). MS (ES) [m+H] calc'd for C₁₄H₁₃FIN₃O₂, 402; found 402.

Example 14

5-Acetyl-N-(1,3-dihydroxypropan-2-yloxy)-2-(2-fluoro-4-iodophenylamino)-1-methyl-1H-pyrrole-3-carboxamide

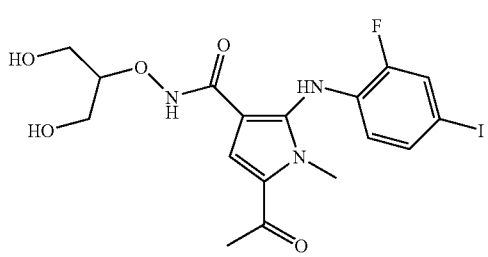

The title compound was prepared in 57% yield from example 3 and 2-phenyl-1,3-dioxan-5-ol (see, EP1666485) in a manner similar to the general procedure outlined for example 6. $^1$H NMR (400 MHz, MeOD-d$_4$): δ 7.42-7.50 (m, 2H), 7.33 (dd, 1H, J=10.0, 1.2 Hz), 6.32 (t, 1H, J=8.8 Hz), 3.76-3.84 (m, 1H), 3.58-3.66 (m, 7H), 2.44 (s, 3H). MS (ES) [m+H] calc'd for C$_{17}$H$_{19}$FIN$_3$O$_5$, 492; found 492.

Example 15

5-Acetyl-N-(2,3-dihydroxypropyl)-2-(2-fluoro-4-iodophenylamino)-1-methyl-1H-pyrrole-3-carboxamide

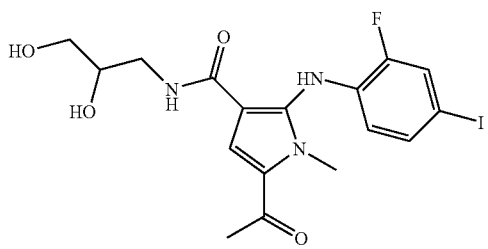

The title compound was prepared in 84% yield from example 3 and (2,2-dimethyl-1,3-dioxolan-4-yl)methylamine in a manner similar to the general procedure outlined for example 6. $^1$H NMR (400 MHz, MeOD-d$_4$): δ 7.58 (s, 1H), 7.47 (dd, 1H, J=10.8, 2.0 Hz), 7.33 (d, 1H, J=8.4 Hz), 6.29 (t, 1H, J=8.4 Hz), 3.63-3.72 (m, 1H), 3.62 (s, 3H), 3.41-3.48 (m, 3H), 3.22-3.30 (m, 1H), 2.44 (s, 3H). MS (ES) [m+H] calc'd for C$_{17}$H$_{19}$FIN$_3$O$_4$, 476; found 476.

Example 16

5-Acetyl-2-(2-fluoro-4-iodophenylamino)-N-(3-hydroxypropyl)-1-methyl-1H-pyrrole-3-carboxamide Example 3 (20 mg, 0.05 mmol), hydroxypropylamine (12 μL, 0.15 mmol), and HOBt (7.5 mg, 0.05 mmol) were stirred in CH$_2$Cl$_2$ (1 mL) at room temperature. EDC (14 mg, 0.075 mmol) and then triethylamine (21 μL, 0.15 mol) were added, and the reaction stirred for 2 h. The solution was washed with 0.1N HCl and brine, dried (MgSO$_4$), and concentrated in vacuo. Purification by silica gel chromatography gave 12 mg (52%) of the title compound as a white solid. $^1$H NMR (400 MHz, MeOD-d$_4$): δ 7.55 (s, 1H), 7.47 (dd, 1H, J=10.8, 2.0 Hz), 7.33 (d, 1H, J=8.4 Hz), 6.30 (t, 1H, J=8.4 Hz), 3.62 (s, 3H), 3.51-3.59 (m, 2H), 3.30-3.38 (m, 2H), 2.44 (s, 3H). MS (ES) [m+H] calc'd for C$_{17}$H$_{19}$FIN$_3$O$_3$, 460; found 460.

Example 17

5-Acetyl-2-(2-fluoro-4-iodophenylamino)-N-methoxy-N,1-dimethyl-1H-pyrrole-3-carboxamide The title compound was prepared in 88% yield from Example 3 and N,O-dimethylhydroxylamine in a manner similar to the general procedure outlined for Example 16. $^1$H NMR (400 MHz, MeOD-d$_4$): δ 7.53 (s, 1H), 7.45 (dd, 1H, J=10.4, 2.0 Hz), 7.33 (d, 1H, J=8.4 Hz), 6.38 (t, 1H, J=8.4 Hz), 3.65 (s, 3H), 3.64 (s, 3H), 3.32 (s, 3H), 2.43 (s, 3H). MS (ES) [m+H] calc'd for C$_{16}$H$_{17}$FIN$_3$O$_3$, 446; found 446.

Example 18

1-(5-(2-Fluoro-4-iodophenylamino)-4-(4-hydroxy-isoxazolidine-2-carbonyl)-1-methyl-1H-pyrrol-2-yl)ethanone

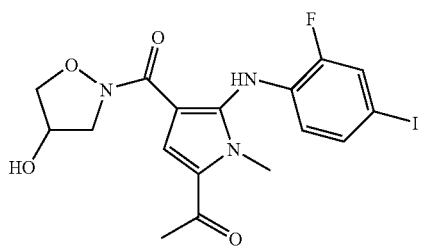

The title compound was prepared in 72% yield from example 3 and isoxazolidin-4-ol in a manner similar to the general procedure outlined for Example 16. $^1$H NMR (400 MHz, CDCl$_3$): δ 8.21 (s, 1H), 7.60 (s, 1H), 7.40 (dd, 1H, J=10.4, 2.0 Hz), 7.28 (d, 1H, J=8.4 Hz), 6.33 (t, 1H, J=8.4 Hz), 4.77-4.85 (br s, 1H), 4.05-4.13 (m, 2H), 3.93-3.99 (m, 1H), 3.75-3.81 (m, 1H), 3.57 (s, 3H), 2.44 (s, 3H). MS (ES) [m+H] calc'd for C$_{17}$H$_{17}$FIN$_3$O$_4$, 474; found 474.

Example 19

(R)-5-Acetyl-N-(2,4-dihydroxybutoxy)-2-(2-fluoro-4-iodophenylamino)-1-methyl-1H-pyrrole-3-carboxamide

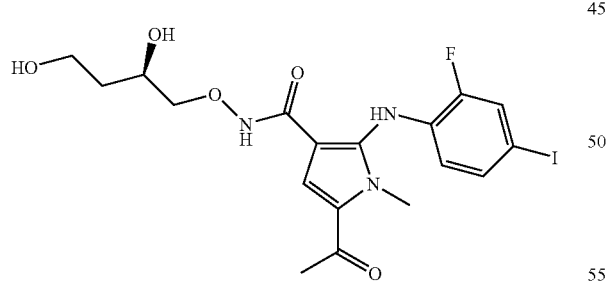

The title compound was prepared in 34% yield from Example 3 and O-(((4R)-2-phenyl-1,3-dioxan-4-yl)methyl)hydroxylamine in a manner similar to the general procedure outlined for Example 6. $^1$H NMR (400 MHz, MeOD-d$_4$): δ 7.40-7.49 (m, 2H), 7.33 (d, 1H, J=8.4 Hz), 6.33 (t, 1H, J=8.4 Hz), 3.80-3.96 (m, 2H), 3.64-3.74 (m, 3H), 3.64 (s, 3H), 2.43 (s, 3H), 1.54-1.68 (m, 2H). MS (ES) [m+H] calc'd for C$_{18}$H$_{21}$FIN$_3$O$_5$, 506; found 506.

Example 20

(S)-5-Acetyl-N-(2,4-dihydroxybutoxy)-2-(2-fluoro-4-iodophenylamino)-1-methyl-1H-pyrrole-3-carboxamide

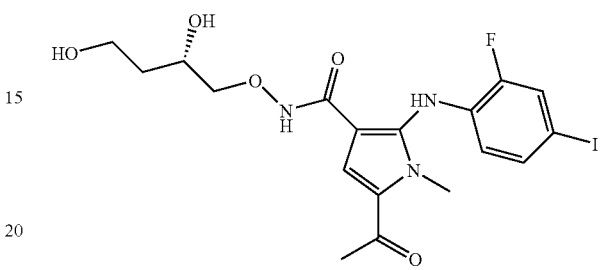

The title compound was prepared in 35% yield from example 3 and O-(((4S)-2-phenyl-1,3-dioxan-4-yl)methyl)hydroxylamine in a manner similar to the general procedure outlined for Example 6. $^1$H NMR (400 MHz, MeOD-d$_4$): δ 7.40-7.49 (m, 2H), 7.33 (d, 1H, J=8.4 Hz), 6.33 (t, 1H, J=8.4 Hz), 3.80-3.96 (m, 2H), 3.64-3.74 (m, 3H), 3.64 (s, 3H), 2.43 (s, 3H), 1.54-1.68 (m, 2H). MS (ES) [m+H] calc'd for C$_{18}$H$_{21}$FIN$_3$O$_5$, 506; found 506.

Example 21

1-(4-(Azetidine-1-carbonyl)-5-(2-fluoro-4-iodophenylamino)-1-methyl-1H-pyrrol-2-yl)ethanone

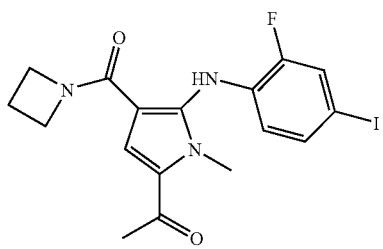

The title compound was prepared in 54% yield from Example 3 and azetidine in a manner similar to the general procedure outlined for Example 16. $^1$H NMR (400 MHz, CDCl$_3$): δ 7.42 (dd, 1H, J=10.0, 2.0 Hz), 7.30 (d, 1H, J=8.4 Hz), 7.02 (s, 1H), 6.35 (t, 1H, J=8.4 Hz), 4.22-4.50 (m, 4H), 3.58 (s, 3H), 2.42 (s, 3H), 2.36-2.42 (m, 2H). MS (ES) [m+H] calc'd for C$_{17}$H$_{17}$FIN$_3$O$_2$, 442; found 442.

Example 22

1-(4-(3-Aminoazetidine-1-carbonyl)-5-(2-fluoro-4-iodophenylamino)-1-methyl-1H-pyrrol-2-yl)ethanone

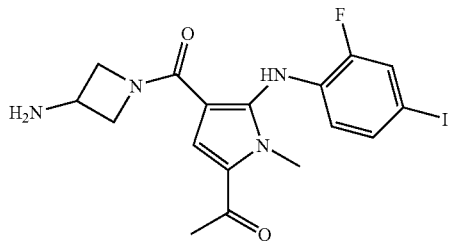

The title compound was prepared in 82% yield from Example 3 and tert-butyl 3-aminoazetidine-1-carboxylate in a manner similar to the general procedure outlined for Example 16, followed by TFA deprotection and HPLC purification. $^1$H NMR (400 MHz, CDCl$_3$): δ 8.46 (s, 1H), 7.40 (dd, 1H, J=10.0, 2.0 Hz), 7.28 (d, 1H, J=8.4 Hz), 6.99 (s, 1H), 6.34 (t, 1H, J=8.4 Hz), 4.30-4.70 (m, 2H), 3.68-4.12 (m, 3H), 3.57 (s, 3H), 2.41 (s, 3H). MS (ES) [m+H] calc'd for C$_{17}$H$_{18}$FIN$_4$O$_2$, 457; found 457.

Example 23

(S)-1-(5-(2-Fluoro-4-iodophenylamino)-4-(3-(hydroxymethyl)pyrrolidine-1-carbonyl)-1-methyl-1H-pyrrol-2-yl)ethanone

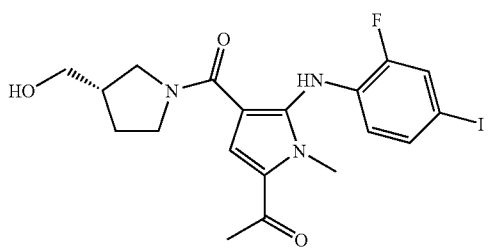

The title compound was prepared in 70% yield from Example 3 and (S)-pyrrolidin-3-ylmethanol in a manner similar to the general procedure outlined for Example 16. $^1$H NMR (400 MHz, CDCl$_3$): δ 7.39 (dd, 1H, J=10.0, 2.0 Hz), 8.30 (s, 1H), 7.28 (d, 1H, J=8.4 Hz), 7.18 (s, 1H), 6.35 (t, 1H, J=8.4 Hz), 4.78 (br s, 1H), 4.26-4.35 (m, 1H), 3.62-3.90 (m, 5H), 3.60 (s, 3H), 2.43 (s, 3H), 1.80-2.18 (m, 3H). MS (ES) [m+H] calc'd for C$_{19}$H$_{21}$FIN$_3$O$_3$, 486; found 486.

Example 24

1-(5-(2-Fluoro-4-iodophenylamino)-4-(2-(hydroxymethyl)azetidine-1-carbonyl)-1-methyl-1H-pyrrol-2-yl)ethanone

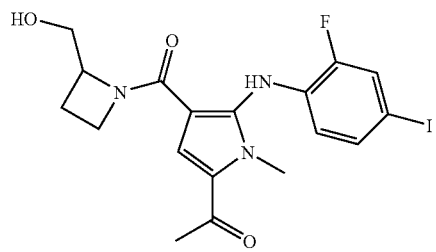

The title compound was prepared in 53% yield from Example 3 and azetidin-2-ylmethanol in a manner similar to the general procedure outlined for Example 16. $^1$H NMR (400 MHz, CDCl$_3$): δ 7.42 (dd, 1H, J=10.0, 2.0 Hz), 7.29 (d, 1H, J=8.4 Hz), 7.04 (s, 1H), 6.37 (t, 1H, J=8.4 Hz), 4.73-4.80 (m, 1H), 4.34-4.48 (m, 2H), 3.68-3.85 (m, 2H), 3.56 (s, 3H), 2.42 (s, 3H), 2.36-2.42 (m, 1H), 2.03-2.10 (m, 1H). MS (ES) [m+H] calc'd for C$_{18}$H$_{19}$FIN$_3$O$_3$, 472; found 472.

Example 25

(R)-1-(5-(2-Fluoro-4-iodophenylamino)-4-(3-(hydroxymethyl)pyrrolidine-1-carbonyl)-1-methyl-1H-pyrrol-2-yl)ethanone

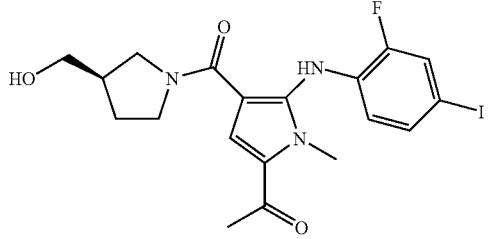

The title compound was prepared in 60% yield from Example 3 and (R)-pyrrolidin-3-ylmethanol in a manner similar to the general procedure outlined for Example 16. $^1$H NMR (400 MHz, CDCl$_3$): δ 7.39 (dd, 1H, J=10.0, 2.0 Hz), 7.28 (d, 1H, J=8.4 Hz), 7.18 (s, 1H), 6.34 (t, 1H, J=8.4 Hz), 3.54-3.90 (m, 6H), 3.60 (s, 3H), 2.42 (s, 3H), 2.08-2.16 (m, 1H), 1.70-1.86 (m, 2H). MS (ES) [m+H] calc'd for C$_{19}$H$_{21}$FIN$_3$O$_3$, 486; found 486.

Example 26

1-(4-((2R,3S,4S)-3,4-Dihydroxy-2-(hydroxymethyl)pyrrolidine-1-carbonyl)-5-(2-fluoro-4-iodophenylamino)-1-methyl-1H-pyrrol-2-yl)ethanone

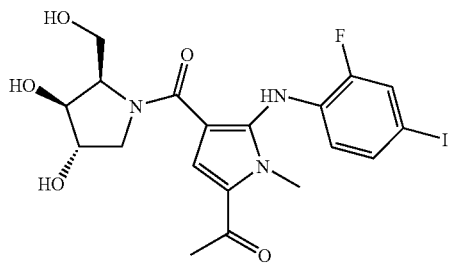

The title compound was prepared in 57% yield from Example 3 and (2R,3S,4S)-2-(hydroxymethyl)pyrrolidine-3,4-diol in a manner similar to the general procedure outlined for Example 16. $^1$H NMR (400 MHz, MeOD-d$_4$): δ 7.43 (d, 1H, J=10.8 Hz), 7.37 (s, 1H), 7.29 (dd, 1H, J=9.6, 1.2 Hz), 6.41 (t, 1H, J=8.8 Hz), 3.86-4.16 (m, 4H), 3.70 (s, 3H), 3.42-3.70 (m, 3H), 2.43 (s, 3H). MS (ES) [m+H] calc'd for C$_{19}$H$_{21}$FIN$_3$O$_5$, 518; found 518.

Example 27

1-[5-(2-Fluoro-4-iodo-phenylamino)-4-(3-hydroxy-azetidine-1-carbonyl)-1-methyl-1H-pyrrol-2-yl]-ethanone

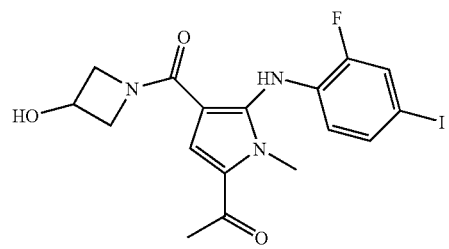

The title compound was prepared in 48% yield from Example 3 and 3-hydroxy-azetidine in a manner similar to the general procedure outlined for Example 16. $^1$H NMR (400 MHz, DMSO-d$_6$) δ ppm 8.45 (s, 1 H) 7.59 (dd, J=10.8, 1.7 Hz, 1 H) 7.33 (s, 1 H) 7.31 (d, J=8.8 Hz, 1H) 6.33 (t, J=8.8 Hz, 1 H) 4.47 (m, 2 H) 4.09 (m, 2 H) 3.65 (m, 1 H) 3.54 (s, 3 H) 2.40 (s, 3 H). MS (ES) [m+H] calc'd for C$_{17}$H$_{17}$FIN$_3$O$_3$, 458; found 458.

Example 28

1-[5-(2-Fluoro-4-iodo-phenylamino)-4-((R)-3-hydroxy-pyrrolidine-1-carbonyl)-1-methyl-1H-pyrrol-2-yl]-ethanone

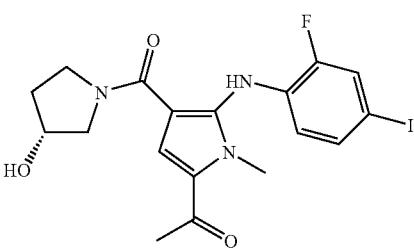

The title compound was prepared in 52% yield from Example 3 and (R)-3-hydroxy-pyrrolidine in a manner similar to the general procedure outlined for Example 16. MS (ES) [m+H] calc'd for C$_{18}$H$_{19}$FIN$_3$O$_3$, 472; found 472.

Example 29

1-[5-(2-Fluoro-4-iodo-phenylamino)-4-((S)-3-hydroxy-pyrrolidine-1-carbonyl)-1-methyl-1H-pyrrol-2-yl]-ethanone

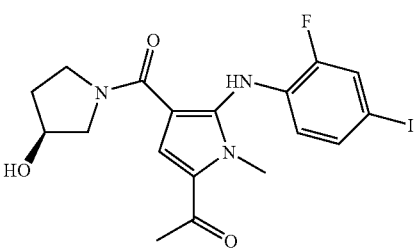

The title compound was prepared in 52% yield from Example 3 and (S)-3-hydroxy-pyrrolidine in a manner similar to the general procedure outlined for Example 16. MS (ES) [m+H] calc'd for C$_{18}$H$_{19}$FIN$_3$O$_3$, 472; found 472.

Example 30

1-[5-(2-Fluoro-4-iodo-phenylamino)-1-methyl-4-(pyrrolidine-1-carbonyl)-1H-pyrrol-2-yl]-ethanone

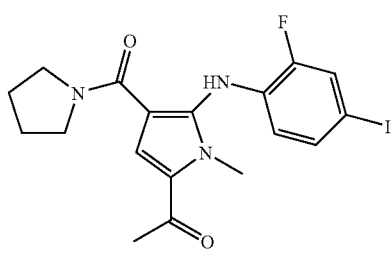

The title compound was prepared in 53% yield from Example 3 and pyrrolidine in a manner similar to the general procedure outlined for Example 16. $^1$H NMR (400 MHz, MeOD) δ ppm 7.36 (d, J=10.6 Hz, 1 H) 7.29 (s, 1 H) 7.22 (d, J=8.4 Hz, 1 H) 6.31 (t, J=8.4z, 1 H) 3.59 (s, 3 H) 3.50-3.57 (m, 2 H) 3.24-3.33 (m, 2 H) 2.34 (s, 3 H) 1.66-1.90 (m, 4 H). MS (ES) [m+H] calc'd for $C_{18}H_{19}FIN_3O_2$, 456; found 456.

Example 31

1-[5-(2-Fluoro-4-iodo-phenylamino)-4-((S)-2-hydroxymethyl-pyrrolidine-1-carbonyl)-1-methyl-1H-pyrrol-2-yl]-ethanone

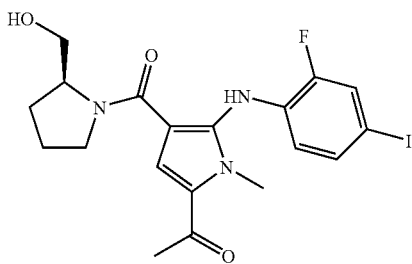

The title compound was prepared in 53% yield from Example 3 and (S)-2-hydroxymethyl-pyrrolidine in a manner similar to the general procedure outlined for Example 16. $^1$H NMR (400 MHz, DMSO-d$_6$) δ ppm 8.43 (br. s., 1 H) 7.55 (dd, J=10.9, 2.02 Hz, 1 H) 7.35 (d, J=3.5 Hz, 1 H) 7.30 (d, J=8.8 Hz, 1 H) 6.37 (t, J=8.8 Hz, 1 H) 3.87-3.99 (m, 1 H) 3.60 (s, 3H) 3.41-3.57 (m, 4 H) 3.01-3.16 (m, 1 H) 2.39 (s, 3 H) 1.63-1.93 (m, 4 H). MS (ES) [m+H] calc'd for $C_{19}H_{21}FIN_3O_3$, 486; found 486.

Example 32

1-[5-(2-Fluoro-4-iodo-phenylamino)-4-((R)-2-hydroxymethyl-pyrrolidine-1-carbonyl)-1-methyl-1H-pyrrol-2-yl]-ethanone The title compound was prepared in 54% yield from Example 3 and (R)-2-hydroxymethyl-pyrrolidine in a manner similar to the general procedure outlined for Example 16. $^1$H NMR (400 MHz, DMSO-d$_6$) δ ppm 8.43 (s, 1 H) 7.55 (dd, J=10.9, 1.9 Hz, 1 H) 7.36 (s, 1 H) 7.30 (d, J=8.8 Hz, 1 H) 6.37 (t, J=8.8 Hz, 1 H) 3.88-4.01 (m, 1 H) 3.60 (s, 3 H) 3.33-3.57 (m, 4 H) 3.04-3.16 (m, 1 H) 2.38 (s, 3 H) 1.63-1.91 (m, 4 H). MS (ES) [m+H] calc'd for $C_{19}H_{21}FIN_3O_3$, 486; found 486.

Example 33

1-[4-(3-(R)-Amino-pyrrolidine-1-carbonyl)-5-(2-fluoro-4-iodo-phenylamino)-1-methyl-1H-pyrrol-2-yl]-ethanone The title compound was prepared in 49% yield from Example 3 and 3-(R)-3-tertbutylcarbonylamino-pyrrolidine in a manner similar to the general procedure outlined for Example 16, followed by 4N HCl in dioxane deprotection and HPLC purification of the title compound. $^1$H NMR (400 MHz, DMSO-d$_6$) δ ppm 8.49 (s, 1 H) 8.05 (br. s., 3 H) 7.59 (d, J=10.6 Hz, 1 H) 7.39 (s, 1 H) 7.35 (d, J=8.8 Hz, 1 H) 6.36 (t, J=8.8 Hz, 1 H) 4.12-4.16 (m, 1H) 3.77-3.84 (m, 2H) 3.57 (s, 3 H) 2.65-2.69 (m, 2 H) 2.41 (s, 3 H) 2.30-2.35 (m, 2 H). MS (ES) [m+H] calc'd for $C_{18}H_{20}FIN_4O_2$, 487; found 487.

Example 34

Methanesulfonic acid 1-[5-acetyl-2-(2-fluoro-4-iodo-phenylamino)-1-methyl-1H-pyrrole-3-carbonyl]-azetidin-3-yl ester

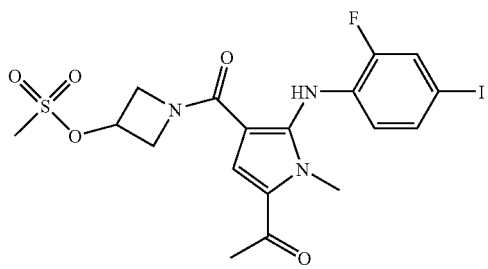

Methane sulfonyl chloride (0.026 ml, 0.33 mmol) was added dropwise at 0° C. to a stirred solution of Example 27 (102 mg, 0.22 mmol) and triethyl amine (0.047 ml, 0.33 mmol) in $CH_2Cl_2$ (1.2 mL). After stirring for 10 min at 0° C., the reaction mixture was allowed to warm up at room temperature. After stirring for 2 hours, the reaction mixture was washed with a saturated solution of $NaHCO_3$, extracted with $CH_2Cl_2$. The organics were washed with and brine, dried ($MgSO_4$), and concentrated. Purification by silica gel chromatography gave 100 mg (84%) of the title compound as beige solid. MS (ES) [m+H] calc'd for $C_{18}H_{19}FIN_3O_5S$, 536; found 536.

Example 35

1-{5-(2-Fluoro-4-iodo-phenylamino)-4-[3-(2-hydroxy-ethylamino)-azetidine-1-carbonyl]-1-methyl-1H-pyrrol-2-yl}-ethanone

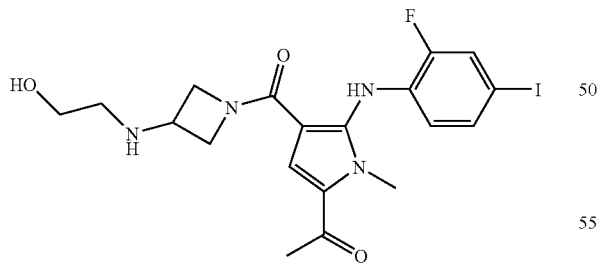

Example 34 (20 mg, 0.375 mmol) and ethanolamine (0.045 ml, 0.45 mmol) were stirred in dry DMF (0.1 mL) at 100° C. for 2 days. Purification by preparative HPLC mass triggered gave 3.1 mg (16%) of the title compound as a colorless oil. $^1$H NMR (400 MHz, MeOD) δ ppm 7.52 (dd, J=10.5, 1.9 Hz, 1 H) 7.39 (d, J=8.7 Hz, 1 H) 7.34 (s, 1 H) 6.39 (t, J=8.7 Hz, 1 H) 4.20-4.28 (m, 2 H) 3.78-3.86 (m, 2 H) 3.66 (s, 3 H) 3.32-3.34 (m, 3H) 3.11-3.21 (m, 2 H) 2.48 (s, 3 H). MS (ES) [m+H] calc'd for $C_{19}H_{22}FIN_4O_3$, 501; found 501.

Example 36

1-(5-(2-Fluoro-4-iodo-phenylamino)-4-{3-[(2-hydroxy-ethyl)-methyl-amino]-azetidine-1-carbonyl}-1-methyl-1H-pyrrol-2-yl)-ethanone

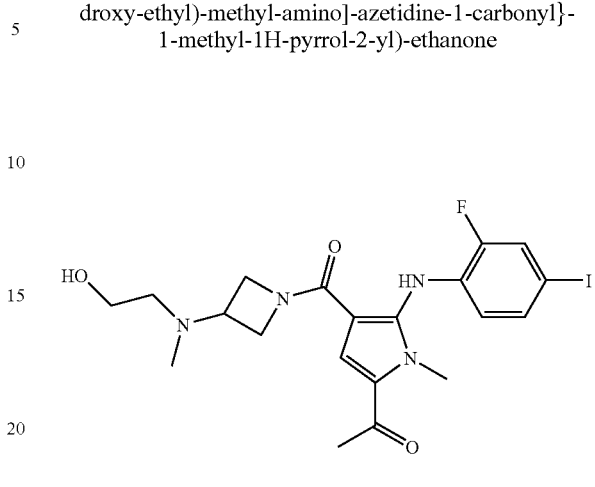

The title compound was prepared in 31% yield from Example 34 and 2-methylaminoethanol in a manner similar to the general procedure outlined for Example 35. $^1$H NMR (400 MHz, MeOD) δ ppm 7.40 (dd, J=10.61, 1.77 Hz, 1 H) 7.27 (dd, J=8.46, 1.14 Hz, 1 H) 7.24 (s, 1H) 6.27 (t, J=8.59 Hz, 1 H) 4.13-4.27 (m, 2 H) 3.69-3.83 (m, 2 H) 3.54 (s, 3 H) 3.20-3.22 (m, 3H) 3.16 (m, 2 H) 2.83 (s, 3 H) 2.37 (s, 3 H). MS (ES) [m+H] calc'd for $C_{20}H_{24}FIN_4O_3$, 515; found 515.

Example 37

1-[4-(3-Dimethylamino-azetidine-1-carbonyl)-5-(2-fluoro-4-iodo-phenylamino)-1-methyl-1H-pyrrol-2-yl]-ethanone

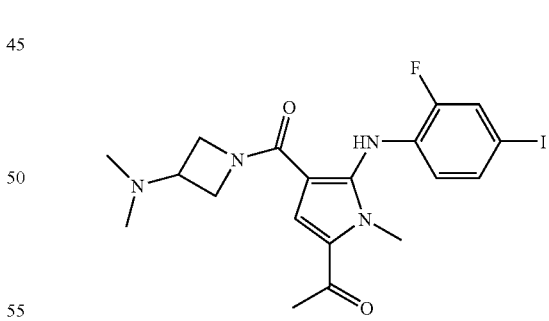

The title compound was prepared in 18% yield from Example 34 and dimethylamine in THF (2N, 0.375 ml) in a manner similar to the general procedure outlined for Example 16. $^1$H NMR (400 MHz, MeOD) δ ppm 7.40 (dd, J=10.5, 1.6 Hz, 1 H) 7.3 (dd, J=8.7, 0.9 Hz, 1 H) 7.2 (s, 1 H) 6.3 (t, J=8.7 Hz, 1 H) 3.9-4.1 (m, 2 H) 3.5 (s, 3 H) 3.1-3.3 (m, 3H) 2.8 (s, 6 H) 2.4 (s, 3H). MS (ES) [m+H] calc'd for $C_{19}H_{22}FIN_4O_2$, 485; found 485.

Example 38

1-[5-(2-Fluoro-4-iodo-phenylamino)-4-(3-hydroxy-3-hydroxymethyl-azetidine-1-carbonyl)-1-methyl-1H-pyrrol-2-yl]-ethanone

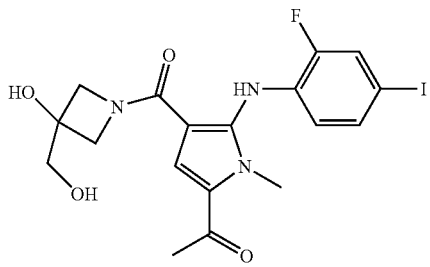

The title compound was prepared in 55% yield from Example 3 and 3-hydroxy-3-hydroxymethyl-azetidine ((see, WO2007/044515) in a manner similar to the general procedure outlined for Example 16. $^1$H NMR (400 MHz, DMSO-$d_6$) δ ppm 8.48 (s, 1 H) 7.59 (d, J=11.1 Hz, 1 H) 7.34 (d, J=8.7 Hz, 1 H) 6.34 (t, J=8.7 Hz, 1 H) 4.27-4.38 (m, 1 H) 4.03-4.15 (m, 1 H) 3.86-3.98 (m, 1 H) 3.55-3.77 (m, 1 H) 3.52-3.56 (m, 2 H) 3.38 (s, 3 H) 2.41 (s, 3 H). MS (ES) [m+H] calc'd for $C_{18}H_{19}FIN_3O_4$, 488; found 488.

Example 39

Ethyl 5-acetyl-4-fluoro-2-(2-fluoro-4-iodophenylamino)-1-methyl-1H-pyrrole-3-carboxylate

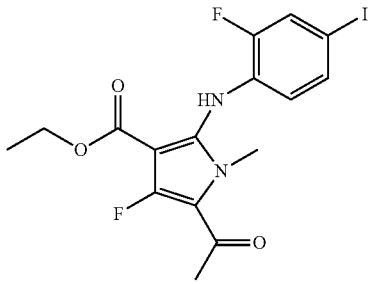

Example 9b (50 mg, 0.11 mmol) was added to a 2-5 mL microwave vial with cesium fluoride (167 mg, 1.10 mmol) in DMSO (2.5 mL). The vial was heated under microwave irradiation at 180° C. for 30 minutes. The solution was diluted with H$_2$O and extracted (3×) with Et$_2$O. Organics were dried (MgSO$_4$) and concentrated in vacuo. Purification by silica gel chromatography (30% EtOAc/Hexanes) gave 4 mg (9%) of the title compound as a brown solid. $^1$H NMR (400 MHz, CDCl$_3$): δ 7.47 (s, 1H), 7.51 (dd, 1H, J=8.0, 1.8 Hz), 7.46 (dd, 1H, J=9.8, 1.8 Hz), 6.43 (t, 1H, J=8.5 Hz), 4.13 (q, 2H, J=7.2 Hz), 3.51 (s, 3H), 2.78 (s, 3H), 1.35 (t, 3H, J=7.1 Hz). MS (ES) [m+H] calc'd for, $C_{16}H_{15}F_2IN_2O_3$, 449; found 449.

Example 40

5-Acetyl-4-fluoro-2-(2-fluoro-4-iodophenylamino)-1-methyl-1H-pyrrole-3-carboxylic acid

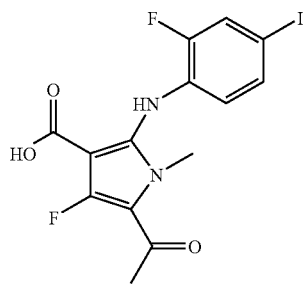

Example 39 (160 mg, 0.36 mmol) was stirred in dioxane (10 mL) and 1M NaOH (10 mL) at 50° C. for 1 hr. The cooled solution was made acidic with 1N HCl and extracted (3×) with ethyl acetate. Organics were dried (MgSO$_4$) and concentrated in vacuo. Purification by silica gel chromatography (10% MeOH/CH$_2$Cl$_2$) gave 97 mg (65%) of the title compound as a tan solid. $^1$H NMR (400 MHz, CDCl$_3$): δ 7.42-7.51 (m, 1H), 7.37 (d, 1H, J=9.4 Hz), 6.45 (m, 1H), 3.51 (s, 3H), 2.49 (s, 3H). MS (ES) [m+H] calc'd for, $C_{14}H_{11}F_2IN_2O_3$, 421; found 421.

Example 41

(R)-5-Acetyl-N-(2,3-dihydroxypropoxy)-4-fluoro-2-(2-fluoro-4-iodophenylamino)-1-methyl-1H-pyrrole-3-carboxamide

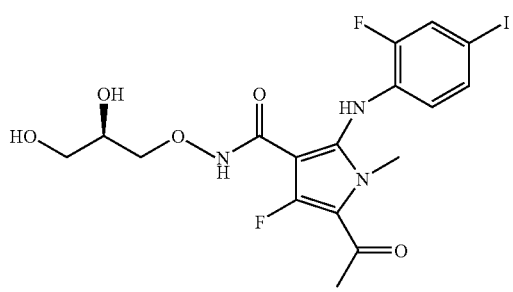

Example 40 (8 mg, 0.019 mmol), (R)-(2,2-dimethyl-1,3-dioxolan-4-yl)methoxyamine (see Bailey et al., *J. Med. Chem.*, 34, 1991, 51-65; 8 mg, 0.057 mmol), and HOBt (3 mg, 0.021 mmol) were stirred in CH$_2$Cl$_2$ (2 mL) at room temperature. EDC (5 mg, 0.029 mmol) and then triethylamine (8 µL, 0.057 mmol) were added, and the reaction stirred for 16 h. The solution was washed with 0.1N HCl and brine, dried (MgSO$_4$), and concentrated in vacuo. The residue was stirred in MeOH (2 mL) and water (200 µL) with p-toluenesulfonic acid (5 mg, 0.026 mmol) for 4 h. Triethylamine (50 µL) was added and the solution was concentrated in vacuo. Purification by silica gel chromatography (10% MeOH/CH$_2$Cl$_2$) gave 1 mg (12%) of the title compound as a white solid. $^1$H NMR (400 MHz, CDCl$_3$): δ 9.44 (s, 1H), 7.98 (s, 1H), 7.46 (dd, 1H, J=9.7, 1.4 Hz), 7.36 (d, 1H, J=8.3 Hz), 6.47 (t, 1H, J=8.6 Hz), 4.66 (s, 1H), 3.89-4.17 (m, 3H), 3.59-3.79 (m, 2H), 3.47 (s, 3H), 2.46 (d, 3H, J=3.5 Hz). MS (ES) [m+H] calc'd for C$_{17}$H$_{18}$F$_2$IN$_3$O$_5$, 510; found 510.

Example 42

(S)-5-acetyl-N-(2,3-dihydroxypropoxy)-4-fluoro-2-(2-fluoro-4-iodophenylamino)-1-methyl-1H-pyrrole-3-carboxamide

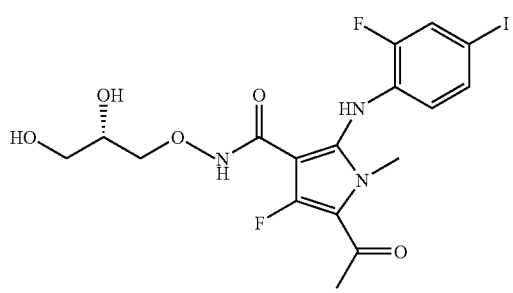

Example 40 (8 mg, 0.019 mmol), (S)-(2,2-dimethyl-1,3-dioxolan-4-yl)methoxyamine (see Bailey et al., *J. Med. Chem.*, 34, 1991, 51-65; 8 mg, 0.057 mmol), and HOBt (3 mg, 0.021 mmol) were stirred in CH$_2$Cl$_2$ (2 mL) at room temperature. EDC (5 mg, 0.029 mmol) and then triethylamine (8 µL, 0.057 mmol) were added and the reaction stirred for 16 h. The solution was washed with 0.1N HCl and brine, dried (MgSO$_4$), and concentrated in vacuo. The residue was stirred in MeOH (2 mL) and water (200 µL) with p-toluenesulfonic acid (5 mg, 0.026 mmol) for 4 h. Triethylamine (50 µL) was added, and the solution was concentrated in vacuo. Purification by silica gel chromatography (10% MeOH/CH$_2$Cl$_2$) gave 2 mg (21%) of the title compound as a white solid. $^1$H NMR (400 MHz, CDCl$_3$): δ 8.74 (d, 1H, J=6.3 Hz), 7.97 (s, 1H), 7.46 (dd, 1H, J=10.0, 1.9 Hz), 7.34-7.39 (m, 1H), 6.48 (t, 1H, J=8.6 Hz), 4.65 (s, 1H), 3.91-4.11 (m, 3H), 3.58-3.80 (m, 2H), 3.47 (s, 3H), 2.46 (d, 3H, J=4.0 Hz). MS (ES) [m+H] calc'd for C$_{17}$H$_{18}$F$_2$IN$_3$O$_5$, 510; found 510.

Example 43

5-Acetyl-2-(4-bromo-2-fluorophenylamino)-N-(2-hydroxyethoxy)-1-methyl-1H-pyrrole-3-carboxamide

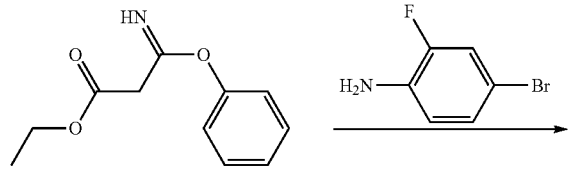

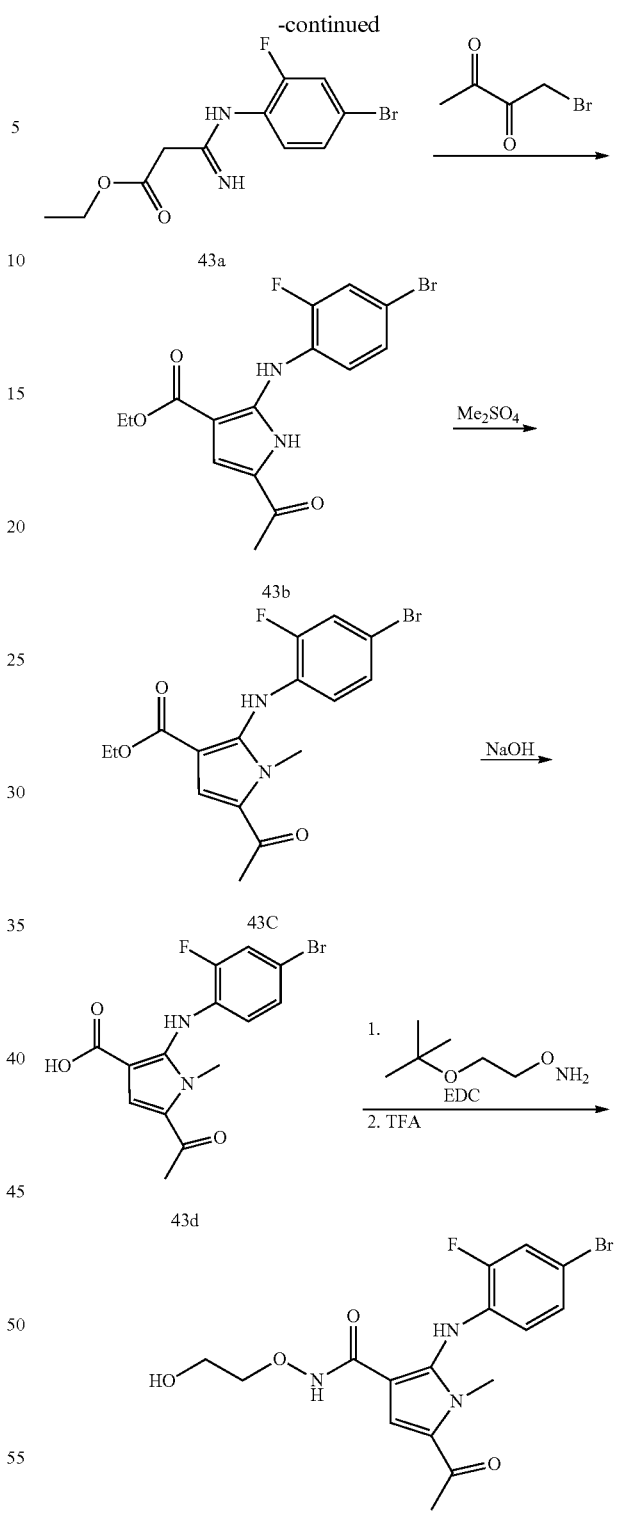

Example 43

Ethyl 3-(4-bromo-2-fluorophenylamino)-3-iminopropanoate: 4 Bromo-2-fluoro-aniline (11.4 g, 46.7 mmol) was added to a suspension of ethyl 3-imino-3-phenoxypropionate, hydrochloride (see, Danswan et al., *J. Heterocyclic Chem.*, 26, 1989, 293-299; 3.42 g, 14.0 mmol) in EtOAc (50 mL). The reaction was stirred at reflux for 2 h and then concentrated in vacuo. The residue was taken up in ether, and the precipitate was collected by filtration to give 15.3 g (96%) of the hydrochloride salt of the title compound as a white solid. $^1$H NMR (400 MHz, CDCl$_3$): δ 7.15-7.25 (m, 2H), 6.80-6.83 (m, 1H), 4.12 (q, 2H, J=7.0 Hz), 3.36 (s, 2H), 1.26 (t, 3H, J=7.2 Hz). MS (ES) [m+H] calc'd for C$_{11}$H$_{12}$BrFN$_2$O$_2$, 303; found 303. (The free base can be obtained by washing an organic solution of the title compound with sat. NaHCO$_3$ solution.)

Ethyl 5-acetyl-2-(4-bromo-2-fluorophenylamino)-1H-pyrrole-3-carboxylate: Compound 43a (free base, 2.85 g, 9.4 mmol) and 1-bromobutane-2,3-dione (1.7 g, 10.4 mmol) were stirred in THF at room temperature for 18 h. The solution was concentrated in vacuo. Purification by silica gel chromatography (30% EtOAc/Hexanes) gave 708 mg (20%) of the title compound as a white solid. $^1$H NMR (400 MHz, CDCl$_3$): δ 8.95 (s, 1H), 8.59 (s, 1H), 7.36 (dd, 1H, J=10.0, 2.2 Hz), 7.29-7.33 (m, 1H), 7.24-7.28 (m, 1H), 7.17 (s, 1H), 4.33 (q, 2H, J=7.1 Hz), 2.35 (s, 3H), 1.39 (t, 3H, J=5.1). MS (ES) [m+H] calc'd for C$_{15}$H$_{14}$BrFN$_2$O$_3$, 369; found 369.

Ethyl 5-acetyl-2-(4-bromo-2-fluorophenylamino)-1-methyl-1H-pyrrole-3-carboxylate: Compound 43b (700 mg, 1.9 mmol), cesium carbonate (926 mg, 2.8 mmol), and dimethylsulfate (270 µL, 2.8 mmol) were stirred in DMF (10 mL) at 50° C. for 4 h. The solution was diluted with H$_2$O and extracted (3×) with Et$_2$O. Organics were dried (MgSO$_4$) and concentrated in vacuo. Purification by silica gel chromatography (30% EtOAc/Hexanes) gave 653 mg (90%) of the title compound as a white solid. $^1$H NMR (400 MHz, CDCl$_3$): δ 7.36 (s, 1H), 7.28 (dd, 1H, J=10.3, 2.3 Hz), 7.21 (m, 1H), 7.13 (dt, 1H, J=8.6, 1.8 Hz), 6.44 (t, 1H, J=8.7 Hz), 4.27 (q, 2H, J=7.1 Hz), 3.62 (s, 3H), 2.45 (s, 3H), 1.33 (t, 3H, J=7.1 Hz). MS (ES) [m+H] calc'd for C$_{16}$H$_{16}$BrFN$_2$O$_3$, 383; found 383.

5-Acetyl-2-(4-bromo-2-fluorophenylamino)-1-methyl-1H-pyrrole-3-carboxylic acid: Compound 43c (653 mg, 1.7 mmol) was stirred in MeOH (12 mL) with 1N NaOH (6 mL) at 60° C. for 16 h. The cooled solution was made acidic with 1N HCl and extracted (3×) with CHCl$_3$. Organics were dried (MgSO$_4$) and concentrated in vacuo. Purification by silica gel chromatography (10% MeOH/CH$_2$Cl$_2$) gave 207 mg (34%) of the title compound as a white solid. $^1$H NMR (400 MHz, CDCl$_3$): δ 7.40 (s, 1H), 7.28 (dd, 1H, J=10.1, 2.2 Hz), 7.21 (m, 1H), 7.14-7.16 (m, 1H), 6.49 (t, 1H, J=8.7 Hz), 3.59 (s, 3H), 2.45 (m, 3H). MS (ES) [m+H] calc'd for C$_{14}$H$_{12}$BrFN$_2$O$_3$, 355; found 355.

5-Acetyl-2-(4-bromo-2-fluorophenylamino)-N-(2-hydroxyethoxy)-1-methyl-1H-pyrrole-3-carboxamide: Compound 43d (65 mg, 0.18 mmol), O-(2-tert-butoxy-ethyl)-hydroxylamine (see, WO05/110410, 73 mg, 0.55 mmol), and HOBt (27 mg, 0.20 mmol) were stirred in CH$_2$Cl$_2$ (4 mL) at room temperature. EDC (82 mg, 0.27 mmol) and then triethylamine (77 µL, 0.55 mmol) were added, and the reaction stirred for 16 h. The solution was washed with 0.1N HCl and brine, dried (MgSO$_4$), and concentrated in vacuo. The residue was stirred in TFA (2 mL) for 1 h. The solution was diluted with H$_2$O and extracted (3×) with chloroform. Organics were dried (MgSO$_4$) and concentrated in vacuo. Purification by silica gel chromatography (10% MeOH/CH$_2$Cl$_2$) gave 36 mg (48%) of Example 43 as a white solid. $^1$H NMR (400 MHz, CDCl$_3$): δ 9.00 (s, 1H), 7.52 (s, 1H), 7.28 (dd, 1H, J=10.4, 2.3 Hz), 7.19 (s, 1H), 7.13 (dt, 1H, J=8.6, 1.6 Hz), 6.45 (t, 1H, J=8.7 Hz), 3.94-4.02 (m, 2H), 3.68-3.79 (m, 2H), 3.59 (s, 3H), 2.43 (s, 3H). MS (ES) [m+H] calc'd for C$_{16}$H$_{17}$BrFN$_3$O$_4$, 414; found 414.

In addition to the foregoing, the above reaction schemes, and variations thereof, can be used to prepare the following:

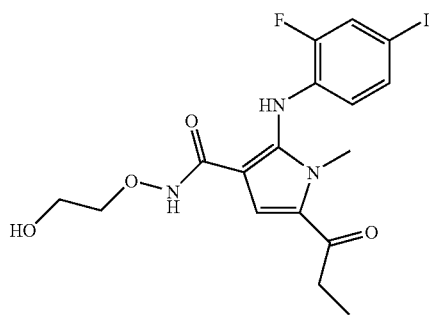

2-(2-fluoro-4-iodophenylamino)-N-(2-hydroxyethoxy)-1-methyl-5-propionyl-1H-pyrrole-3-carboxamide

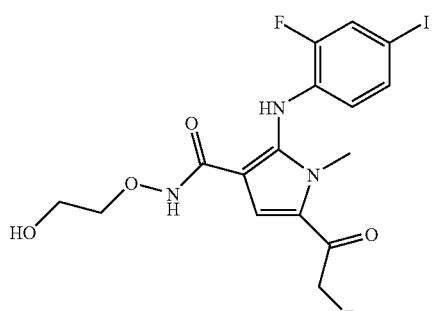

2-(2-fluoro-4-iodophenylamino)-5-(2-fluoroacetyl)-N-(2-hydroxyethoxy)-1-methyl-1H-pyrrole-3-carboxamide

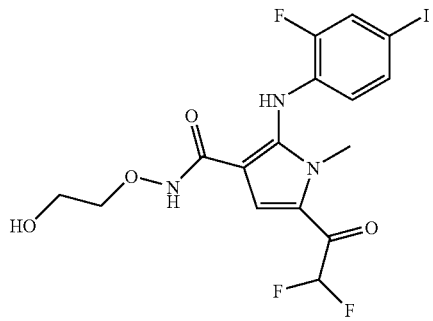

5-(2,2-difluoroacetyl)-2-(2-fluoro-4-iodophenylamino)-N-(2-hydroxyethoxy)-1-methyl-1H-pyrrole-3-carboxamide

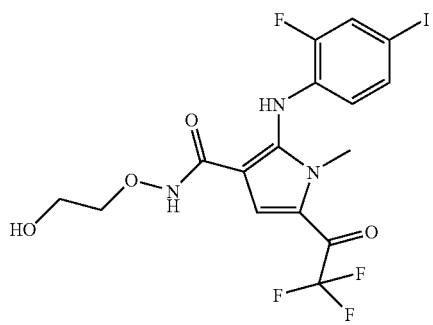

2-(2-fluoro-4-iodophenylamino)-N-(2-hydroxyethoxy)-1-methyl-5-(2,2,2-trifluoroacetyl)-1H-pyrrole-3-carboxamide

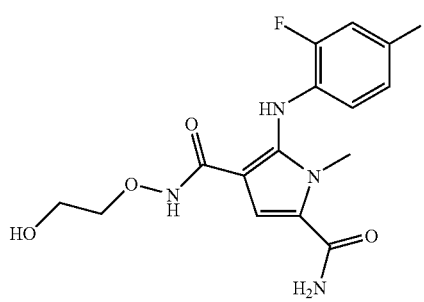

5-(2-fluoro-4-iodophenylamino)-N4-(2-hydroxyethoxy)-1-methyl-1H-pyrrole-2,4-dicarboxamide

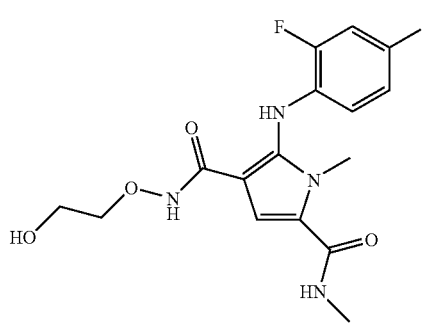

5-(2-fluoro-4-iodophenylamino)-N4-(2-hydroxyethoxy)-N2,1-dimethyl-1H-pyrrole-2,4-dicarboxamide

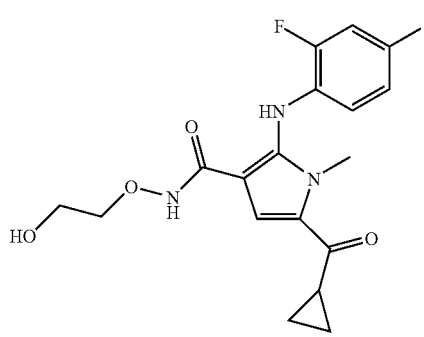

5-(cyclopropanecarbonyl)-2-(2-fluoro-4-iodophenylamino)-N-(2-hydroxyethoxy)-1-methyl-1H-pyrrole-3-carboxamide

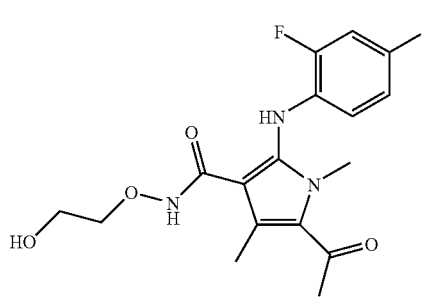

5-acetyl-2-(2-fluoro-4-iodophenylamino)-N-(2-hydroxyethoxy)-1,4-dimethyl-1H-pyrrole-3-carboxamide

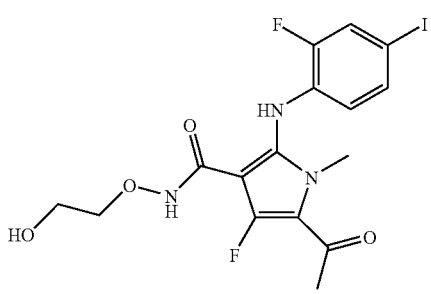

5-acetyl-4-fluoro-2-(2-fluoro-4-iodophenylamino)-N-(2-hydroxyethoxy)-1-methyl-1H-pyrrole-3-carboxamide

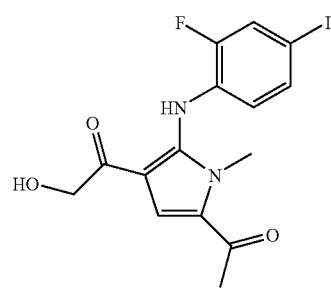

1-(5-acetyl-2-(2-fluoro-4-iodophenylamino)-1-methyl-1H-pyrrol-3-yl)-2-hydroxyethanone

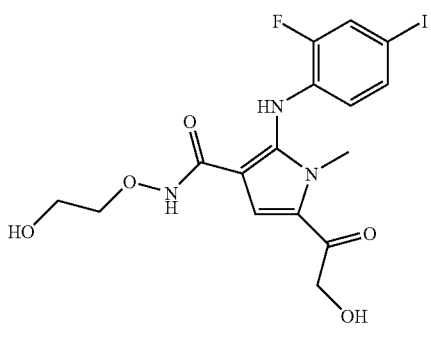

2-(2-fluoro-4-iodophenylamino)-5-(2-hydroxyacetyl)-N-(2-hydroxyethoxy)-1-methyl-1H-pyrrole-3-carboxamide

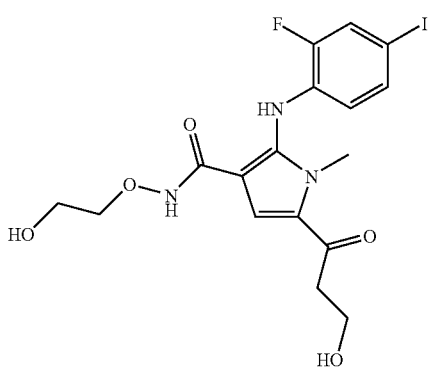

2-(2-fluoro-4-iodophenylamino)-N-(2-hydroxyethoxy)-5-(3-hydroxypropanoyl)-1-methyl-1H-pyrrole-3-carboxamide

97
-continued

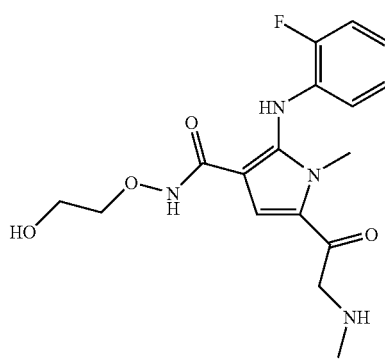

2-(2-fluoro-4-iodophenylamino)-N-(2-hydroxyethoxy)-1-methyl-5-(2-(methylamino)acetyl)-1H-pyrrole-3-carboxamide

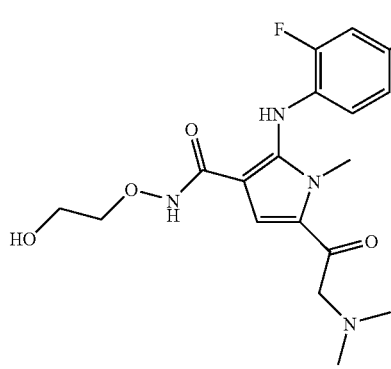

5-(2-(dimethylamino)acetyl)-2-(2-fluoro-4-iodophenylamino)-N-(2-hydroxyethoxy)-1-methyl-1H-pyrrole-3-carboxamide

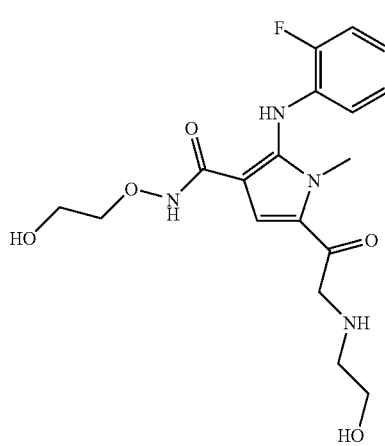

2-(2-fluoro-4-iodophenylamino)-N-(2-hydroxyethoxy)-5-(2-(2-hydroxyethylamino)acetyl)-1-methyl-1H-pyrrole-3-carboxamide

98
-continued

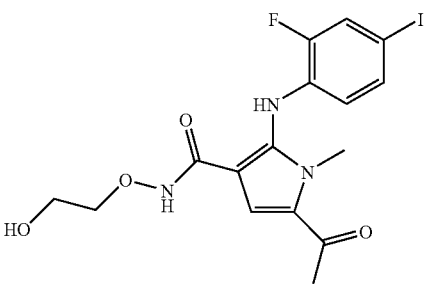

2-acetyl-5-(2-fluoro-4-iodophenylamino)-N-(2-hydroxyethoxy)-1-methyl-1H-imidazole-4-carboxamide

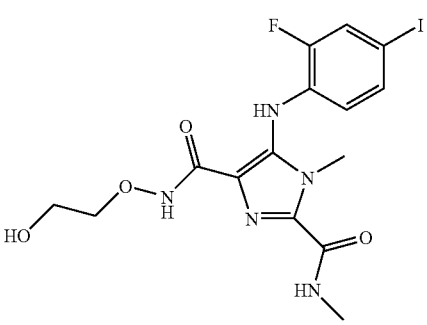

5-(2-fluoro-4-iodophenylamino)-N4-(2-hydroxyethoxy)-N2,1-dimethyl-1H-imidazole-2,4-dicarboxamide

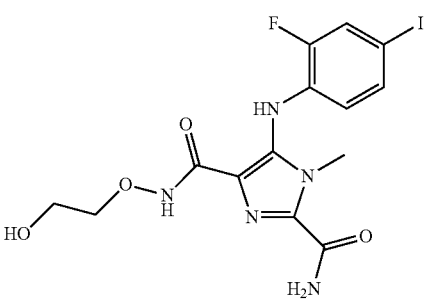

5-(2-fluoro-4-iodophenylamino)-N4-(2-hydroxyethoxy)-1-methyl-1H-imidazole 2,4-dicarboxamide

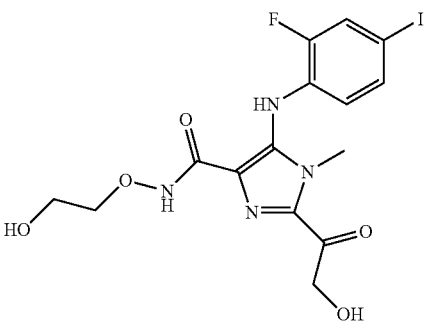

5-(2-fluoro-4-iodophenylamino)-2-(2-hydroxyacetyl)-N-(2-hydroxyethoxy)-1-methyl-1H-imidazole-4-carboxamide 99
-continued

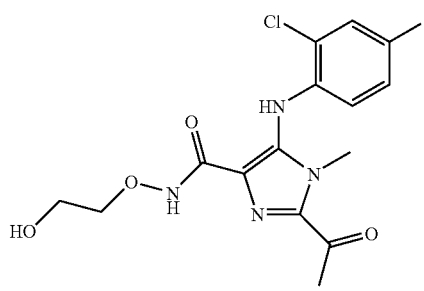

5-acetyl-2-(2-chloro-4-iodophenylamino)-
N-(2-hydroxyethoxy)-1-methyl-1H-
pyrrole-3-carboxamide

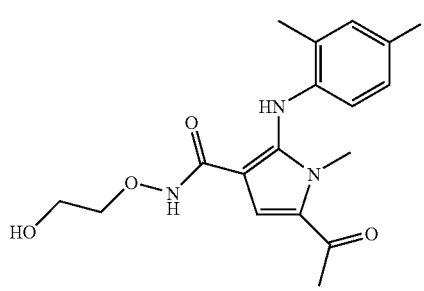

5-acetyl-N-(2-hydroxyethoxy)-2-(4-iodo-2-
methylphenylamino)-1-methyl-1H-pyrrole-
3-carboxamide

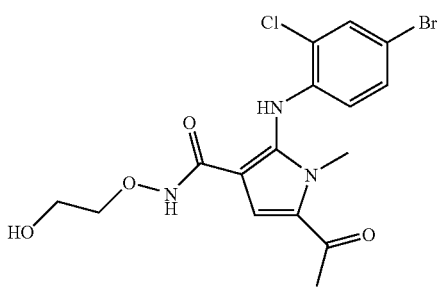

5-acetyl-2-(4-bromo-2-
chlorophenylamino)-N-(2-hydroxyethoxy)-
1-methyl-1H-pyrrole-3-carboxamide

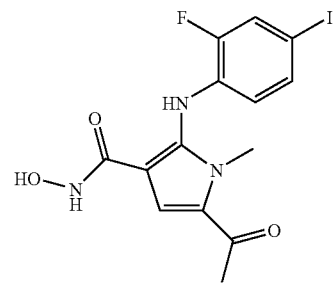

5-acetyl-2-(2-fluoro-4-iodophenylamino)-
N-hydroxy-1-methyl-1H-pyrrole-3-
carboxamide 100
-continued

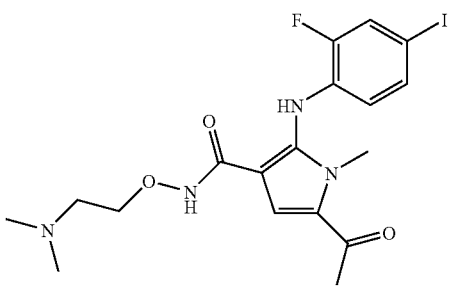

5-acetyl-N-(2-(dimethylamino)ethoxy)-2-
(2-fluoro-4-iodophenylamino)-1-methyl-
1H-pyrrole-3-carboxamide

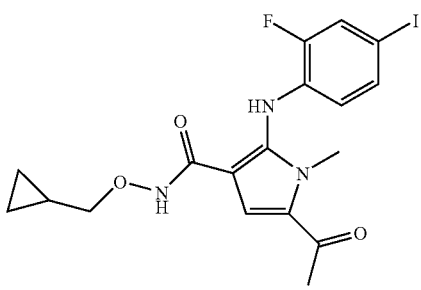

5-acetyl-N-(cyclopropylmethoxy)-2-(2-
fluoro-4-iodophenylamino)-1-methyl-1H-
pyrrole-3-carboxamide

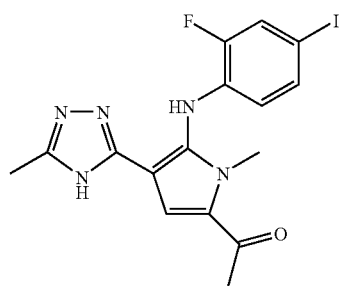

1-(5-(2-fluoro-4-iodophenylamino)-1-
methyl-4-(5-methyl-4H-1,2,4-triazol-3-yl)-
1H-pyrrol-2-yl)ethanone

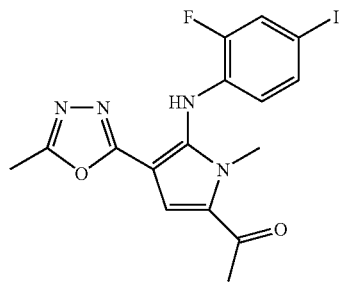

1-(5-(2-fluoro-4-iodophenylamino)-1-
methyl-4-(5-methyl-1,3,4-oxadiazol-2-yl)-
1H-pyrrol-2-yl)ethanone

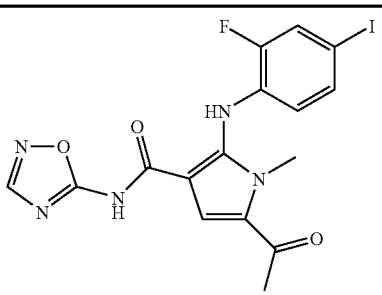

5-acetyl-2-(2-fluoro-4-iodophenylamino)-
1-methyl-N-(1,2,4-oxadiazol-5-yl)-1H-
pyrrole-3-carboxamide

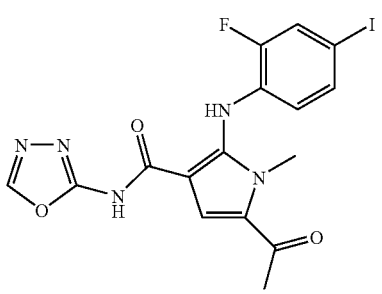

5-acetyl-2-(2-fluoro-4-iodophenylamino)-
1-methyl-N-(1,3,4-oxadiazol-2-yl)-1H-
pyrrole-3-carboxamide

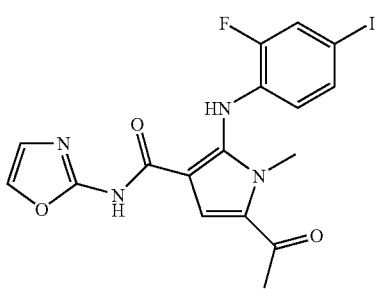

5-acetyl-2-(2-fluoro-4-iodophenylamino)-
1-methyl-N-(oxazol-2-yl)-1H-pyrrole-3-
carboxamide

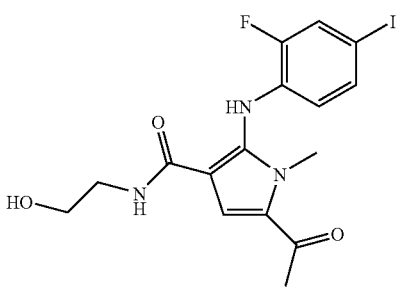

5-acetyl-2-(2-fluoro-4-iodophenylamino)-
N-(2-hydroxyethyl)-1-methyl-1H-pyrrole-3-
carboxamide Biological Testing The activity of compounds as MEK inhibitors may be assayed in vitro, in vivo or in a cell line. Further, compounds according to the present invention may be screened for activity against one or more MEKs. Provided below are assays for activity against MEK1 and ERK1.

Purified MEK1, MEK2 and ERK1 may be obtained as follows.

For MEK1, DNA encoding residues 2-393 (del aa 32-51, S218E/S222D) of the full-length sequence of the human enzyme may be amplified by PCR and cloned into the BamHI/XbaI sites of pFastbac (Invitrogen), which incorporates a 6-histidine tag at the N-terminus. The deletion from residues 32-51, and the two mutations, S218E and S222D, may be obtained by quick change PCR. SEQ ID NO: 1 corresponds to residues 2-393, with deletion from residues 32-51 and mutations S218E/S222D, and with the N-terminal 6-histidine tag. SEQ ID NO: 2 is the DNA sequence that was used to encode SEQ ID NO: 1.

For MEK2, DNA encoding residues 1-400 (S222E/S226D) of the full-length sequence of the human enzyme may be amplified by PCR and cloned into pFastbac (Invitrogen), which incorporates a 6-histidine tag at the N-terminus. The two mutations, S222E and S226D, may be obtained by quick change PCR. SEQ ID NO: 3 corresponds to residues 1-400 with mutations S222E/S226D, and with the N-terminal 6-histidine tag and SEQ. I.D. No. 4 is the DNA sequence that was used to encode SEQ ID NO: 3.

For ERK1, DNA encoding residues 1-379 of the full-length sequence of the human enzyme may be amplified by PCR and cloned into the SmalI/SalI sites of pGEX-6p-3 (GE Healthcare), which incorporates a GST tag at the N-terminus. SEQ ID NO: 5 corresponds to residues 1-379 with the N-terminal GST tag. SEQ ID NO: 6 is the DNA sequence that was used to encode SEQ ID NO: 5.

Recombinant baculovirus incorporating the MEK1 and MEK2 constructs may be generated by transposition using the Bac-to-Bac system (Invitrogen). High-titer viral stocks may be generated by infection of *Spodoptera frugiperda* Sf9 cells; the expression of recombinant protein may be carried out by infection of *Spodoptera frugiperda* Sf9 (Invitrogen) in 5 L Wave Bioreactors (Wave Biotech).

Recombinant protein may be isolated from cellular extracts by passage over ProBond resin (Invitrogen). Partially purified extracts of all MEK1 may then be further purified by high pressure liquid chromatography over a SEC2000 gel filtration resin. The purity of MEK1 and MEK2 proteins may be determined on denaturing SDS-PAGE gel. Purified MEK1 and MEK2 may then be concentrated to a final concentration of 3.4 mg/ml and 5.4 mg/ml, respectively. The proteins may be either stored at −78° C. in a buffer containing 50 mM TRIS-HCl pH 7.6, 250 mM NaCl, 0.1 mM EDTA and 0.125 mM TCEP or at −20° C. in the presence of glycerol (final concentration of glycerol at 50%).

Recombinant protein incorporating the ERK1 constructs may be generated by transformation of the expression vector into an *E. coli* strain HD5α (Invitrogen). To express ERK1 protein, the transformated *E. coli* strain may be cultured at 37° C. C until OD0.6, and then induced by adding IPTG to final concentration of 0.5 mM, and continue to culture the cell overnight at 25° C.

Recombinant ERK1 protein may be isolated from cellular extracts by passage over Glutathione (Amersham). Partially purified extracts of ERK1 may then be further purified by high pressure liquid chromatography over a BioSep SEC3000 gel filtration resin. The purity of ERK1 protein may be determined on denaturing SDS-PAGE gel. Purified ERK1 may then be concentrated to a final concentration of 1.9 mg/ml. The proteins may be either stored at −78° C. in a buffer containing 25 mM TRIS-HCl pH 7.6, 150 mM NaCl, 1 mM EDTA and 0.25 mM TCEP or at −20° C. in the presence of glycerol (final concentration of glycerol at 50%).

It should be noted that a variety of other expression systems and hosts are also suitable for the expression of MEK1 and ERK1, as would be readily appreciated by one of skill in the art.

The inhibitory properties of compounds relative to MEK1 or MEK2 may be determined using a black 384-well-plate format under the following reaction conditions: 50 mM HEPES pH 7.3, 10 mM NaCl, 10 mM MgCl$_2$, 0.01% Brij35, 1 nM MEK1 or 4 nM MEK2, 25 nM ERK1, 400 µM ATP, 500 nM IPTTPITTYFFFK-5FAM-COOH (FI-Erktide), and 1% DMSO. Reaction product is determined quantitatively by fluorescent polarization using progressive IMAP beads from Molecular Devices.

The assay reaction may be initiated as follows: 2 µl of the mixture of 1.5 µM FI-Erktide and 75 nM ERK with 2 µl of inhibitor (2 fold serial dilutions for 11 data points for each inhibitor) containing 3% DMSO were added to each well of the plate, followed by the addition of 2 µl of the mixture of 3 nM MEK1 or 12 nM MEK2 and 1200 µM ATP to initiate the reaction (final enzyme concentration was 1 nM for MEK1 or 4 nM for MEK2). The reaction mixture may then be incubated at room temperature for 22 min, and quenched and developed by addition of 20 µl of 1:200 dilution of progressive IMAP beads (Molecular Devices) in 80% buffer A, 20% buffer B and 0.003% Tween 20. Fluorescence polarization of the resulting reaction mixtures may be measured after a 1 hour incubation at room temperature.

IC$_{50}$ values may be calculated by non-linear curve fitting of the compound concentrations and fluorescence intensities to the standard IC$_{50}$ equation. IC$_{50}$ values for select compounds of the present invention are given in Table 1.

TABLE 1

IC$_{50}$ of Exemplified Compounds Against MEK1

| Example | IC$_{50}$ (nM) |
| --- | --- |
| 2 | >151 |
| 3 | 41-80 |
| 4 | <40 |
| 5 | 41-80 |
| 6 | <40 |
| 7 | <40 |
| 8 | 81-150 |
| 9 | 41-80 |
| 10 | <40 |
| 11 | <40 |
| 12 | <40 |
| 13 | 41-80 |
| 14 | <40 |
| 15 | 41-80 |
| 16 | 81-150 |
| 17 | 81-150 |
| 18 | <40 |
| 19 | 41-80 |
| 20 | <40 |
| 21 | 41-80 |
| 22 | <40 |
| 23 | >151 |
| 24 | 41-80 |
| 25 | >151 |
| 26 | <40 |
| 27 | <40 |
| 28 | <40 |
| 29 | 81-150 |
| 30 | >151 |
| 31 | >151 |
| 32 | >151 |
| 33 | <40 |
| 35 | 81-150 |
| 36 | >151 |
| 37 | >151 |
| 38 | 41-80 |
| 41 | <40 |
| 42 | <40 |
| 43 | 41-80 |

It will be apparent to those skilled in the art that various modifications and variations can be made in the compounds, compositions, kits, and methods of the present invention without departing from the spirit or scope of the invention. Thus, it is intended that the present invention cover the modifications and variations of this invention provided they come within the scope of the appended claims and their equivalents.

What is claimed is:

1. A compound represented by the formula:

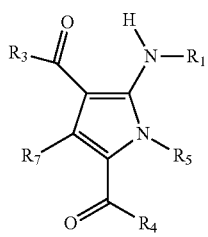

or an ester, tautomer, enantiomer, pharmaceutically acceptable salt or prodrug thereof,
wherein $R_1$ is selected from the group consisting of $(C_{3-12})$cycloalkyl, hetero$(C_{3-12})$cycloalkyl, $(C_{9-12})$bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted;

$R_3$ is selected from the group consisting of hydroxy, amino, $(C_{1-10})$alkylamino, $(C_{1-10})$alkoxyamino, hydroxy $(C_{1-10})$alkoxyamino, hydroxy$(C_{1-10})$alkylamino, cycloamino, sulfonamido, imino, $(C_{2-10})$alkyl, halo $(C_{1-10})$alkyl, carbonyl$(C_{1-3})$alkyl, thiocarbonyl$(C_{1-3})$ alkyl, sulfonyl$(C_{1-3})$alkyl, sulfinyl$(C_{1-3})$alkyl, amino $(C_{1-10})$alkyl, imino$(C_{1-3})$alkyl, $(C_{3-12})$cycloalkyl$(C_{1-5})$ alkyl, hetero$(C_{3-12})$cycloalkyl$(C_{1-5})$alkyl, aryl$(C_{1-10})$ alkyl, heteroaryl$(C_{1-5})$alkyl, $(C_{9-12})$bicycloaryl$(C_{1-5})$ alkyl, hetero$(C_{8-12})$bicycloaryl$(C_{1-5})$alkyl, $(C_{3-12})$ cycloalkyl, hetero$(C_{3-12})$cycloalkyl, $(C_{9-12})$ bicycloalkyl, hetero$(C_{3-12})$bicycloalkyl, $(C_{4-12})$aryl, hetero$(C_{1-10})$aryl, $(C_{9-12})$bicycloaryl and hetero$(C_{4-12})$ bicycloaryl, each substituted or unsubstituted;

$R_4$ is selected from the group consisting of amino, $(C_{1-5})$ alkylamino, $(C_{1-5})$alkyl, halo$(C_{1-5})$alkyl, hydroxy$(C_{1-5})$ alkyl, $(C_{1-8})$azaalkyl, hydroxy$(C_{1-8})$azaalkyl and $(C_{3-6})$ cycloalkyl, each substituted or unsubstituted;

$R_5$ is selected from the group consisting of hydrogen, $(C_{1-5})$alkyl, amino $(C_{1-10})$alkyl, hydroxy$(C_{1-10})$alkyl and $(C_{3-12})$cycloalkyl, each substituted or unsubstituted; and $R_7$ is selected from the group consisting of hydrogen, halo, nitro, cyano, thio, oxy, hydroxy, carbonyloxy, $(C_{1-10})$ alkoxy, $(C_{4-12})$aryloxy, hetero$(C_{1-10})$aryloxy, carbonyl, oxycarbonyl, aminocarbonyl, amino, $(C_{1-10})$alkylamino, sulfonamido, imino, sulfonyl, sulfinyl, $(C_{1-10})$ alkyl, halo$(C_{1-10})$alkyl, hydroxy$(C_{1-10})$alkyl, carbonyl $(C_{1-10})$alkyl, thiocarbonyl$(C_{1-10})$alkyl, sulfonyl$(C_{1-10})$ alkyl, sulfinyl$(C_{1-10})$alkyl, $(C_{1-10})$azaalkyl, imino $(C_{1-10})$alkyl, $(C_{3-12})$cycloalkyl$(C_{1-5})$alkyl, hetero $(C_{3-12})$cycloalkyl$(C_{1-10})$alkyl, aryl$(C_{1-10})$alkyl, hetero $(C_{1-10})$aryl$(C_{1-5})$alkyl, $(C_{9-12})$bicycloaryl$(C_{1-5})$alkyl, hetero$(C_{8-12})$bicycloaryl$(C_{1-5})$alkyl, $(C_{3-12})$cycloalkyl, hetero$(C_{3-12})$cycloalkyl, $(C_{9-12})$bicycloalkyl, hetero $(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted.

2. A compound of claim 1 represented by the formula:

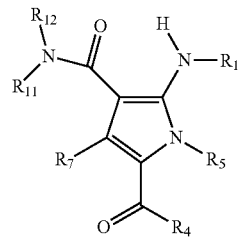

or an ester, tautomer, enantiomer, pharmaceutically acceptable salt or prodrug thereof,
wherein $R_{11}$ is hydrogen, a substituent convertible in vivo to hydrogen, a substituted or unsubstituted $(C_{1-10})$alkyl, or a substituted or unsubstituted halo$(C_{1-10})$alkyl; and $R_{12}$ is selected from the group consisting of hydrogen, oxy, hydroxy, alkoxy, aryloxy, heteroaryloxy, carbonyl, amino, $(C_{1-10})$alkylamino, sulfonamido, imino, sulfonyl, sulfinyl, $(C_{1-10})$alkyl, halo$(C_{1-10})$alkyl, carbonyl $(C_{1-3})$alkyl, thiocarbonyl$(C_{1-3})$alkyl, sulfonyl$(C_{1-3})$ alkyl, sulfinyl$(C_{1-3})$alkyl, amino $(C_{1-10})$alkyl, imino $(C_{1-3})$alkyl, $(C_{3-12})$cycloalkyl$(C_{1-5})$alkyl, hetero$(C_{3-12})$ cycloalkyl$(C_{1-5})$alkyl, aryl$(C_{1-10})$alkyl, heteroaryl $(C_{1-5})$alkyl, $(C_{9-12})$bicycloaryl$(C_{1-5})$alkyl, hetero $(C_{8-12})$bicycloaryl$(C_{1-5})$alkyl, $(C_{3-12})$cycloalkyl, hetero $(C_{3-12})$cycloalkyl, $(C_{9-12})$bicycloalkyl, hetero $(C_{3-12})$bicycloalkyl, $(C_{4-12})$aryl, hetero$(C_{1-10})$aryl, $(C_{9-12})$bicycloaryl and hetero$(C_{4-12})$bicycloaryl, each substituted or unsubstituted, or $R_{11}$ and $R_{12}$ are taken together to form a substituted or unsubstituted ring.

3. A compound of claim 1 represented by the formula:

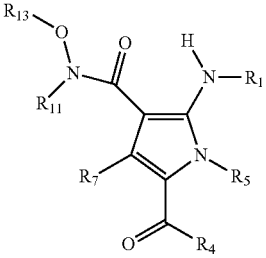

or an ester, tautomer, enantiomer, pharmaceutically acceptable salt or prodrug thereof,
wherein $R_{11}$ is hydrogen, a substituent convertible in vivo to hydrogen, a substituted or unsubstituted $(C_{1-10})$alkyl, or a substituted or unsubstituted halo$(C_{1-10})$alkyl; and $R_{13}$ is selected from the group consisting of hydrogen, $(C_{1-10})$alkyl, halo$(C_{1-10})$alkyl, carbonyl$(C_{1-3})$alkyl, thiocarbonyl$(C_{1-3})$alkyl, sulfonyl$(C_{1-3})$alkyl, sulfinyl $(C_{1-3})$alkyl, amino $(C_{1-10})$alkyl, imino$(C_{1-3})$alkyl, ($C_{3-12}$) cycloalkyl($C_{1-5}$)alkyl, hetero($C_{3-12}$)cycloalkyl ($C_{1-5}$)alkyl, aryl($C_{1-10}$)alkyl, heteroaryl($C_{1-5}$)alkyl, ($C_{9-12}$)bicycloaryl($C_{1-5}$)alkyl, hetero($C_{8-12}$)bicycloaryl ($C_{1-5}$)alkyl, ($C_{3-12}$)cycloalkyl, hetero($C_{3-12}$)cycloalkyl, ($C_{9-12}$)bicycloalkyl, hetero($C_{3-12}$)bicycloalkyl, ($C_{4-12}$) aryl, hetero($C_{1-10}$)aryl, ($C_{9-12}$)bicycloaryl and hetero ($C_{4-12}$)bicycloaryl, each substituted or unsubstituted, or $R_{13}$ and $R_{11}$ are taken together to form a substituted or unsubstituted ring.

4. The compound according to any of claims 1, 2, or 3, wherein $R_1$ is selected from the group consisting of ($C_{4-12}$) aryl and hetero($C_{1-10}$)aryl, each substituted or unsubstituted.

5. The compound according to any of claims 1, 2, or 3, wherein $R_1$ is a substituted or unsubstituted ($C_{4-12}$)aryl.

6. The compound according to any of claims 1, 2, or 3, wherein $R_1$ is a substituted or unsubstituted phenyl.

7. The compound according to claim 5, wherein $R^5$ is a substituted or unsubstituted ($C_{1-5}$)alkyl.

8. The compound according to claim 5, wherein $R_5$ is hydrogen.

9. The compound according to claim 5, wherein $R_5$ is methyl.

10. The compound according to claim 5, wherein $R_7$ is hydrogen.

11. The compound according to claim 5, wherein $R_7$ is a substituted or unsubstituted ($C_{1-3}$)alkyl.

12. The compound according to claim 5, wherein $R_7$ is halo.

13. The compound according to claim 2, wherein $R_{11}$ is hydrogen.

14. The compound according to claim 2, wherein $R_{11}$ is selected from the group consisting of ($C_{1-5}$)alkyl and halo ($C_{1-5}$)alkyl, each substituted or unsubstituted.

15. The compound according to claim 2, wherein $R_{12}$ is selected from the group consisting of hydrogen, hydroxyl, alkoxy, ($C_{1-10}$)alkyl, hydroxy($C_{1-10}$)alkyl, ($C_{3-12}$)cycloalkyl, hetero($C_{3-12}$)cycloalkyl and hetero($C_{1-10}$)aryl, each substituted or unsubstituted.

16. The compound according to claim 3, wherein $R_{13}$ is selected from the group consisting of hydrogen, alkoxy, ($C_{1-10}$)alkyl, hydroxy($C_{1-10}$)alkyl and hetero($C_{3-12}$)cycloalkyl($C_{1-10}$)alkyl, each substituted or unsubstituted.

17. The compound according to claim 1 selected from the group consisting of:
- 5-Acetyl-2-(2-fluoro-4-iodo-phenylamino)-1H-pyrrole-3-carboxylic acid;
- 5-Acetyl-2-(2-fluoro-4-iodophenylamino)-N-(2-hydroxyethoxy)-1H-pyrrole-3-carboxamide;
- 5-Acetyl-2-(2-fluoro-4-iodophenylamino)-1-methyl-1H-pyrrole-3-carboxylic acid;
- 5-Acetyl-2-(2-fluoro-4-iodophenylamino)-N-(2-hydroxyethoxy)-1-methyl-1H-pyrrole-3-carboxamide;
- 5-Acetyl-2-(2-fluoro-4-iodophenylamino)-N-(3-hydroxypropoxy)-1-methyl-1H-pyrrole-3-carboxamide;
- (R)-5-Acetyl-N-(2,3-dihydroxypropoxy)-2-(2-fluoro-4-iodophenylamino)-1-methyl-1H-pyrrole-3-carboxamide;
- (S)-5-Acetyl-N-(2,3-dihydroxypropoxy)-2-(2-fluoro-4-iodophenylamino)-1-methyl-1H-pyrrole-3-carboxamide;
- 5-Acetyl-2-(2-fluoro-4-iodophenylamino)-N-(3-hydroxy-2-(hydroxymethyl)propoxy)-1-methyl-1H-pyrrole-3-carboxamide;
- 5-Acetyl-4-chloro-2-(2-fluoro-4-iodophenylamino)-1-methyl-1H-pyrrole-3-carboxylic acid;
- (R)-5-Acetyl-4-chloro-N-(2,3-dihydroxypropoxy)-2-(2-fluoro-4-iodophenylamino)-1-methyl-1H-pyrrole-3-carboxamide;
- (S)-5-Acetyl-4-chloro-N-(2,3-dihydroxypropoxy)-2-(2-fluoro-4-iodophenylamino)-1-methyl-1H-pyrrole-3-carboxamide;
- 5-Acetyl-4-chloro-2-(2-fluoro-4-iodophenylamino)-N-(2-hydroxyethoxy)-1-methyl-1H-pyrrole-3-carboxamide;
- 5-Acetyl-2-(2-fluoro-4-iodophenylamino)-1-methyl-1H-pyrrole-3-carboxamide;
- 5-Acetyl-N-(1,3-dihydroxypropan-2-yloxy)-2-(2-fluoro-4-iodophenylamino)-1-methyl-1H-pyrrole-3-carboxamide;
- 5-Acetyl-N-(2,3-dihydroxypropyl)-2-(2-fluoro-4-iodophenylamino)-1-methyl-1H-pyrrole-3-carboxamide;
- 5-Acetyl-2-(2-fluoro-4-iodophenylamino)-N-(3-hydroxypropyl)-1-methyl-1H-pyrrole-3-carboxamide;
- 5-Acetyl-2-(2-fluoro-4-iodophenylamino)-N-methoxy-N,1-dimethyl-1H-pyrrole-3-carboxamide;
- 1-(5-(2-Fluoro-4-iodophenylamino)-4-(4-hydroxyisoxazolidine-2-carbonyl)-1-methyl-1H-pyrrol-2-yl)ethanone;
- (R)-5-Acetyl-N-(2,4-dihydroxybutoxy)-2-(2-fluoro-4-iodophenylamino)-1-methyl-1H-pyrrole-3-carboxamide;
- (S)-5-Acetyl-N-(2,4-dihydroxybutoxy)-2-(2-fluoro-4-iodophenylamino)-1-methyl-1H-pyrrole-3-carboxamide;
- 1-(4-(Azetidine-1-carbonyl)-5-(2-fluoro-4-iodophenylamino)-1-methyl-1H-pyrrol-2-yl)ethanone;
- 1-(4-(3-Aminoazetidine-1-carbonyl)-5-(2-fluoro-4-iodophenylamino)-1-methyl-1H-pyrrol-2-yl)ethanone;
- (S)-1-(5-(2-Fluoro-4-iodophenylamino)-4-(3-(hydroxymethyl)pyrrolidine-1-carbonyl)-1-methyl-1H-pyrrol-2-yl)ethanone;
- 1-(5-(2-Fluoro-4-iodophenylamino)-4-(2-(hydroxymethyl)azetidine-1-carbonyl)-1-methyl-1H-pyrrol-2-yl)ethanone;
- (R)-1-(5-(2-Fluoro-4-iodophenylamino)-4-(3-(hydroxymethyl)pyrrolidine-1-carbonyl)-1-methyl-1H-pyrrol-2-yl)ethanone;
- 1-(4-((2R,3S,4S)-3,4-Dihydroxy-2-(hydroxymethyl)pyrrolidine-1-carbonyl)-5-(2-fluoro-4-iodophenylamino)-1-methyl-1H-pyrrol-2-yl)ethanone;
- 1-[5-(2-Fluoro-4-iodo-phenylamino)-4-(3-hydroxy-azetidine-1-carbonyl)-1-methyl-1H-pyrrol-2-yl]-ethanone;
- 1-[5-(2-Fluoro-4-iodo-phenylamino)-4-((R)-3-hydroxy-pyrrolidine-1-carbonyl)-1-methyl-1H-pyrrol-2-yl]-ethanone;
- 1-[5-(2-Fluoro-4-iodo-phenylamino)-4-((S)-3-hydroxy-pyrrolidine-1-carbonyl)-1-methyl-1H-pyrrol-2-yl]-ethanone;
- 1-[5-(2-Fluoro-4-iodo-phenylamino)-1-methyl-4-(pyrrolidine-1-carbonyl)-1H-pyrrol-2-yl]-ethanone;
- 1-[5-(2-Fluoro-4-iodo-phenylamino)-4-((S)-2-hydroxymethyl-pyrrolidine-1-carbonyl)-1-methyl-1H-pyrrol-2-yl]-ethanone;
- 1-[5-(2-Fluoro-4-iodo-phenylamino)-4-((R)-2-hydroxymethyl-pyrrolidine-1-carbonyl)-1-methyl-1H-pyrrol-2-yl]-ethanone;
- 1-[4-(3-(R)-Amino-pyrrolidine-1-carbonyl)-5-(2-fluoro-4-iodo-phenylamino)-1-methyl-1H-pyrrol-2-yl]-ethanone;
- 1-{5-(2-Fluoro-4-iodo-phenylamino)-4-[3-(2-hydroxyethylamino)-azetidine-1-carbonyl]-1-methyl-1H-pyrrol-2-yl}-ethanone;
- 1-(5-(2-Fluoro-4-iodo-phenylamino)-4-{3-[(2-hydroxyethyl)-methyl-amino]-azetidine-1-carbonyl}-1-methyl-1H-pyrrol-2-yl)-ethanone;

1-[4-(3-Dimethylamino-azetidine-1-carbonyl)-5-(2-fluoro-4-iodo-phenylamino) -1-methyl-1H-pyrrol-2-yl]-ethanone;
1-[5-(2-Fluoro-4-iodo-phenylamino)-4-(3-hydroxy-3-hydroxymethyl-azetidine-1-carbonyl)-1-methyl-1H-pyrrol-2-yl]-ethanone;
Ethyl 5-acetyl-4-fluoro-2-(2-fluoro-4-iodophenylamino)-1-methyl-1H-pyrrole-3-carboxylate;
5-Acetyl-4-fluoro-2-(2-fluoro-4-iodophenylamino)-1-methyl-1H-pyrrole-3-carboxylic acid;
(R)-5-Acetyl-N-(2,3-dihydroxypropoxy)-4-fluoro-2-(2-fluoro-4-iodophenylamino)-1-methyl-1H-pyrrole-3-carboxamide;
(S)-5-acetyl-N-(2,3-dihydroxypropoxy)-4-fluoro-2-(2-fluoro-4-iodophenylamino)-1-methyl-1H-pyrrole-3-carboxamide;
5-Acetyl-2-(4-bromo-2-fluorophenylamino)-N-(2-hydroxyethoxy)-1-methyl-1H -pyrrole-3-carboxamide;
2-(2-fluoro-4-iodophenylamino)-N-(2-hydroxyethoxy)-1-methyl-5-propionyl-1H -pyrrole-3-carboxamide;
2-(2-fluoro-4-iodophenylamino)-5-(2-fluoroacetyl)-N-(2-hydroxyethoxy)-1-methyl-1H-pyrrole-3-carboxamide;
5-(2,2-difluoroacetyl)-2-(2-fluoro-4-iodophenylamino)-N-(2-hydroxyethoxy)-1-methyl-1H-pyrrole-3-carboxamide;
2-(2-fluoro-4-iodophenylamino)-N-(2-hydroxyethoxy)-1-methyl-5-(2,2,2-trifluoroacetyl)-1H-pyrrole-3-carboxamide;
5-(2-fluoro-4-iodophenylamino)-N4-(2-hydroxyethoxy)-1-methyl-1H-pyrrole -2,4-dicarboxamide;
5-(2-fluoro-4-iodophenylamino)-N4-(2-hydroxyethoxy)-N2, 1-dimethyl-1H -pyrrole-2,4-dicarboxamide;
5-(cyclopropanecarbonyl)-2-(2-fluoro-4-iodophenylamino)-N-(2-hydroxyethoxy) -1-methyl-1H-pyrrole-3-carboxamide;
5-acetyl-2-(2-fluoro-4-iodophenylamino)-N-(2-hydroxyethoxy)-1,4-dimethyl-1H -pyrrole-3-carboxamide;
5-acetyl-4-fluoro-2-(2-fluoro-4-iodophenylamino)-N-(2-hydroxyethoxy)-1-methyl-1H-pyrrole-3-carboxamide;
1-(5-acetyl-2-(2-fluoro-4-iodophenylamino)-1-methyl-1H-pyrrol-3-yl)-2-hydroxyethanone;
2-(2-fluoro-4-iodophenylamino)-5-(2-hydroxyacetyl)-N-(2-hydroxyethoxy)-1-methyl-1H-pyrrole-3-carboxamide;
2-(2-fluoro-4-iodophenylamino)-N-(2-hydroxyethoxy)-5-(3-hydroxypropanoyl) -1-methyl-1H-pyrrole-3-carboxamide;
2-(2-fluoro-4-iodophenylamino)-N-(2-hydroxyethoxy)-1-methyl-5-(2-(methylamino)acetyl)-1H-pyrrole-3-carboxamide;
5-(2-(dimethylamino)acetyl)-2-(2-fluoro-4-iodophenylamino)-N-(2-hydroxyethoxy)-1-methyl-1H-pyrrole-3-carboxamide;
2-(2-fluoro-4-iodophenylamino)-N-(2-hydroxyethoxy)-5-(2-(2-hydroxyethylamino)acetyl)-1-methyl-1H-pyrrole-3-carboxamide;
5-acetyl-2-(2-chloro-4-iodophenylamino)-N-(2-hydroxyethoxy)-1-methyl-1H -pyrrole-3-carboxamide;
5-acetyl-N-(2-hydroxyethoxy)-2-(4-iodo-2-methylphenylamino)-1-methyl-1H -pyrrole-3-carboxamide;
5-acetyl-2-(4-bromo-2-chlorophenylamino)-N-(2-hydroxyethoxy)-1-methyl-1H -pyrrole-3-carboxamide;
5-acetyl-2-(2-fluoro-4-iodophenylamino)-N-hydroxy-1-methyl-1H-pyrrole-3-carboxamide;
5-acetyl-N-(2-(dimethylamino)ethoxy)-2-(2-fluoro-4-iodophenylamino)-1-methyl-1H-pyrrole-3-carboxamide;
5-acetyl-N-(cyclopropylmethoxy)-2-(2-fluoro-4-iodophenylamino)-1-methyl-1H -pyrrole-3-carboxamide;
1-(5-(2-fluoro-4-iodophenylamino)-1-methyl-4-(5-methyl-4H-1,2,4-triazol-3-yl) -1H-pyrrol-2-yl)ethanone;
1-(5-(2-fluoro-4-iodophenylamino)-1-methyl-4-(5-methyl-1,3,4-oxadiazol-2-yl) -1H-pyrrol-2-yl)ethanone;
5-acetyl-2-(2-fluoro-4-iodophenylamino)-1-methyl-N-(1,2,4-oxadiazol-5-yl)-1H -pyrrole-3-carboxamide;
5-acetyl-2-(2-fluoro-4-iodophenylamino)-1-methyl-N-(1,3,4-oxadiazol-2-yl)-1H -pyrrole-3-carboxamide;
5-acetyl-2-(2-fluoro-4-iodophenylamino)-1-methyl-N-(oxazol-2-yl)-1H-pyrrole -3-carboxamide; and
5-acetyl-2-(2-fluoro-4-iodophenylamino)-N-(2-hydroxyethyl)-1-methyl-1H -pyrrole-3-carboxamide.

18. The compound according to claim 1 selected from the group consisting of:
5-Acetyl-2-(2-fluoro-4-iodophenylamino)-N-(2-hydroxyethoxy)-1-methyl-1H -pyrrole-3-carboxamide;
(R)-5-Acetyl-N-(2,3-dihydroxypropoxy)-2-(2-fluoro-4-iodophenylamino)-1-methyl-1H-pyrrole-3-carboxamide;
(S)-5-Acetyl-N-(2,3-dihydroxypropoxy)-2-(2-fluoro-4-iodophenylamino)-1-methyl-1H-pyrrole-3-carboxamide;
(R)-5-Acetyl-4-chloro-N-(2,3-dihydroxypropoxy)-2-(2-fluoro-4-iodophenylamino)-1-methyl-1H-pyrrole-3-carboxamide;
(S)-5-Acetyl-4-chloro-N-(2,3-dihydroxypropoxy)-2-(2-fluoro-4-iodophenylamino)-1-methyl-1H-pyrrole-3-carboxamide;
5-Acetyl-N-(1,3-dihydroxypropan-2-yloxy)-2-(2-fluoro-4-iodophenylamino)-1-methyl-1H-pyrrole-3-carboxamide;
(R)-5-Acetyl-N-(2,3-dihydroxypropoxy)-4-fluoro-2-(2-fluoro-4-iodophenylamino)-1-methyl-1H-pyrrole-3-carboxamide; and
(S)-5-acetyl-N-(2,3-dihydroxypropoxy)-4-fluoro-2-(2-fluoro-4-iodophenylamino)-1-methyl-1H-pyrrole-3-carboxamide.

19. The compound according to claim 1, wherein the compound is in the form of a pharmaceutically acceptable salt.

20. The compound according to claim 1, wherein the compound is present in a mixture of stereoisomers.

21. The compound according to claim 1, wherein the compound is a single stereoisomer.

22. A pharmaceutical composition comprising as an active ingredient a compound according to claim 1 and a pharmaceutical excipient.

23. The pharmaceutical composition according to claim 22, wherein the composition is a solid formulation adapted for oral administration.

24. The pharmaceutical composition according to claim 22, wherein the composition is a liquid formulation adapted for oral administration.

25. The pharmaceutical composition according to claim 22, wherein the composition is a tablet.

26. The pharmaceutical composition according to claim 22, wherein the composition is a liquid formulation adapted for parenteral administration.

27. A pharmaceutical composition comprising a compound according to claim 1, wherein the composition is adapted for administration by a route selected from the group consisting of orally, parenterally, intraperitoneally, intravenously, intraarterially, transdermally, sublingually, intramuscularly, rectally, transbuccally, intranasally, liposomally, via inhalation, vaginally, intraoccularly, via local delivery, subcutaneously, intraadiposally, intraarticularly, and intrathecally.

28. A method of inhibiting a Mitogen-Activated Protein Kinase (MEK) comprising contacting the MEK with a compound according to claim 1.

29. A method of inhibiting Mitogen-Activated Protein Kinase (MEK) comprising causing a compound according to claim 1 to be present in a subject in order to inhibit the MEK in vivo.

30. A method of inhibiting Mitogen-Activated Protein Kinase (MEK) comprising administering a prodrug of a compound according to claim 1 to a subject.

* * * * *

SEQUENCE LISTING

```
<160> NUMBER OF SEQ ID NOS: 6

<210> SEQ ID NO 1
<211> LENGTH: 400
<212> TYPE: PRT
<213> ORGANISM: Artificial
<220> FEATURE:
<223> OTHER INFORMATION: Residues 2-393 of human MEK1 with deletion from
      residues 32-51, mutations S218E and S222D, and an N-terminal
      6-histidine tag.
<220> FEATURE:
<221> NAME/KEY: MISC_FEATURE
<222> LOCATION: (1)..(28)
<223> OTHER INFORMATION: N-terminal 6-histidine tag
<220> FEATURE:
<221> NAME/KEY: MISC_FEATURE
<222> LOCATION: (29)..(400)
<223> OTHER INFORMATION: Residues 2-393 of human MEK1 with deletion from
      residues 32-51, and mutations S218E and S222D

<400> SEQUENCE: 1

Met Ser Tyr Tyr His His His His His His Asp Tyr Asp Ile Pro Thr
1               5                   10                  15

Thr Glu Asn Leu Tyr Phe Gln Gly Ala Met Gly Ser Pro Lys Lys Lys
            20                  25                  30
```

Pro Thr Pro Ile Gln Leu Asn Pro Ala Pro Asp Gly Ser Ala Val Asn
            35                  40                  45

Gly Thr Ser Ser Ala Glu Thr Asn Leu Glu Ala Phe Leu Thr Gln Lys
 50                  55                  60

Gln Lys Val Gly Glu Leu Lys Asp Asp Asp Phe Glu Lys Ile Ser Glu
 65                  70                  75                  80

Leu Gly Ala Gly Asn Gly Gly Val Val Phe Lys Val Ser His Lys Pro
                 85                  90                  95

Ser Gly Leu Val Met Ala Arg Lys Leu Ile His Leu Glu Ile Lys Pro
                100                 105                 110

Ala Ile Arg Asn Gln Ile Ile Arg Glu Leu Gln Val Leu His Glu Cys
            115                 120                 125

Asn Ser Pro Tyr Ile Val Gly Phe Tyr Gly Ala Phe Tyr Ser Asp Gly
        130                 135                 140

Glu Ile Ser Ile Cys Met Glu His Met Asp Gly Gly Ser Leu Asp Gln
145                 150                 155                 160

Val Leu Lys Lys Ala Gly Arg Ile Pro Glu Gln Ile Leu Gly Lys Val
                165                 170                 175

Ser Ile Ala Val Ile Lys Gly Leu Thr Tyr Leu Arg Glu Lys His Lys
                180                 185                 190

Ile Met His Arg Asp Val Lys Pro Ser Asn Ile Leu Val Asn Ser Arg
            195                 200                 205

Gly Glu Ile Lys Leu Cys Asp Phe Gly Val Ser Gly Gln Leu Ile Asp
        210                 215                 220

Glu Met Ala Asn Asp Phe Val Gly Thr Arg Ser Tyr Met Ser Pro Glu
225                 230                 235                 240

Arg Leu Gln Gly Thr His Tyr Ser Val Gln Ser Asp Ile Trp Ser Met
                245                 250                 255

Gly Leu Ser Leu Val Glu Met Ala Val Gly Arg Tyr Pro Ile Pro Pro
                260                 265                 270

Pro Asp Ala Lys Glu Leu Glu Leu Met Phe Gly Cys Gln Val Glu Gly
            275                 280                 285

Asp Ala Ala Glu Thr Pro Pro Arg Pro Arg Thr Pro Gly Arg Pro Leu
        290                 295                 300

Ser Ser Tyr Gly Met Asp Ser Arg Pro Pro Met Ala Ile Phe Glu Leu
305                 310                 315                 320

Leu Asp Tyr Ile Val Asn Glu Pro Pro Pro Lys Leu Pro Ser Gly Val
                325                 330                 335

Phe Ser Leu Glu Phe Gln Asp Phe Val Asn Lys Cys Leu Ile Lys Asn
            340                 345                 350

Pro Ala Glu Arg Ala Asp Leu Lys Gln Leu Met Val His Ala Phe Ile
        355                 360                 365

Lys Arg Ser Asp Ala Glu Glu Val Asp Phe Ala Gly Trp Leu Cys Ser
370                 375                 380

Thr Ile Gly Leu Asn Gln Pro Ser Thr Pro Thr His Ala Ala Gly Val
385                 390                 395                 400

<210> SEQ ID NO 2
<211> LENGTH: 1203
<212> TYPE: DNA
<213> ORGANISM: Artificial
<220> FEATURE:
<223> OTHER INFORMATION: DNA sequence encoding SEQ ID NO: 1.

<400> SEQUENCE: 2

-continued

| | |
|---|---|
| atgtcgtact accatcacca tcaccatcac gattacgata tcccaacgac cgaaaacctg | 60 |
| tattttcagg gcgccatggg atcccccaag aagaagccga cgcccatcca gctgaacccg | 120 |
| gcccccgacg gctctgcagt taacgggacc agctctgcgg agaccaactt ggaggccttt | 180 |
| cttacccaga agcagaaggt gggagaactg aaggatgacg actttgagaa gatcagtgag | 240 |
| ctgggggctg gcaatggcgg tgtggtgttc aaggtctccc acaagccttc tggcctggtc | 300 |
| atggccagaa agctaattca tctggagatc aaacccgcaa tccggaacca gatcataagg | 360 |
| gagctgcagg ttctgcatga gtgcaactct ccgtacatcg tgggcttcta tggtgcgttc | 420 |
| tacagcgatg gcgagatcag tatctgcatg gagcacatgg atggaggttc tctggatcaa | 480 |
| gtcctgaaga aagctggaag aattcctgaa caaattttag aaaagttag cattgctgta | 540 |
| ataaaaggcc tgacatatct gagggagaag cacaagatca tgcacagaga tgtcaagccc | 600 |
| tccaacatcc tagtcaactc ccgtggggag atcaagctct gtgactttgg ggtcagcggg | 660 |
| cagctcatcg acgaaatggc caacgacttc gtgggcacaa ggtcctacat gtcgccagaa | 720 |
| agactccagg ggactcatta ctctgtgcag tcagacatct ggagcatggg actgtctctg | 780 |
| gtagagatgg cggttgggag gtatcccatc cctcctccag atgccaagga gctggagctg | 840 |
| atgtttgggt gccaggtgga aggagatgcg gctgagaccc acccaggcc aaggaccccc | 900 |
| gggaggcccc ttagctcata cggaatggac agccgacctc ccatggcaat ttttgagttg | 960 |
| ttggattaca tagtcaacga gcctcctcca aaactgccca gtggagtgtt cagtctggaa | 1020 |
| tttcaagatt ttgtgaataa atgcttaata aaaaaccccg cagagagagc agatttgaag | 1080 |
| caactcatgg ttcatgcttt tatcaagaga tctgatgctg aggaagtgga ttttgcaggt | 1140 |
| tggctctgct ccaccatcgg ccttaaccag cccagcacac caacccatgc tgctggcgtc | 1200 |
| taa | 1203 |

<210> SEQ ID NO 3
<211> LENGTH: 428
<212> TYPE: PRT
<213> ORGANISM: Artificial
<220> FEATURE:
<223> OTHER INFORMATION: Residues 1-400 of human MEK2 with mutations
      S222E and S226D, and an N-terminal 6-histidine tag.
<220> FEATURE:
<221> NAME/KEY: MISC_FEATURE
<222> LOCATION: (1)..(28)
<223> OTHER INFORMATION: N-terminal 6-histidine tag
<220> FEATURE:
<221> NAME/KEY: MISC_FEATURE
<222> LOCATION: (29)..(428)
<223> OTHER INFORMATION: Residues 1-400 of human MEK2 with mutations
      S222E and S226D

<400> SEQUENCE: 3

Met Ser Tyr Tyr His His His His His His Asp Tyr Asp Ile Pro Thr
1               5                   10                  15

Thr Glu Asn Leu Tyr Phe Gln Gly Ala Met Glu Pro Met Leu Ala Arg
            20                  25                  30

Arg Lys Pro Val Leu Pro Ala Leu Thr Ile Asn Pro Thr Ile Ala Glu
        35                  40                  45

Gly Pro Ser Pro Thr Ser Glu Gly Ala Ser Glu Ala Asn Leu Val Asp
    50                  55                  60

Leu Gln Lys Lys Leu Glu Gly Leu Glu Leu Asp Glu Gln Gln Lys Lys
65                  70                  75                  80

Arg Leu Glu Ala Phe Leu Thr Gln Lys Ala Lys Val Gly Glu Leu Lys
                85                  90                  95

Asp Asp Asp Phe Glu Arg Ile Ser Glu Leu Gly Ala Gly Asn Gly Gly
            100                 105                 110

Val Val Thr Lys Val Gln His Arg Pro Ser Gly Leu Ile Met Ala Arg
        115                 120                 125

Lys Leu Ile His Leu Glu Ile Lys Pro Ala Ile Arg Asn Gln Ile Ile
    130                 135                 140

Arg Glu Leu Gln Val Leu His Glu Cys Asn Ser Pro Tyr Ile Val Gly
145                 150                 155                 160

Phe Tyr Gly Ala Phe Tyr Ser Asp Gly Glu Ile Ser Ile Cys Met Glu
                165                 170                 175

His Met Asp Gly Gly Ser Leu Asp Gln Val Leu Lys Glu Ala Lys Arg
            180                 185                 190

Ile Pro Glu Glu Ile Leu Gly Lys Val Ser Ile Ala Val Leu Arg Gly
        195                 200                 205

Leu Ala Tyr Leu Arg Glu Lys His Gln Ile Met His Arg Asp Val Lys
    210                 215                 220

Pro Ser Asn Ile Leu Val Asn Ser Arg Gly Glu Ile Lys Leu Cys Asp
225                 230                 235                 240

Phe Gly Val Ser Gly Gln Leu Ile Asp Glu Met Ala Asn Asp Phe Val
                245                 250                 255

Gly Thr Arg Ser Tyr Met Ala Pro Glu Arg Leu Gln Gly Thr His Tyr
            260                 265                 270

Ser Val Gln Ser Asp Ile Trp Ser Met Gly Leu Ser Leu Val Glu Leu
        275                 280                 285

Ala Val Gly Arg Tyr Pro Ile Pro Pro Asp Ala Lys Glu Leu Glu
    290                 295                 300

Ala Ile Phe Gly Arg Pro Val Val Asp Gly Glu Gly Glu Pro His
305                 310                 315                 320

Ser Ile Ser Pro Arg Pro Arg Pro Gly Arg Pro Val Ser Gly His
                325                 330                 335

Gly Met Asp Ser Arg Pro Ala Met Ala Ile Phe Glu Leu Leu Asp Tyr
            340                 345                 350

Ile Val Asn Glu Pro Pro Pro Lys Leu Pro Asn Gly Val Phe Thr Pro
        355                 360                 365

Asp Phe Gln Glu Phe Val Asn Lys Cys Leu Ile Lys Asn Pro Ala Glu
    370                 375                 380

Arg Ala Asp Leu Lys Met Leu Thr Asn His Thr Phe Ile Lys Arg Ser
385                 390                 395                 400

Glu Val Glu Glu Val Asp Phe Ala Gly Trp Leu Cys Lys Thr Leu Arg
                405                 410                 415

Leu Asn Gln Pro Gly Thr Pro Thr Arg Thr Ala Val
            420                 425

<210> SEQ ID NO 4
<211> LENGTH: 1287
<212> TYPE: DNA
<213> ORGANISM: Artificial
<220> FEATURE:
<223> OTHER INFORMATION: DNA sequence encoding SEQ. I.D. No. 3.

<400> SEQUENCE: 4
atgtcgtact accatcacca tcaccatcac gattacgata tcccaacgac cgaaaacctg      60
tattttcagg gcgccatgga acccatgctg gcccggagga agccggtgct gccggcgctc     120
accatcaacc ctaccatcgc cgagggccca tcccctacca gcgagggcgc ctccgaggca     180
aacctggtgg acctgcagaa gaagctggag gagctggaac ttgacgagca gcagaagaag     240

-continued

```
cggctggaag cctttctcac ccagaaagcc aaggtcggcg aactcaaaga cgatgacttc    300
gaaaggatct cagagctggg cgcgggcaac ggcggggtgg tcaccaaagt ccagcacaga    360
ccctcgggcc tcatcatggc caggaagctg atccaccttg agatcaagcc ggccatccgg    420
aaccagatca tccgcgagct gcaggtcctg cacgaatgca actcgccgta catcgtgggc    480
ttctacgggg ccttctacag tgacggggag atcagcattt gcatggaaca catggacggc    540
ggctccctgg accaggtgct gaaagaggcc aagaggattc cgaggagat cctgggaaa     600 gtcagcatcg cggttctccg gggcttggcg tacctccgag agaagcacca gatcatgcac    660
cgagatgtga agccctccaa catcctcgtg aactctagag gggagatcaa gctgtgtgac    720 ttcgggg tga gcggccagct catagacgaa atggccaacg acttcgtggg cacgcgctcc    780
tacatggctc cggagcggtt gcagggcaca cattactcgg tgcagtcgga catctggagc    840
atgggcctgt ccctggtgga gctggccgtc ggaaggtacc ccatcccccc gcccgacgcc    900
aaagagctgg aggccatctt tggccggcc gtggtcgacg gggaagaagg agagcctcac    960
agcatctcgc ctcggccgag gcccccggg cgccccgtca gcggtcacgg gatggatagc   1020
cggcctgcca tggccatctt tgaactcctg gactatattg tgaacgagcc acctcctaag   1080
ctgcccaacg gtgtgttcac ccccgacttc caggagtttg tcaataaatg cctcatcaag   1140
aacccagcgg agcgggcgga cctgaagatg ctcacaaacc acaccttcat caagcggtcc   1200
gaggtggaag aagtggattt tgccggctgg ttgtgtaaaa ccctgcggct gaaccagccc   1260
ggcacaccca cgcgcaccgc cgtgtaa                                      1287
```

<210> SEQ ID NO 5
<211> LENGTH: 614
<212> TYPE: PRT
<213> ORGANISM: Artificial
<220> FEATURE:
<223> OTHER INFORMATION: Residues 1-379 of human ERK1 with an N-terminal
      GST tag.
<220> FEATURE:
<221> NAME/KEY: MISC_FEATURE
<222> LOCATION: (1)..(235)
<223> OTHER INFORMATION: N-terminal GST tag
<220> FEATURE:
<221> NAME/KEY: MISC_FEATURE
<222> LOCATION: (236)..(614)
<223> OTHER INFORMATION: Residues 1-379 of human ERK1

<400> SEQUENCE: 5

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125
```

-continued

```
Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Leu Glu Val Leu
    210                 215                 220

Phe Gln Gly Pro Leu Gly Ser Pro Asn Ser Gly Met Ala Ala Ala
225                 230                 235                 240

Ala Gln Gly Gly Gly Gly Glu Pro Arg Arg Thr Glu Gly Val Gly
                245                 250                 255

Pro Gly Val Pro Gly Glu Val Glu Met Val Lys Gly Gln Pro Phe Asp
            260                 265                 270

Val Gly Pro Arg Tyr Thr Gln Leu Gln Tyr Ile Gly Glu Gly Ala Tyr
        275                 280                 285

Gly Met Val Ser Ser Ala Tyr Asp His Val Arg Lys Thr Arg Val Ala
    290                 295                 300

Ile Lys Lys Ile Ser Pro Phe Glu His Gln Thr Tyr Cys Gln Arg Thr
305                 310                 315                 320

Leu Arg Glu Ile Gln Ile Leu Leu Arg Phe Arg His Glu Asn Val Ile
                325                 330                 335

Gly Ile Arg Asp Ile Leu Arg Ala Ser Thr Leu Glu Ala Met Arg Asp
            340                 345                 350

Val Tyr Ile Val Gln Asp Leu Met Glu Thr Asp Leu Tyr Lys Leu Leu
        355                 360                 365

Lys Ser Gln Gln Leu Ser Asn Asp His Ile Cys Tyr Phe Leu Tyr Gln
    370                 375                 380

Ile Leu Arg Gly Leu Lys Tyr Ile His Ser Ala Asn Val Leu His Arg
385                 390                 395                 400

Asp Leu Lys Pro Ser Asn Leu Leu Ile Asn Thr Thr Cys Asp Leu Lys
                405                 410                 415

Ile Cys Asp Phe Gly Leu Ala Arg Ile Ala Asp Pro Glu His Asp His
            420                 425                 430

Thr Gly Phe Leu Thr Glu Tyr Val Ala Thr Arg Trp Tyr Arg Ala Pro
        435                 440                 445

Glu Ile Met Leu Asn Ser Lys Gly Tyr Thr Lys Ser Ile Asp Ile Trp
    450                 455                 460

Ser Val Gly Cys Ile Leu Ala Glu Met Leu Ser Asn Arg Pro Ile Phe
465                 470                 475                 480

Pro Gly Lys His Tyr Leu Asp Gln Leu Asn His Ile Leu Gly Ile Leu
                485                 490                 495

Gly Ser Pro Ser Gln Glu Asp Leu Asn Cys Ile Ile Asn Met Lys Ala
            500                 505                 510

Arg Asn Tyr Leu Gln Ser Leu Pro Ser Lys Thr Lys Val Ala Trp Ala
        515                 520                 525

Lys Leu Phe Pro Lys Ser Asp Ser Lys Ala Leu Asp Leu Leu Asp Arg
    530                 535                 540

Met Leu Thr Phe Asn Pro Asn Lys Arg Ile Thr Val Glu Glu Ala Leu
545                 550                 555                 560
```

```
Ala His Pro Tyr Leu Glu Gln Tyr Tyr Asp Pro Thr Asp Glu Pro Val
            565                 570                 575

Ala Glu Glu Pro Phe Thr Phe Ala Met Glu Leu Asp Asp Leu Pro Lys
        580                 585                 590

Glu Arg Leu Lys Glu Leu Ile Phe Gln Glu Thr Ala Arg Phe Gln Pro
        595                 600                 605

Gly Val Leu Glu Ala Pro
    610

<210> SEQ ID NO 6
<211> LENGTH: 1845
<212> TYPE: DNA
<213> ORGANISM: Artificial
<220> FEATURE:
<223> OTHER INFORMATION: DNA sequence encoding SEQ ID NO: 5.

<400> SEQUENCE: 6
```

| | |
|---|---|
| atgtcccta tactaggtta ttggaaaatt aagggccttg tgcaacccac tcgacttctt | 60 |
| ttggaatatc ttgaagaaaa atatgaagag catttgtatg agcgcgatga aggtgataaa | 120 |
| tggcgaaaca aaaagtttga attgggtttg gagtttccca atcttcctta ttatattgat | 180 |
| ggtgatgtta aattaacaca gtctatggcc atcatacgtt atatagctga caagcacaac | 240 |
| atgttgggtg ttgtccaaa agagcgtgca gagatttcaa tgcttgaagg agcggttttg | 300 |
| gatattagat acgtgtttc gagaattgca tatagtaaag actttgaaac tctcaaagtt | 360 |
| gattttctta gcaagctacc tgaaatgctg aaaatgttcg aagatcgttt atgtcataaa | 420 |
| acatatttaa atggtgatca tgtaacccat cctgacttca tgttgtatga cgctcttgat | 480 |
| gttgttttat acatggaccc aatgtgcctg atgcgttcc caaaattagt ttgttttaaa | 540 |
| aaacgtattg aagctatccc acaaattgat aagtacttga atccagcaa gtatatagca | 600 |
| tggcctttgc agggctggca agccacgttt ggtggtggcg accatcctcc aaaatcggat | 660 |
| ctggaagttc tgttccaggg gcccctggga tccccgaatt ccgggatggc ggcggcggcg | 720 |
| gctcaggggg gcggggcgg ggagcccgt agaaccgagg gggtcggccc gggggtcccg | 780 |
| ggggaggtgg agatggtgaa ggggcagccg ttcgacgtgg gccgcgcta cacgcagttg | 840 |
| cagtacatcg gcgagggcgc gtacggcatg gtcagctcgg cctatgacca cgtgcgcaag | 900 |
| actcgcgtgg ccatcaagaa gatcagcccc ttcgaacatc agacctactg ccagcgcacg | 960 |
| ctccgggaga tccagatcct gctgcgcttc cgccatgaga atgtcatcgg catccgagac | 1020 |
| attctgcggg cgtccaccct ggaagccatg agagatgtct acattgtgca ggacctgatg | 1080 |
| gagactgacc tgtacaagtt gctgaaaagc cagcagctga gcaatgacca tatctgctac | 1140 |
| ttcctctacc agatcctgcg gggcctcaag tacatccact ccgccaacgt gctccaccga | 1200 |
| gatctaaagc cctccaacct gctcatcaac accacctgcg accttaagat ttgtgatttc | 1260 |
| ggcctggccc ggattgccga tcctgagcat gaccacaccg gcttcctgac ggagtatgtg | 1320 |
| gctacgcgct ggtaccgggc cccagagatc atgctgaact ccaagggcta taccaagtcc | 1380 |
| atcgacatct ggtctgtggg ctgcattctg gctgagatgc tctctaaccg gcccatcttc | 1440 |
| cctggcaagc actacctgga tcagctcaac cacattctgg gcatcctggg ctccccatcc | 1500 |
| caggaggacc tgaattgtat catcaacatg aaggcccgaa actacctaca gtctctgccc | 1560 |
| tccaagacca aggtggcttg ggccaagctt ttccccaagt cagactccaa agcccttgac | 1620 |
| ctgctggacc ggatgttaac ctttaacccc aataaacgga tcacagtgga ggaagcgctg | 1680 |
| gctcacccct acctggagca gtactatgac ccgacggatg agccagtggc cgaggagccc | 1740 |

```
ttcaccttcg ccatggagct ggatgaccta cctaaggagc ggctgaagga gctcatcttc    1800
caggagacag cacgcttcca gcccggagtg ctggaggccc cctag                    1845
```